United States Patent [19]

Nigon et al.

[11] Patent Number: 5,252,465
[45] Date of Patent: Oct. 12, 1993

[54] AVIAN ERYTHROBLASTOSIS VIRUS VECTORS FOR INTEGRATION AND EXPRESSION OF HETEROLOGOUS GENES IN AVIAN CELLS

[75] Inventors: Victor-Marc Nigon; Gérard Verdier; Yahia Chebloune, all of Villeurbanne; Francois-Loïc Cosset, Lyons; Catherine Legras, Vaulx-en-Vexin; Astrid Reyss-Brion, Serres; Mustapha Belakebi; Francois Mallet, both of Villeurbanne; Pierre Savatier, Lyons; Pierrick Thoraval; Jacques Samarut, both of Villeurbanne; Didier Poncet, Guyancourt; Claude Bagnis, Romans; Miloud Benchaibi, Villeurbanne, all of France

[73] Assignee: Institut National de la Recherche Agronomique (IMPA), Paris, France

[21] Appl. No.: 477,833

[22] PCT Filed: Oct. 3, 1988

[86] PCT No.: PCT/FR88/00487
 § 371 Date: Jun. 25, 1990
 § 102(e) Date: Jun. 25, 1990

[30] Foreign Application Priority Data

Oct. 21, 1987 [FR] France ................................ 87 14547

[51] Int. Cl.⁵ .................... C12N 15/86; C12N 5/10; C12N 7/01; C12P 21/00
[52] U.S. Cl. .................... 435/69.1; 435/172.2; 435/172.3; 435/239; 435/240.1; 435/240.2; 435/320.1; 935/24; 935/32; 935/34; 935/57; 935/70
[58] Field of Search .................... 435/69.1, 239, 240.2, 435/240.1, 320.1, 172.2

[56] References Cited

U.S. PATENT DOCUMENTS 4,957,865 9/1990 Samarut et al. .................. 435/235.1

FOREIGN PATENT DOCUMENTS 0178996 4/1986 European Pat. Off. .
2596770 10/1987 France .
62-83889 4/1987 Japan .
WO87/03451 6/1987 PCT Int'l Appl. .

Primary Examiner—Richard A. Schwartz
Assistant Examiner—Johnny F. Railey, II
Attorney, Agent, or Firm—Cooley Godward Castro Huddleson & Tatum

[57] ABSTRACT

A viral vector for the integration and expression of at least one heterologous gene in fowl pest cells consists wholly or in part of the proviral genome of fowl pest erythroblastosis or of a related virus in which said heterologous gene(s) replace(s) the v-erbA gene and/or the v-erB gene. Said gene(s) is(are) controlled either by an LTR promoter of the same virus, in which case the heterologous gene(s); mimics(s) the gene(s) it(they) replace, or by a heterologous promoter, in which case the additional att sequence is situated upstream of said heterologous promoter.

19 Claims, 41 Drawing Sheets

FIG_3

```
TSN
AUG*GAA ACC GUC AUA AAG GUG AUU UCG UCC GCG AAA ACC UAU UGG GGG AAA
ACC UCU CUU AAG AAG GAA AUA GGG GCC AUG UCC CUG AAG CAA AAG GAA
GGG UUG AUG UCU ACA CCC CAG UCA CGG UUA GGG GUA AAG UCG GGA GAU CCC UUA AUU
ACC GCG GCG AUG GCA UCC GUU CAG CGG GCG UUG AUG GUA AAG CGA GAG CAG ACA
UCU GGA CAA GAG AGA GAA GCA CGA GCU UAC AAG GAA GCC GUC UCU
GAA GAG GAG AGU CCU CAG G

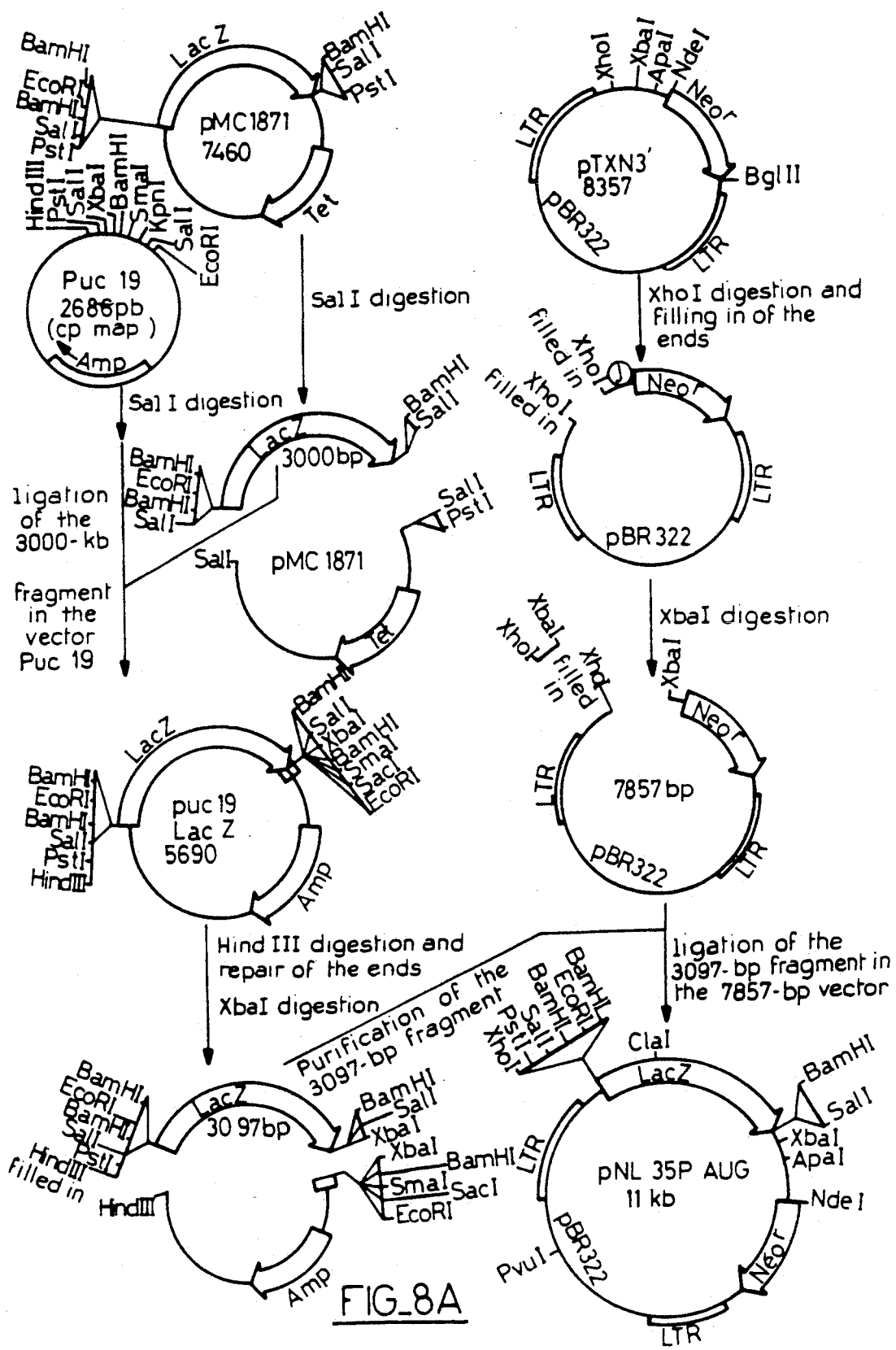
FIG_8A

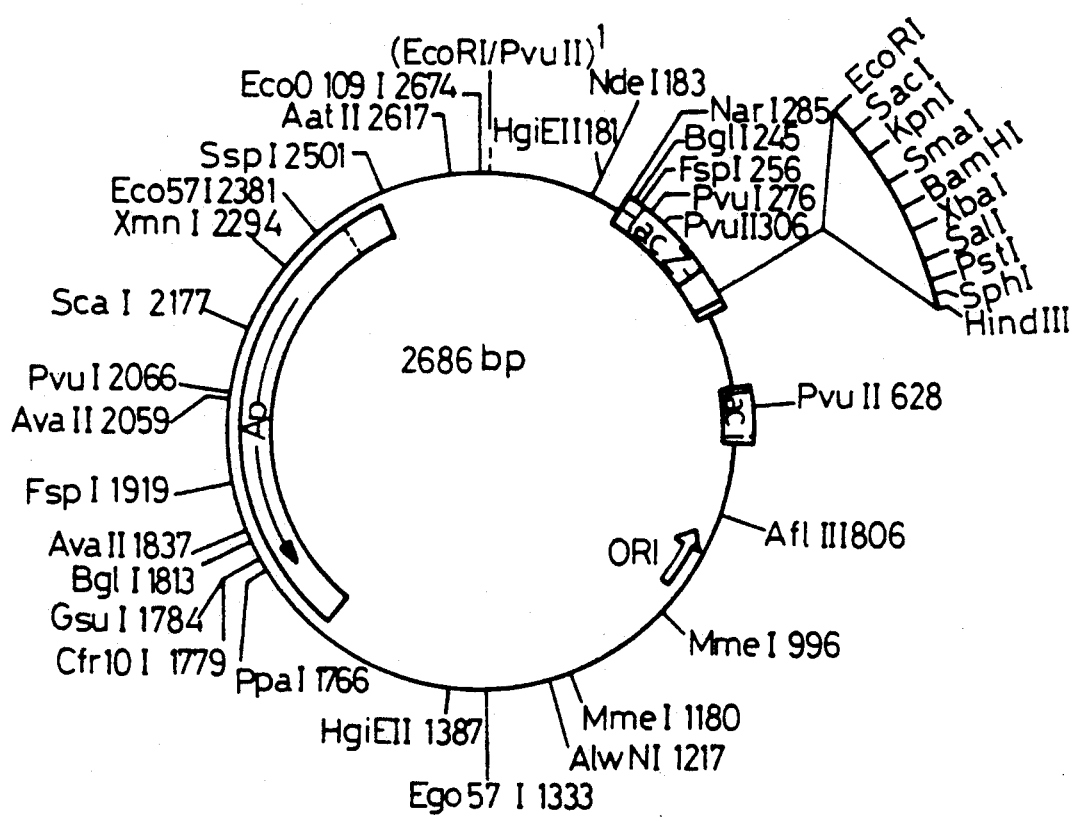
FIG_8B

FIG_11

FIG_12

FIG_13

FIG_14

FIG_15

FIG_16

FIG_18

FIG_19

FIG_20

FIG_21

FIG_23

FIG_24

FIG_25

FIG_27

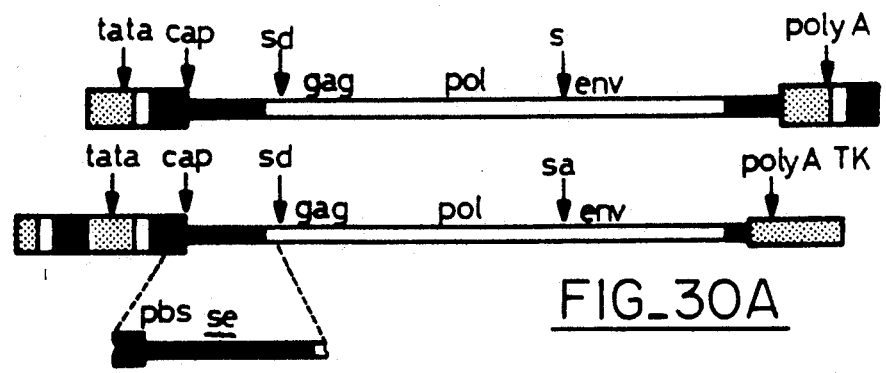
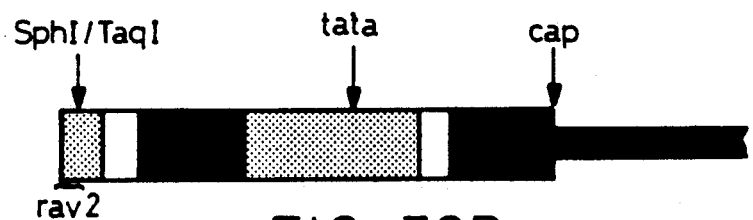
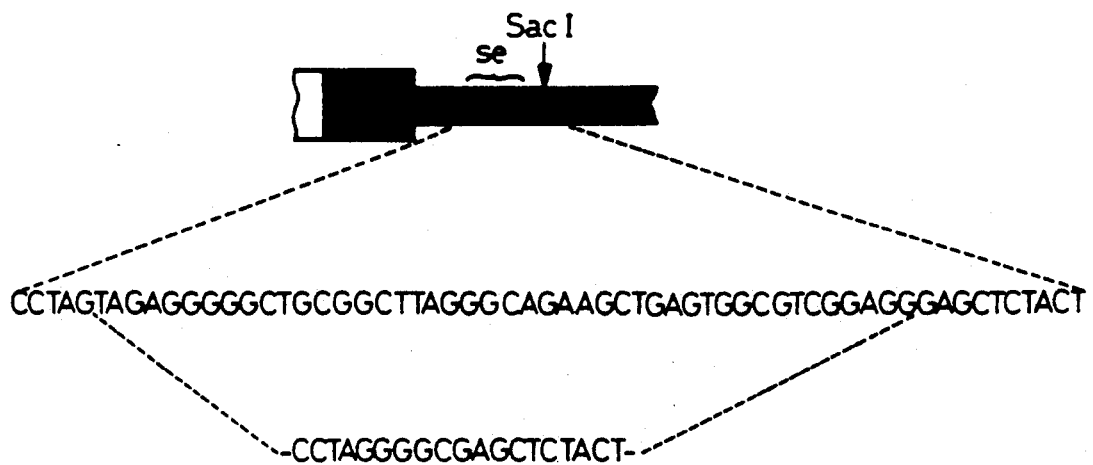
FIG_30C

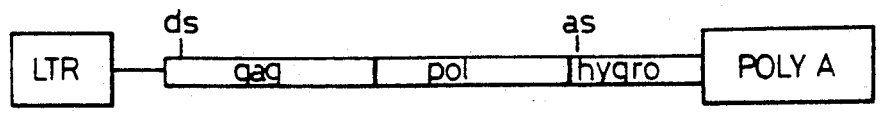
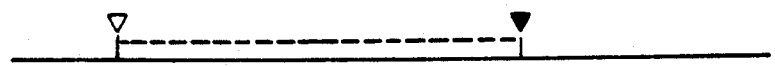
pGP H
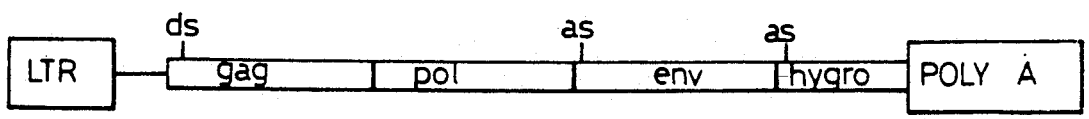
pGPEH
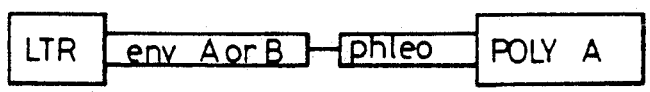
pE$^{A,B}$Ph
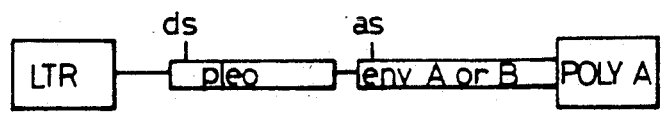
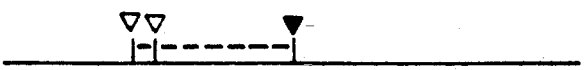
pPhE$^{A,B}$
FIG-31

FIG_35

FIG_36

FIG_37

FIG_39

AVIAN ERYTHROBLASTOSIS VIRUS VECTORS FOR INTEGRATION AND EXPRESSION OF HETEROLOGOUS GENES IN AVIAN CELLS

The present invention relates to new viral vectors for the integration and expression of a heterologous gene in avian cells, and constitutes a development of the invention which is the subject of Patent Applications FR 84/15,764 and EP 178,996 (85 40 1999), to which reference should be made for a better understanding of the present application.

The present invention also relates to plasmids for the integration and expression of a heterologous gene in competent cells.

The present invention relates, in addition, to cells infected or transfected by these viral or plasmid vectors.

Finally, the present invention relates to a method for the production of a protein by culturing these infected or transfected cells, as well as to a method for the genetic modification of animals using these viral vectors.

The retroviral genome represents an integrated structure which drives a cyclic process; one of the phases of this process comprises a regular integration of the viral genome in the cell DNA. This feature is associated with other properties which, by various mechanisms, endow some of these viruses with pathogenic properties with respect to their hosts.

An objective of the present invention is to use certain properties of retroviral structures for transferring genes to whole animals, in their somatic structures for the purpose of "gene therapy", or in their germinal structures for the purpose of transmission to the progeny. To achieve this objective, it is necessary to break up the process of operation of the retroviral structure in order to retain only the component of it whose use is justified by the desired objective. At the same time, all the parts liable to exert pathogenic effects will be eliminated. In particular, all transmission to the target subjects of potentially dangerous oncogenes, or of structures capable of permitting viral multiplication to continue in the chosen target, will have to be absolutely prohibited.

An object of the invention is, in effect, to obtain viral vectors capable of a high transfer efficiency which are usable for infecting the animal and, to this end, to obtain the situation where the viruses, actively multiplied in vitro, are capable of being inserted into the animal but become incapable of multiplying therein.

An object of the present invention is hence to produce vectors relieved of oncogenic sequences and capable of transporting other genes, in a configuration permitting the most efficacious possible expression of the latter.

Thus, in EP 178,996, the main vectors described still contained the erbA oncogene. According to the present invention, this oncogene has, in its turn, been deleted.

According to the present invention, optimization of retroviral vectors, the subject of the previous patents cited above, was sought.

Optimization of the vectors was sought by working, respectively, on the activity of the promoters and on the efficacy of the system of maturation and translation of the RNAs.

The subject of the present invention is, in effect, a viral vector for the integration and expression of at least one heterologous gene in avian cells, which consists wholly or in part of the proviral genome of avian erythroblastosis or of a related virus in which said heterologous gene(s) replace(s) the v-erbA gene and/or the v-erbB gene, and wherein said gene(s) is/are either controlled by an LTR promoter of the same virus, in which case the heterologous gene(s) mimic(s) the gene(s) it/they replace(s), or controlled by a heterologous promoter, in which case an additional att sequence is situated upstream from said heterologous promoter.

Heterologous gene is understood to denote a gene which is not normally present in the genome of the avian erythroblastosis virus. It can be a so-called "useful" gene coding for a protein of industrial interest intended for production by cell culturing, or alternatively a gene which can be of special interest in the treatment or breeding of birds, in particular chickens, a gene providing for vaccination or better development, for example, or it can alternatively be a marker gene, especially for resistance to an antibiotic.

Heterologous promoter is understood to denote an efficacious promoter which is not normally present in the genome of the virus; it can be, in particular, a eukaryotic promoter. The promoter of the simian virus SV40 may be mentioned in particular.

The viral vectors mentioned in the context of the present invention can be both plasmid vectors or, where appropriate, DNA fragments, and true RNA viral vector as already mentioned in the Applicant's previous patents.

The viruses to which the present invention relates more especially are AEV and related viruses of the ALSV type, as well as non-defective viruses of the RAV type.

Different promoters were tested and were placed in vectors in various configurations.

The activity of these vectors after stable insertion was examined on CEF and on QT6.

Study of the activity of the promoters shows that, in the case of normal chick cells, the use of an avian LTR promoter is preferable. The promoters of the TK gene exercise virtually no activity thereon. The SV40 promoter exercises an activity, although weaker than that of an avian LTR. In QT6 cells, it is possible to use either an LTR promoter or a heterologous promoter.

In the second place, a major difficulty in the expression of genes carried by vectors derived from AEV results from the particular mechanism of translation of the erb-A and erb-B oncogenes in wild-type AEV: translation is not initiated at respective AUG codons of these genes (v-erbA has no AUG; the AUG of v-erbB is an internal codon). Initiation takes place at the initiator codon of the residue of the gag gene located at the 5' end of the erb-A gene. This results in the production of two fusion proteins known as gag-erbA and gag-erbB.

Several vectors transporting one or more heterologous genes were constructed. For example, the neo gene was inserted either in place of the erb-A oncogene or in place of the erb-B oncogene and, for each of the two positions, it was inserted either in the same reading frame as the oncogene it replaces or in a different reading frame. In one construction, the 3'-terminal portion of the residue of the gag gene was deleted for the purpose of reducing the length of the gag-neo fusion protein. In others, this region was simply shifted so as to retain the functions of encapsidation and of stimulation of transcription which it is capable of exercising. It was sought to determine, in particular:

which configurations lead to maximal production of neomycin phosphotransferase;

whether it is possible to obtain a neomycin phosphotransferase protein not containing the $N_2$-terminal amino acids encoded by the gag gene and whose translation would be initiated at the AUG belonging to the neoR gene.

The expression of a heterologous gene is maximal when its mechanism of translation mimics that of the erb-A or erb-B oncogenes which it replaces. Competition is then established between the AUG of the gag gene and that of the heterologous gene for the initiation of translation; this competition proves to be totally to the advantage of the viral AUG. In some structures, it is possible to observe the functioning of the specific AUG of the heterologous gene. However, the level of expression then remains very low. An improvement consists in introducing a translation stop signal into the gag gene. This signal permits a reinitiation of the translation at the AUG of the heterologous gene, and hence the production of a protein not fused to the viral gag protein. In effect, it proves necessary, for some applications, to obtain a specific expression of the exogenous sequence in order to retain all the characteristics of the encoded protein.

In a first embodiment which is useful, in particular, for integration in chick cells, the heterologous gene(s) is/are hence controlled by an avian LTR promoter, and it/they mimic(s) the gene(s) it/they replace(s).

In a suitable arrangement, the vector contains a first, heterologous marker gene in the v-erbA position and a second, useful heterologous gene in the v-erbB position.

The essential advantage of the vectors in question is, in effect, to be able to replace, between the two LTRs, the two oncogenes by a marker gene and a practically useful gene. During tests which were performed, it was found that, in some cases, the resistant strains no longer produced the protein of interest, although they retain the expression of the marker gene. This takes place at a significant frequency when the resistance gene is placed at the 3' end. In contrast, when the latter gene is placed at the 5' end, preservation of the practically useful gene is much better. One of the explanations might be that this originates from a splicing at the level of the transcription process. The 5' end is spliced and, in some translations, would cause the gene present at the 5' end to disappear. On the other hand, the second gene from the 3' end is well expressed and, when it is the marker gene, the latter confers resistance on the cells, which are hence selected. In order to avoid this drawback, the practically useful gene should be placed in the 3' position, namely v-erbB. Under these conditions, all the cells selected for a resistance will also be productive cells.

Advantageously, according to another feature of the invention in this embodiment, said heterologous gene(s) is/are translated from the AUG of the gag gene or from its (or their) own AUG(s), but always in the same reading frame as that of the gag gene.

Thus, where appropriate, the first, heterologous marker gene is translated from the AUG of the gag gene and the second, useful heterologous gene is translated from the AUG of the gag gene or its own AUG.

Advantageously, a stop codon is introduced between the gag gene and the useful heterologous gene or the AUG belonging to said useful gene.

Preferably, the stop codon is located at an optimum distance of 65 nucleotides from the AUG codon of said useful gene.

Another object of the invention is to produce vectors capable of prolonging life in cell cultures.

Vectors according to this first embodiment, into which vectors there are inserted a marker gene in the v-erbB position and a fusion gene composed of the Δ gag sequence and the sequence of the v-myc oncogene derived from the genome of the avian retrovirus MC29 in the v-erbA position, or alternatively vectors which possess the p53 gene in the v-erbA or v-erbB position and a marker gene in the v-erbB or v-erbA position, respectively, were hence also produced. The latter vectors confer properties of perpetuation on the avian cells they infect.

In EP 178,996, the vectors described, capable of prolonging the in vitro culture life of chick fibroblasts, had an action which proved to be due to the erbA oncogene. The use of other oncogenes than erbA show that the myc gene is markedly more efficacious.

The infection of a cell by a retrovirus leads to the production of a circularized proviral DNA containing either an LTR or two LTRs in tandem. Recent data have shown that the latter form fulfils a decisive function in the process of integration of the proviral DNA within the cell DNA. In effect, the arrangement of two LTRs in tandem creates a structure, referred to as att, which contains 30 nucleotides: 20 are carried by the U5 segment of the 3'-terminal portion of the 3' LTR, and 10 are carried by the U3 segment of the 5'-terminal portion of the 5' LTR. The functioning of this structure requires the participation of a nuclease activity carried by the Pol gene. According to the present invention, the property of the att sequence were exploited to obtain the integration of plasmid DNAs without other relationships with a retroviral sequence.

An 88-bp segment carrying the att sequence was extracted from a pJS21 clone carrying an LTR doublet. This segment was inserted into different plasmids.

In a second embodiment of the invention, a first, heterologous marker gene is in the v-erbA position controlled by an avian 5' LTR promoter and a second, useful heterologous gene is in the v-erbB position controlled by a heterologous promoter, the vector containing an additional att sequence situated upstream from the heterologous promoter.

In effect, the use of an additional att sequence in the viral constructions enables a gene to be placed under the influence of a promoter which is not the promoter present in the LTR. In vectors of the AEV type, it is not, in effect, possible to provide for the promotion of a gene apart from the use of the 5' LTR promoter. During replication of the virus, the 5' and 3' ends, that is to say the two LTRs, are induced to fuse; the central portion of this fusion is referred to as the att sequence. If a vector is constructed in which an additional att sequence has been introduced between the two LTR sequences, this additional att sequence being followed, for example, by an SV40 promoter or by any heterologous promoter providing for the promotion of a gene, it is found that some of the transformed cells express the gene placed under the promotion of said heterologous promoter. This corresponds to constructions in which the 5' and 3' LTR structures remain fused, that is to say the additional att sequence has been used for integration. This phenomenon was demonstrated, in particular, in a mixed construction containing, in the 5'-3' reading direction, the neo gene controlled by the 5' LTR promoter, and in the 3'-5' reading direction, the hygro gene controlled by the SV40 promoter preceded by an additional att sequence.

When the cells are infected or transfected with this type of vector, resistance to the neo gene is observed in some of them, which proves that the 5' LTR promoter is then functional, but, in contrast, in some of them, resistance to hygromycin demonstrates that it is the SV40 promoter which is active and, in these constructions, the 5'–3' LTR fusion product has remained intact and its two ends cancel each other, as it were, in their capacity for promotion.

The advantage of using a non-retroviral eukaryotic promoter different from the LTR promoter is that it is possible to put in a promoter which is inducible, which is not possible in the case of the LTR promoter, or alternatively a promoter specific to the target tissue.

In the vectors which have an additional att sequence, a portion of the U5 sequence of the 5' LTR can be deleted so that, after a retroviral cycle, only the additional att sequence which provides for integration remains functional. Preferably, a deletion of 23 bp is performed in the 3'-terminal region of the U5 sequence of the 5' LTR. The additional att sequence permits an exclusive integration; the natural att sequence generated by the function of the 2 LTRs during the first retroviral cycle is inactive as a result of the deletion of the U5 sequence.

Advantageously, a feature of the vector is that the second heterologous gene is in the v-erbB position flanked by the heterologous promoter and the heterologous polyadenylation sequence, and that the (promoter—useful gene—polyadenylation sequence) assembly is in the opposite orientation to the retroviral transcription direction.

The promoter of the simian virus SV40 may be mentioned as a heterologous promoter.

The production of the virions is most conveniently performed on immortalized cell lines. Two lines which possess these properties are employed:
the quail QT6 cell line, derived from treatment of these cells with chemical carcinogens. Unfortunately, quail cells multiply only viruses belonging to certain subgroups;
a chick lymphoblastoid cell line (RPL line) derived from cells treated with Marek's disease virus. The use of this line is only just beginning.
The above lines are not viroproductive.

To obtain preparations of defective viral vectors, without the addition of a helper virus, it was sought to produce helper cell lines capable of supplying a defective genome with the gag, pol and env proteins needed to enable it to form virions.

The results observed show that the production of avian helper cells can indeed be carried out. The lines obtained to date are endowed with a viral productivity to create, by infection using the viruses obtained, cell lines resistant to G418 and which are non-viroproductive.

Another object of the present invention is hence to construct a permanent helper cell line capable of producing helper-free viral preparations.

In EP 178,996, a TK promoter or an SV40 promoter were used to construct vectors capable of transforming a normal cell to helper cells, the starting points of the constructions being the classical helpers of the AEV or RAV-1 virus in particular.

According to the present invention, an LTR promoter is used in which deletions have been made in order to abolish the capacity for encapsidation of the RNA encoded by this vector.

The subject of the present invention is, in effect, also a vector capable of transforming a normal avian cell to a helper cell, which vector contains the three genes gag-pol-env of the RAV-1 virus placed under the transcriptional control of an LTR of the same virus in which various deletions have been made in order to abolish the capacity for encapsidation of the RNA encoded by this vector.

Preferably, the vector contains a marker gene placed at the 3' end of the env gene and a second splicing acceptor site upstream from the marker gene.

In one embodiment, the env gene has been deleted.

In another embodiment, the gag and pol gene have been deleted and replaced by a marker gene, the env gene which remains being preceded by a splicing acceptor site.

The subject of the present invention is hence also a plasmid for the integration and expression of a heterologous gene in avian cells, which plasmid contains a composite sequence of DNA reverse-transcribed from a retroviral vector.

In particular, the subject of the present invention is a plasmid for the integration and expression of a heterologous gene in competent cells, which plasmid is a DNA plasmid containing at least one att sequence of a retrovirus providing for integration in the cell DNA.

The virions obtained by transfection with such a plasmid and with a helper virus must then contain the products encoded by the pol gene, namely the reverse transcriptase and integrase conjugates, introduced during the processes of encapsidation, without the corresponding gene forming part of the encapsidated genome. As a result, the genome may be integrated while remaining capable of determining the formation of functional virions.

The subject of the present invention is hence also cells infected by a viral vector or transfected by a plasmid according to the invention.

According to another feature, the cell is capable of complementing the viral vector.

Finally, the subject of the present invention is a method for the production of a protein encoded by a heterologous gene, wherein infected or transfected cells according to the invention are cultured.

Similarly, the subject of the present invention is a method for the genetic modification of animals, wherein the germ cells or cells to be treated are infected with a viral vector according to the present invention.

The germ cells or cells to be treated may be infected with a viral vector non-productive of virus, according to the invention.

The subject of the present invention is finally a method for the production of avian helper cells or for the immortalization of avian cells, wherein normal avian cells are transfected or cotransfected with some of the vectors according to the invention mentioned above.

The examples below describe the constructions of various vectors produced:

A - From the avian erythroblastosis virus (AEV):

This defective retrovirus contains two oncogenes, v-erb A and v-erb B, expressed independently from two different RNAs (see FIG. 1). These two oncogenes were deleted in order to use the AEV genome in constructions capable of transporting two genes inserted at the v-erb A and v-erb B positions respectively.

In a first set of constructions, a single gene (the gene coding for neomycin phosphotransferase, the NeoR gene, conferring resistance to the antibiotic G418) was inserted either in the v-erb A position or in the v-erb B position. Depending on the construction carried out, the AUG translation initiation codon of the inserted gene is placed in phase or otherwise with the AUG of the residual fraction of the gag retroviral gene (Δgag).

In a second set of constructions, two genes were inserted, one used for selection of the cells after transfection, the other serving as a model gene for the study of gene expression in a retroviral vector. Furthermore, vectors were constructed in which retroviral sequences described as being necessary for integration of the provirus in the genome of the target cells (att sequence) were placed at the 5' end of the genes inserted into these vectors.

B - From the RAV-1 helper genome (FIG. 30 A)

These constructions set out to place the gag-pol-env retroviral genes, necessary to the retroviral cycle, under the transcriptional control of various viral sequences. They were carried out in order to produce trans-complementing cells expressing the gag-pol-env genes constitutively by inhibiting the encapsidation of the genomes carrying these genes in the virions synthesized. The expression of these genes in such cells can then lead to the production of helper cell lines permitting the production only of defective vector viruses derived from AEV, as a "helper-free" viral stocks.

The examples fall into two main sections:
the first in which the constructions derived from AEV are described (Examples 1 to 3),
the second which relates to the constructions involving the genome of the RAV-1 helper virus (Examples 4 and 5).

These examples are given with reference to drawings, wherein:

FIG. 1 shows the structure of the genome of wild-type AEV (obtained from Dr J. M. Bishop, U.S. San Francisco), with the associated transcribed and matured RNAs (continuous lincs) and polypeptides translated (heavy dashes). v-erb A and v-erb B genes are translated from the AUG of the gag gene to form the gag-erb A p75 and erb B p61 fusion proteins.
ds=splicing donor site
as=splicing acceptor site FIG. 2 shows the construction of the vectors pTSN and pTXN3'. These vectors are directly derived from the vectors pBRgag-J-env2LTR (or pTS) for pTSN, pTSN and pXJ12 for pTXN3', according to the procedure described below. In the case of pTSN, this involves placing the Neor gene in the 5' position at the XbaI site behind the gag sequence of the vector. pTXN3', for its part, corresponds to the vector pXJ12 as regards the position of the Neor gene. The difference lying in the complete disappearance of oncogenic sequences.

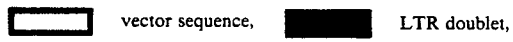

A:ApaI, B:BamHI, Bg:BglII, E:EcoRI, N:NdeI, P:PvuII, X:XhoI, Xb:XbaI.

FIG. 3 shows the construction of the vectors pTXN3' gag- and pTXhoN. These vectors are directly derived from the vector pTXN3' according to the procedure described below. pTXN3' gag- is derived from pTXN3' after deletion of the gag sequence between the XhoI and XbaI sites. The construction of pTXhoN represents the placing of the Neor gene in the 5' position at the XhoI site without taking into account the reading frame of the gag gene.

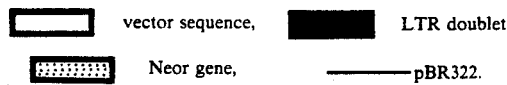

A:ApaI, B:BamHI, Bg:BglIII, b.e.: blunt end, N:NdeI, P:PvuII, X:XhoI, Xb:XbaI.

FIG. 4 shows the construction of the vector pTXN5'. This vector is indirectly derived from pTXN3'. The object of this construction is to place the Neor gene in the 5' position at the XhoI site in the reading frame with the AUG of the gag gene of the vector. The sequences appearing in the figure and shown as triplets correspond to the enzyme sites present or created by the insertion of linkers. Each triplet represents a codon, thereby indicating the open reading frame with the AUG of the gag gene and of the vector.

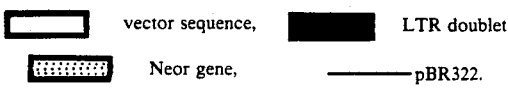

A:ApaI, B:BamHI, Bg:BglIII, E:EcoRI, N:NdeI, P:PvuII, X:XhoI, Xb:XbaI.

The sequences shown in FIG. 5 correspond to the coding portions (representation as base triplets) separating the AUG of the gag gene (*) from the AUG of the Neor gene in the different vectors. An additional AUG is present in the sequences of the vectors TSN and XJI. It belongs, in fact, to a sequence of the transposon Tn5 from which the Neor gene is derived. The AUG in brackets in the XJI sequence represents an AUG of the v-erb B gene still present in this vector (see Patent EP 8540019999).

When the Neor gene is located in the 3' position, and consequently expressed on the subgenomic RNA, the sequences represent the RNA after splicing (the / sign indicates fusion between the splicing donor site and the acceptor site).

FIG. 6 shows the construction of the vector pNL 35P.

Plasmid pMC 1871, marketed by Pharmacia, was digested with the enzyme SalI, and the 3.1-kb fragment carrying the LacZ gene was purified on an agarose gel. This fragment was inserted into the single XhoI site (the XhoI and SalI sites are compatible) located in the gag region of the vector.

This results in the vector pNL 35P; the LacZ gene in this vector does not possess its own AUG; it is translated from the AUG of the delta-gag retroviral gene and is expressed in the form of a delta-gag-Lacz (sic) fusion protein. The reading frame of the LacZ gene is in phase with the delta-gag AUG.

FIG. 7 shows the construction of the vector pNL 53gpt.

Plasmid pMMuLVSV-LacZ was doubly digested with the enzymes HindIII and BamHI, and the ends were repaired with Klenow polymerase. The 3.5-kb fragment carrying the Lacz (sic) gene and the 280-bp fragment of the gpt gene was purified on an agarose gel and then integrated in the vactor (sic) pTXN5' previously linearized with the enzyme EcoRI, and the ends were repaired with Klenow polymerase.

This results in the vector pNL 53 gpt.

The 280-bp fragment of the gpt gene is represented by: ▭

The hatched portion ⊔⊔⊔⊔ in pMMuLVSV-LacZ corresponds to mouse cell DNA.

The arrows borne by the genes correspond to their direction of transcription.

B.E.: blunt end.

FIG. 8A shows the construction of the vector pNL 35 AUG (Example 2).

FIG. 8B shows the restriction map of PUC 19.

The 1751-bp fragment was released, by double digestion using the enzymes EcoRI and BamHI, from plasmid pJS21 containing an LTR doublet derived from fusion of the AEV genome, flanked on each side by the residues of the gag and env genes, and inserted between the EcoRI and BamHI sites of plasmid pBR322, the fragment then being purifies on agarose gel. A 340-bp subfragment is released from this fragment by single HinfI digestion, and is purified on 2.5% agarose gel. MaeIII digestion, as well as purification on polyacrylamide gel, enables an 88-bp fragment to be obtained, containing the "att" sequence whose sequence we give (B : BamHI, E : EcoRI, Hf HinfI, M : MaeIII, Ps : Pst I).

Figure 16:
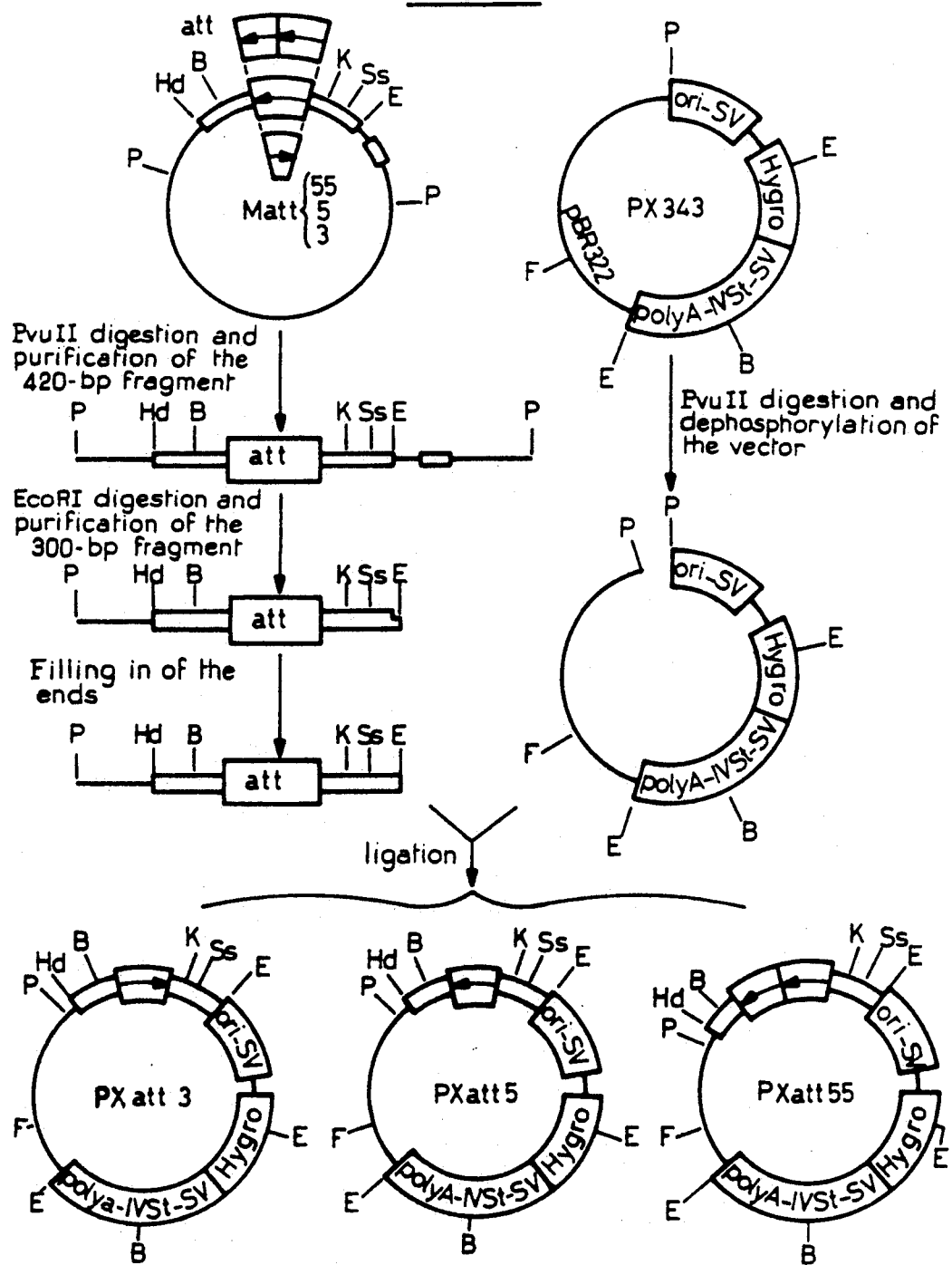

FIG. 16 shows the subcloning of the "att" sequence equipped with the polylinker into plasmid PX343.

The 420-bp fragments (or 508 for that derived from Matt55) are released by PvuII digestion from the clones Matt3, Matt5 and Matt55, and purified on agarose gel. This fragment is recut with EcoRI and the 266-bp (or 354-bp) fragment is recovered and purified on agarose gel. The projecting 5′ ends generated by this enzyme are filled in with Klenow polymerase, and the fragments subcloned upstream from the SV40 promoter of plasmid PX343 which has been previously linearized with the enzyme PvuII and dephosphorylated. This results in 3 clones carrying the "att" sequence, either in one direction (PXatt3), or in the other (PXatt5), or as a doublet in the same direction as the latter (PXatt55). These vectors are shown adopting the same conventions of orientation as for the Matt vectors. (B: BamHI, E: EcoRI, F: FspI, Hd: HindIII, K: KpnI, P: PvuII, Ss: SstI, oci-SV: origin of replication of SV40, polyA-IVS-t-SV: polyadenylation sequence and intron of the gene coding for the t antigen of SV40).

Figure 17:
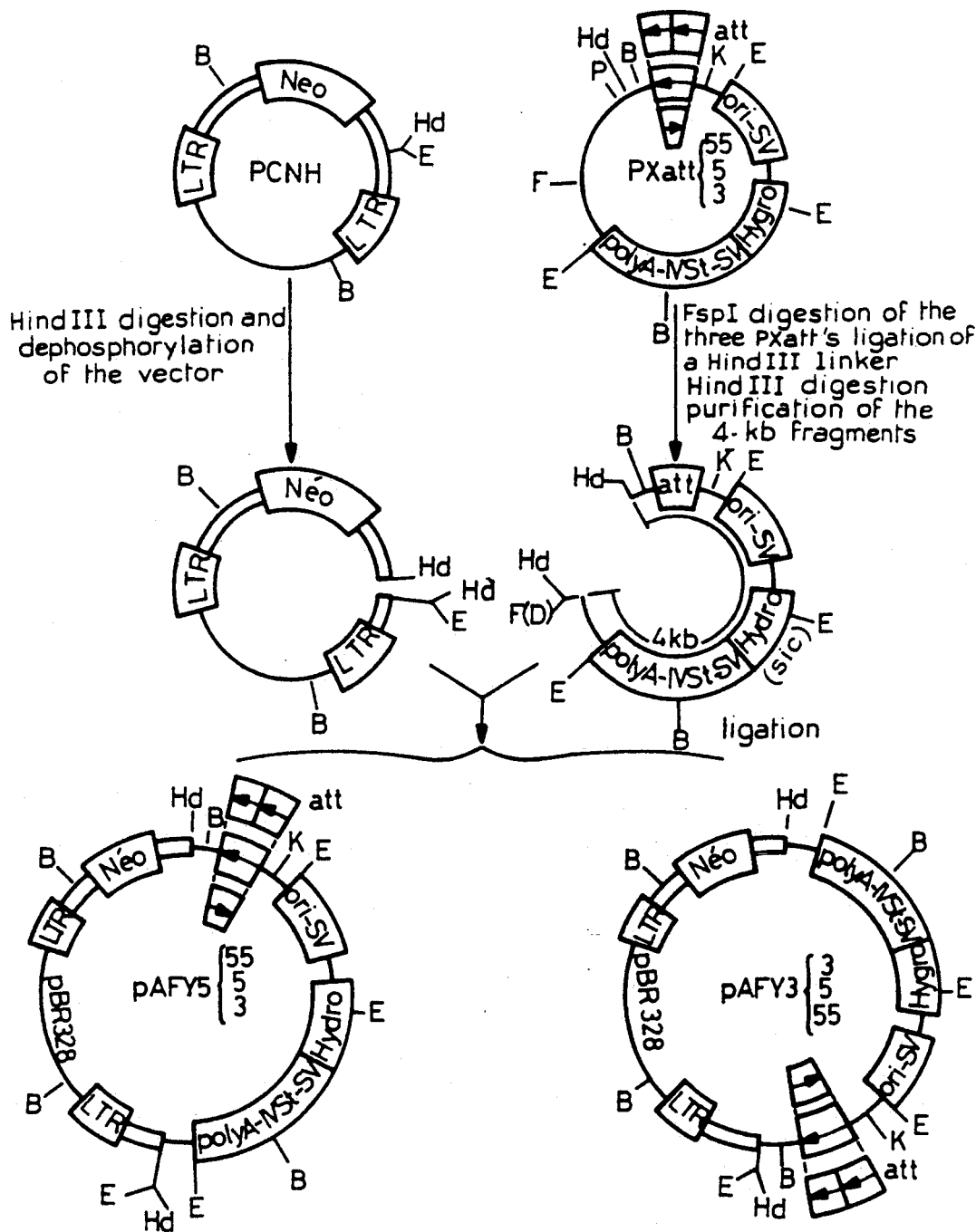

FIG. 17 shows the construction of the retroviral vectors pAFY.

Plasmids PXatt were linearized with the endonuclease FspI and HindIII linkers were ligated onto the blunt ends generated by the former enzyme. The 4-kb fragments carrying the "att" sequence-Hygro gene with the SV40 promoter are isolated on agarose gel after HindIII digestion, and then inserted into the HindIII site of pCNH. Insertion into this vector can be done in both directions. Two types of pAFY vectors are obtained, and identified by restriction mapping. pAFY53, pAFY55 and pAFY555 are defined as the vectors carrying the att-hygro assembly in the same direction as that of retroviral transcription, and the vectors pAFY33, pAFY35 and pAFY355 as the vectors carrying this assembly inserted in the opposite direction. (B: BamHI, E: EcoRI, Hd: HindIII, K: KpnI).

Figure 18:
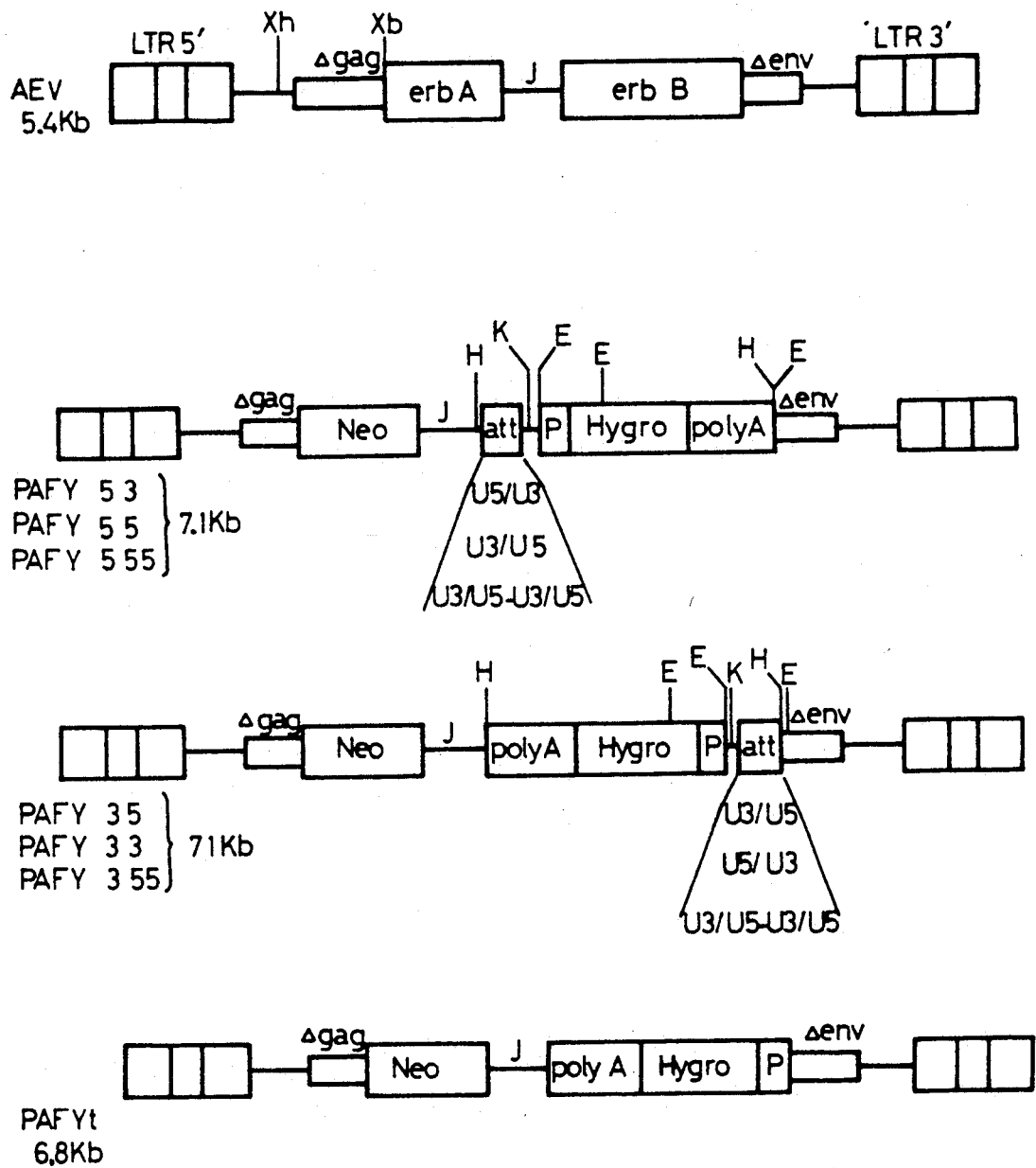

FIG. 18 shows the retroviral vectors pAFY.

These vectors are shown without the plasmid portion which is used for their amplification. The lines represent the non-coding sequences of retroviral origin, the small boxes represent the residues of the gag and env retroviral genes and the large boxes represent the LTRs as well as the sequences which are not of retroviral origin. (B: BgLII, E: EcoRI, H: HindIII, K: KpnI, Xb: XbaI, Xh: XhoI)

Figure 19:
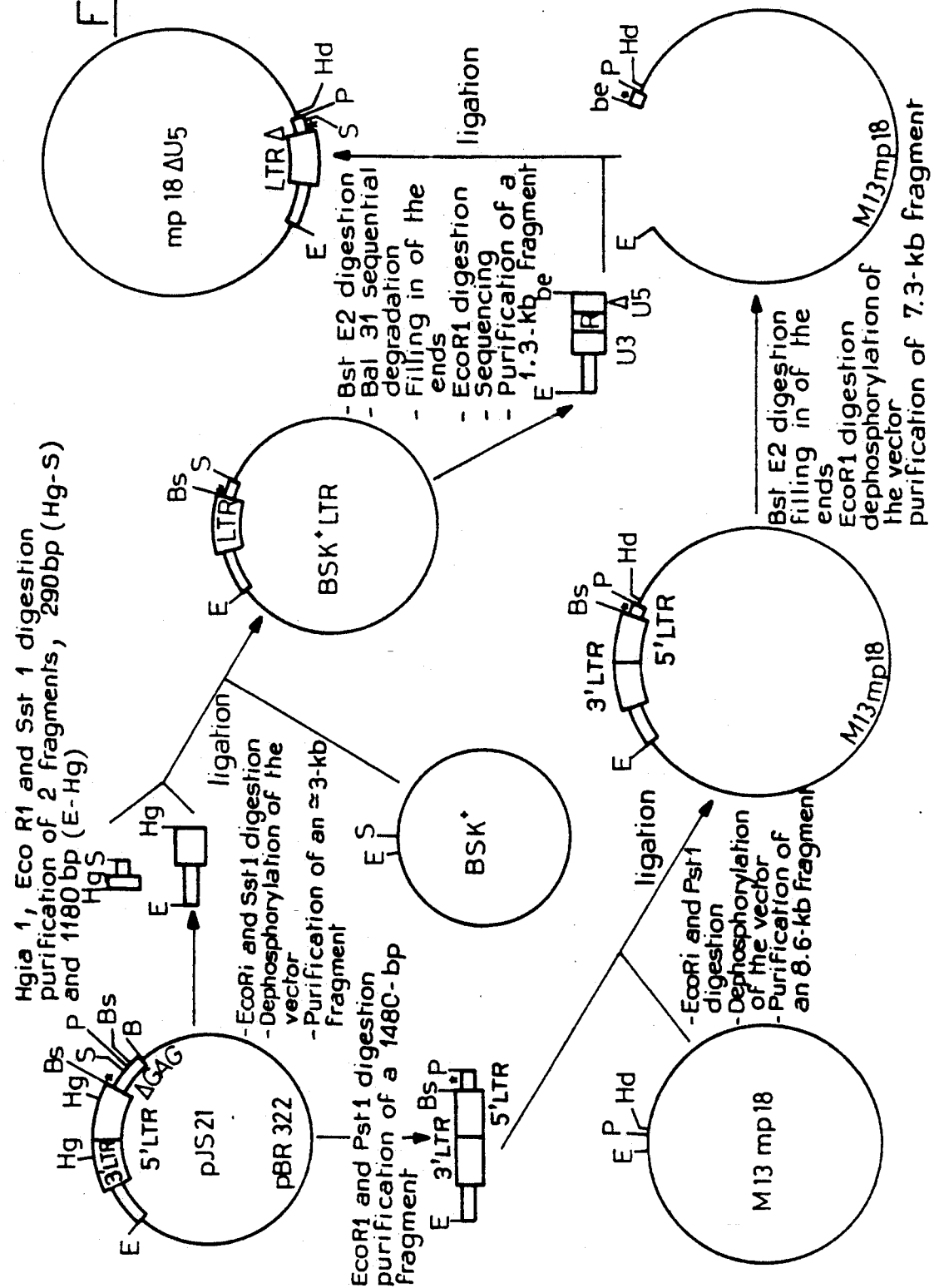

FIG. 19 shows the construction of plasmid BSK LTR.

Figure 20:
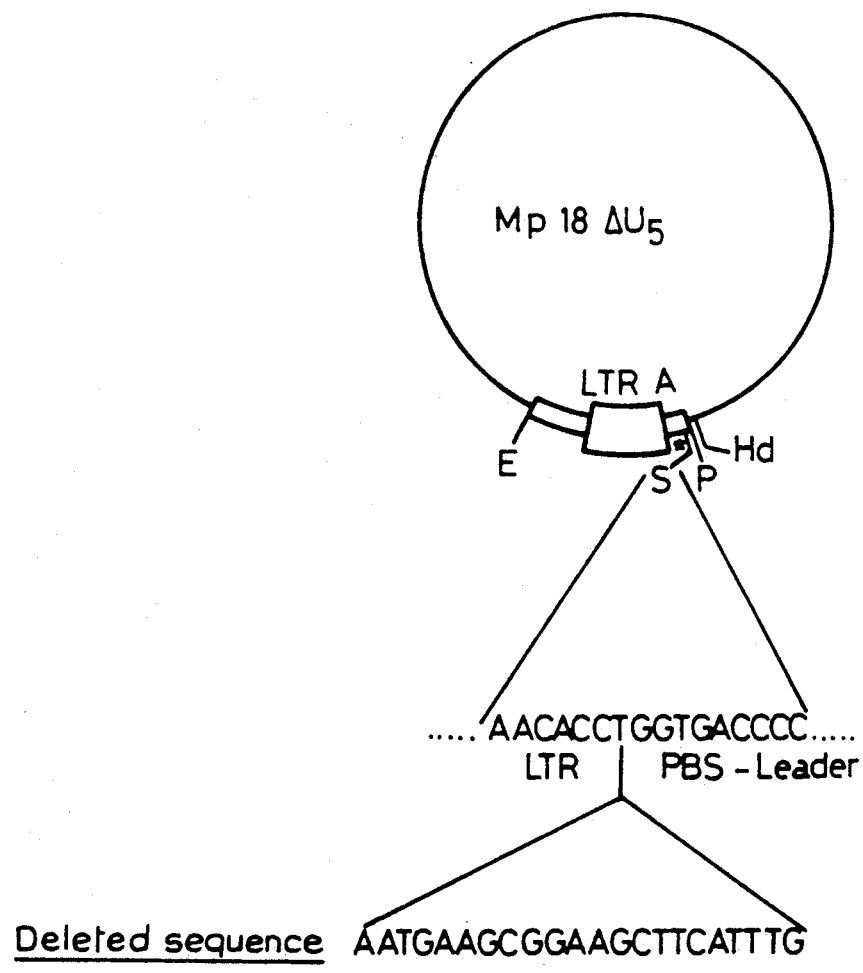

FIG. 20 is a diagrammatic representation of the recombinant coliphage M13mp18ΔU5.

the single-line circle represents the genome of the coliphage M13mp18.

the double-line portion represents the mutated LTR and its flanking sequences.

the first sequence line corresponds to that of the 3′ end of the mutated U5 sequence of the LTR, the second to the deleted portion (23 bp).

Figure 21:
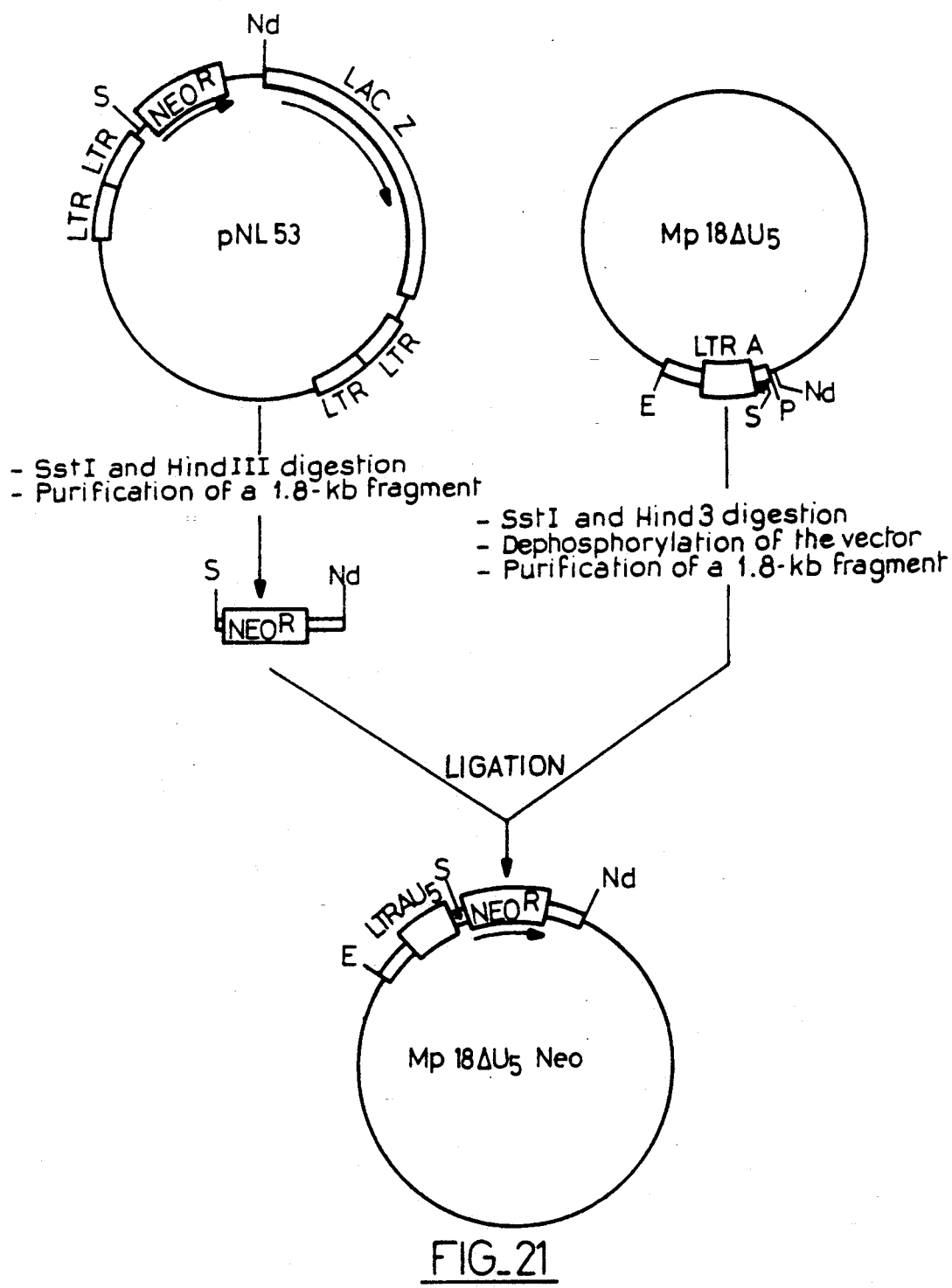

FIG. 21 shows the insertion of the gene for resistance to neomycin into the recombinant coliphage M13mp18ΔU5.

This figure illustrates the step of construction of the recombinant coliphage M13mp18 U5Neo from M13mp18 U5.

Figure 22:
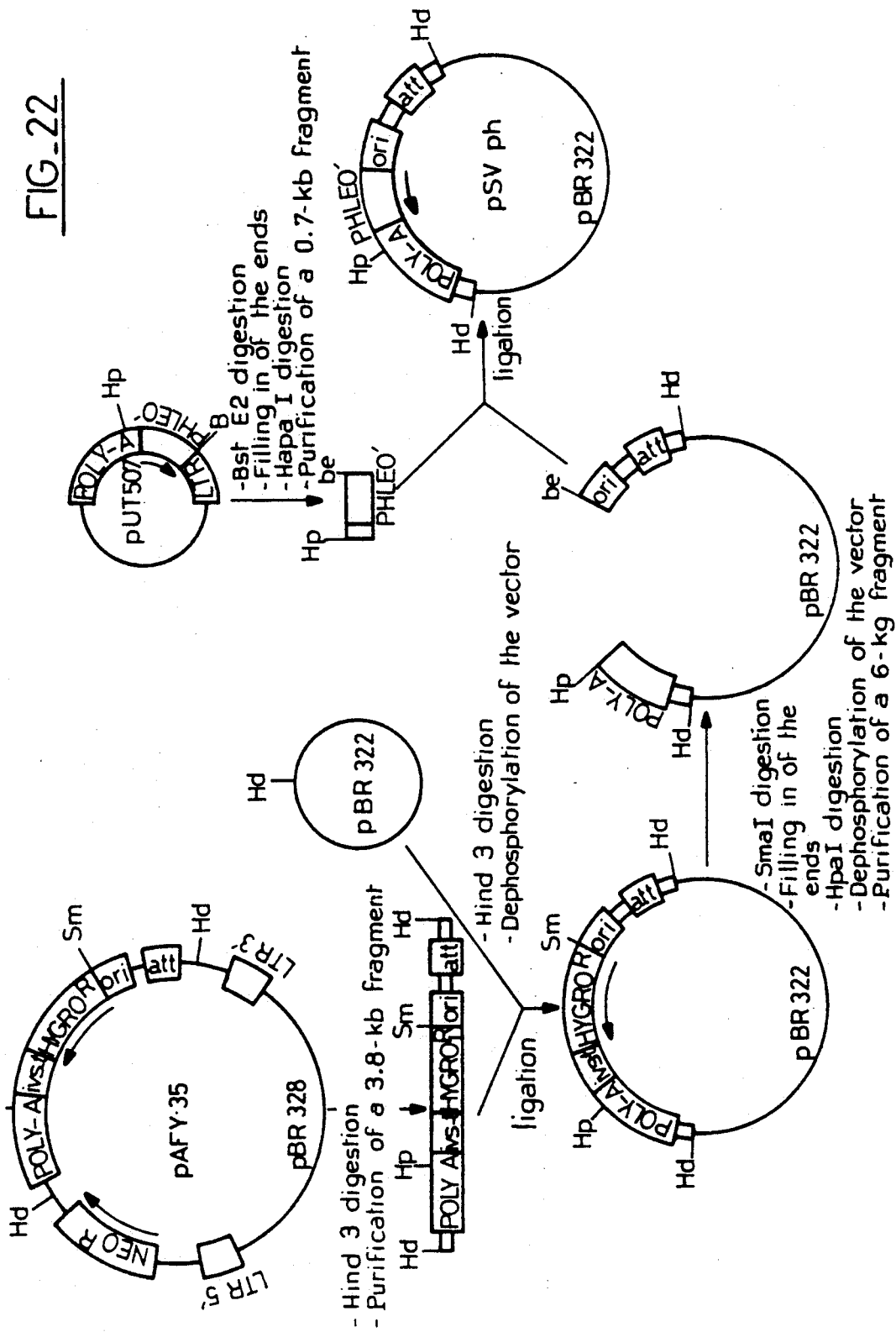

FIG. 22 shows the construction of plasmid PSVph (Example 3).

Figure 23:
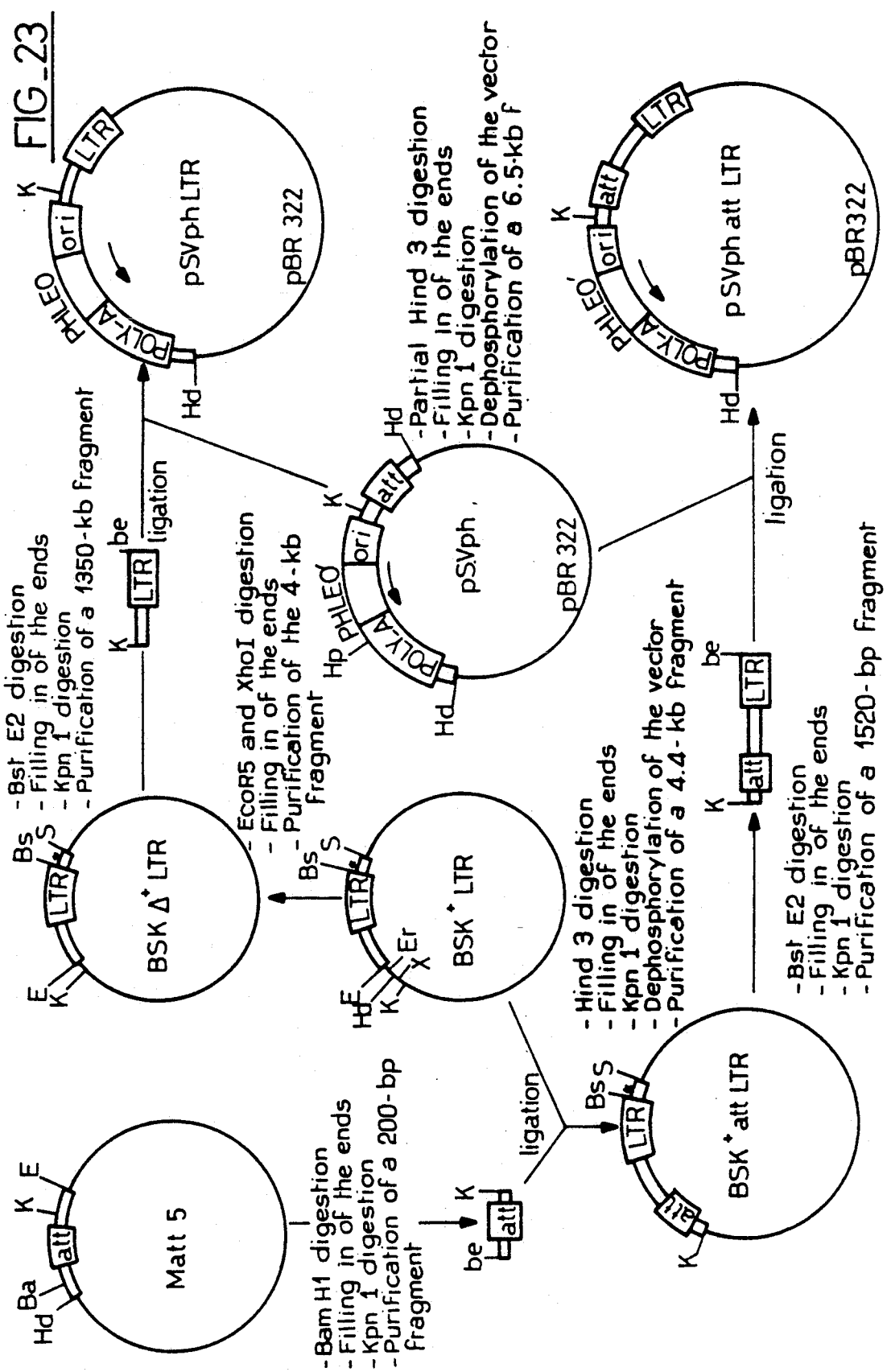

FIG. 23 shows the construction of plasmid BSK+ att LTR (Example 3).

Figure 24:
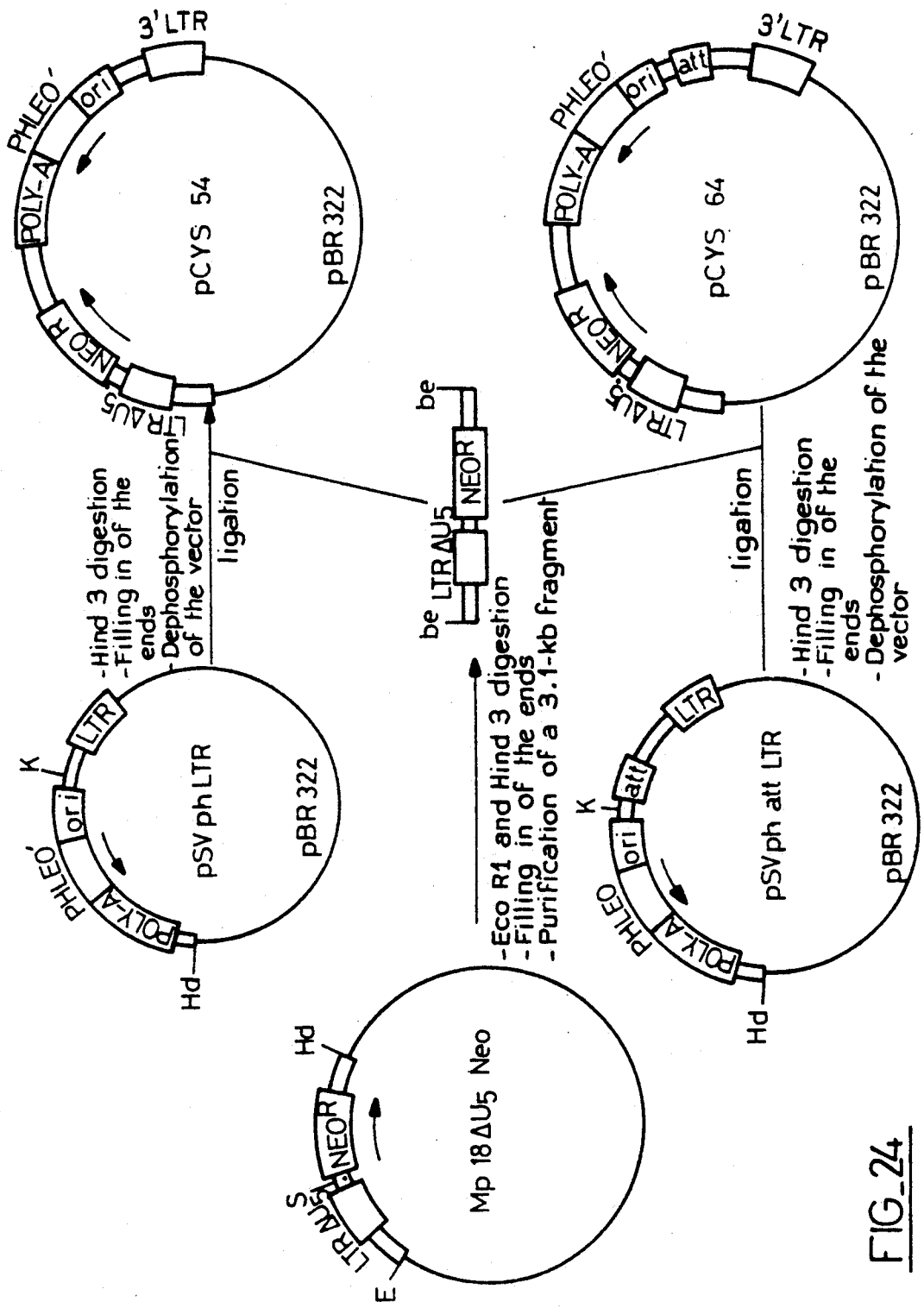

FIG. 24 shows the construction of plasmid pPCYS64 (Example 3).

Figure 25:
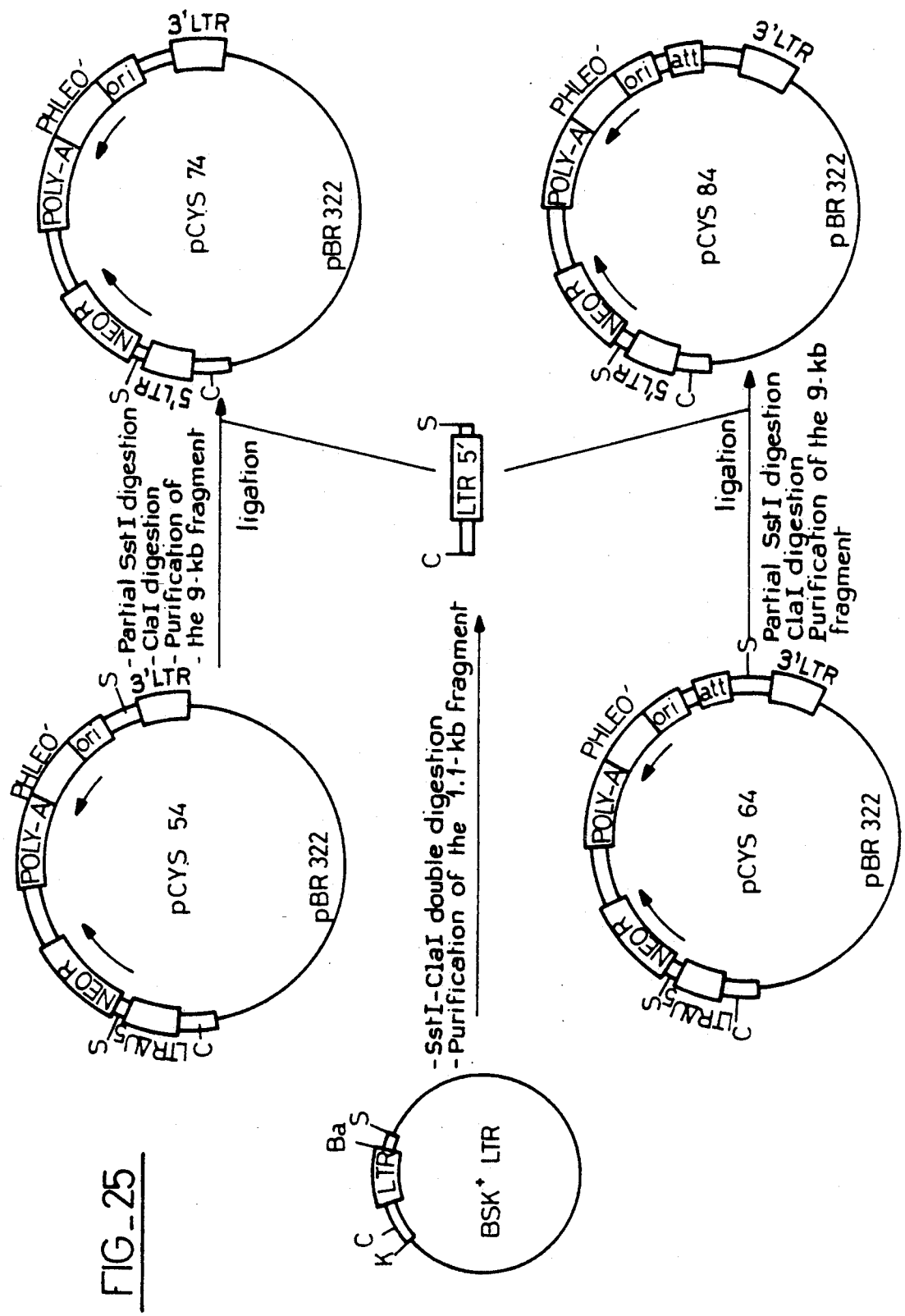

FIG. 25 shows the construction of plasmid pCYS84.

Figure 26:
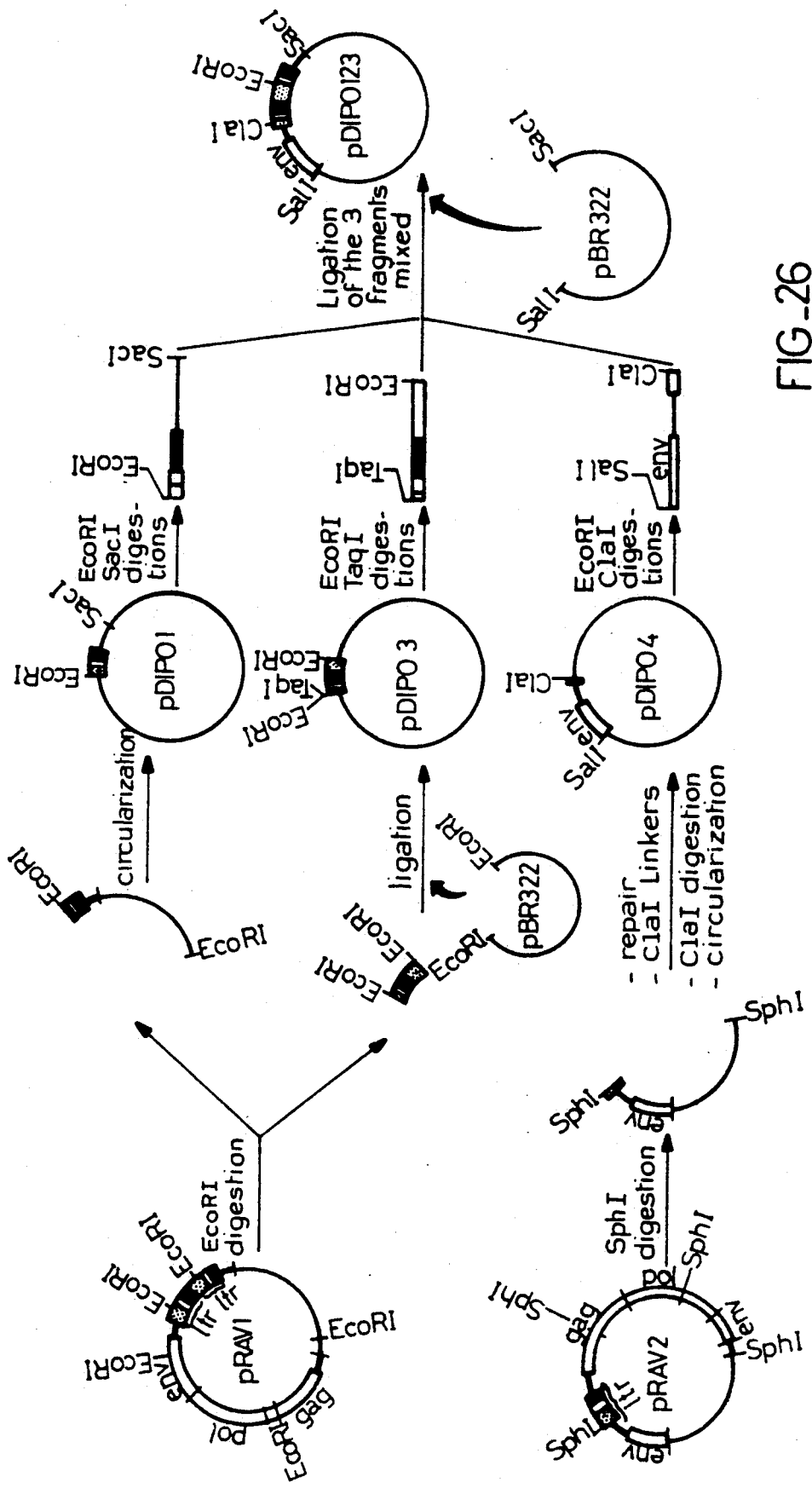

FIG. 26 shows the construction of the clone pDIPO 123 transporting the promoter of the defective vector pHF 13. The fragments shown after the different digestions are obtained by separation on agarose gel followed by electroelution.

▮ U5, ▭ R, ▩ U3,

▭ coding sequence of the retroviral genes,

▮ non-coding retroviral sequence.

——— pBR 322.

Figure 27:
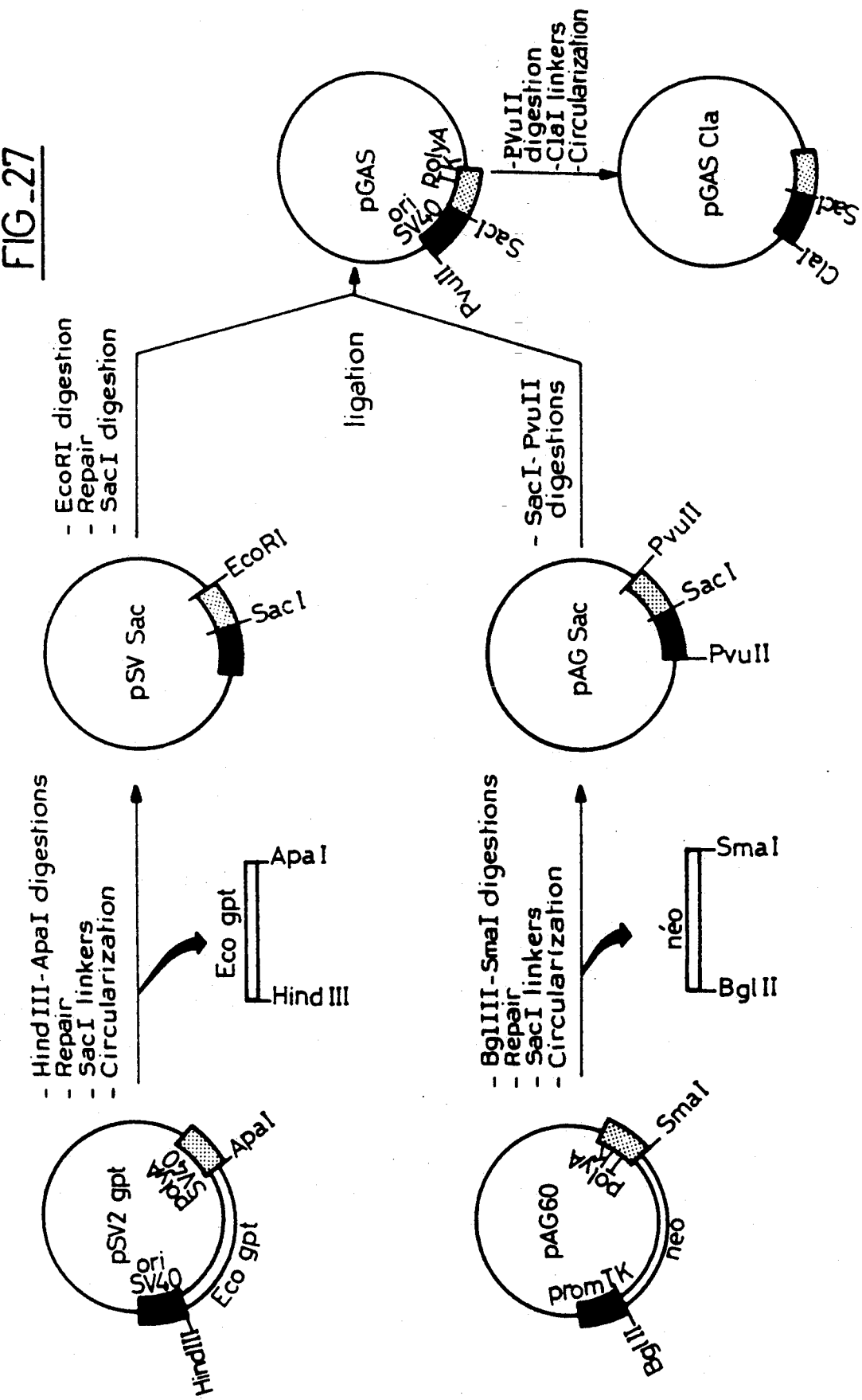

FIG. 27 shows the construction of the clone pGAS-Cla transporting the polyadenylation signal of the defective helper pHF 13. The fragments shown after the different digestions are obtained by separation on agarose gel followed by electroelution.

▮ Origin of replication of the SV40 virus containing the promoter and enhancer of the early genes. ▭ polyadenylation signal of the early genes of SV40. ▮ of the thymidine kinase gene of the Herpes Simplex I virus, ▭ polyadenylation signal of the thymidine kinase gene of the Herpes Simplex I virus.

Figure 28:
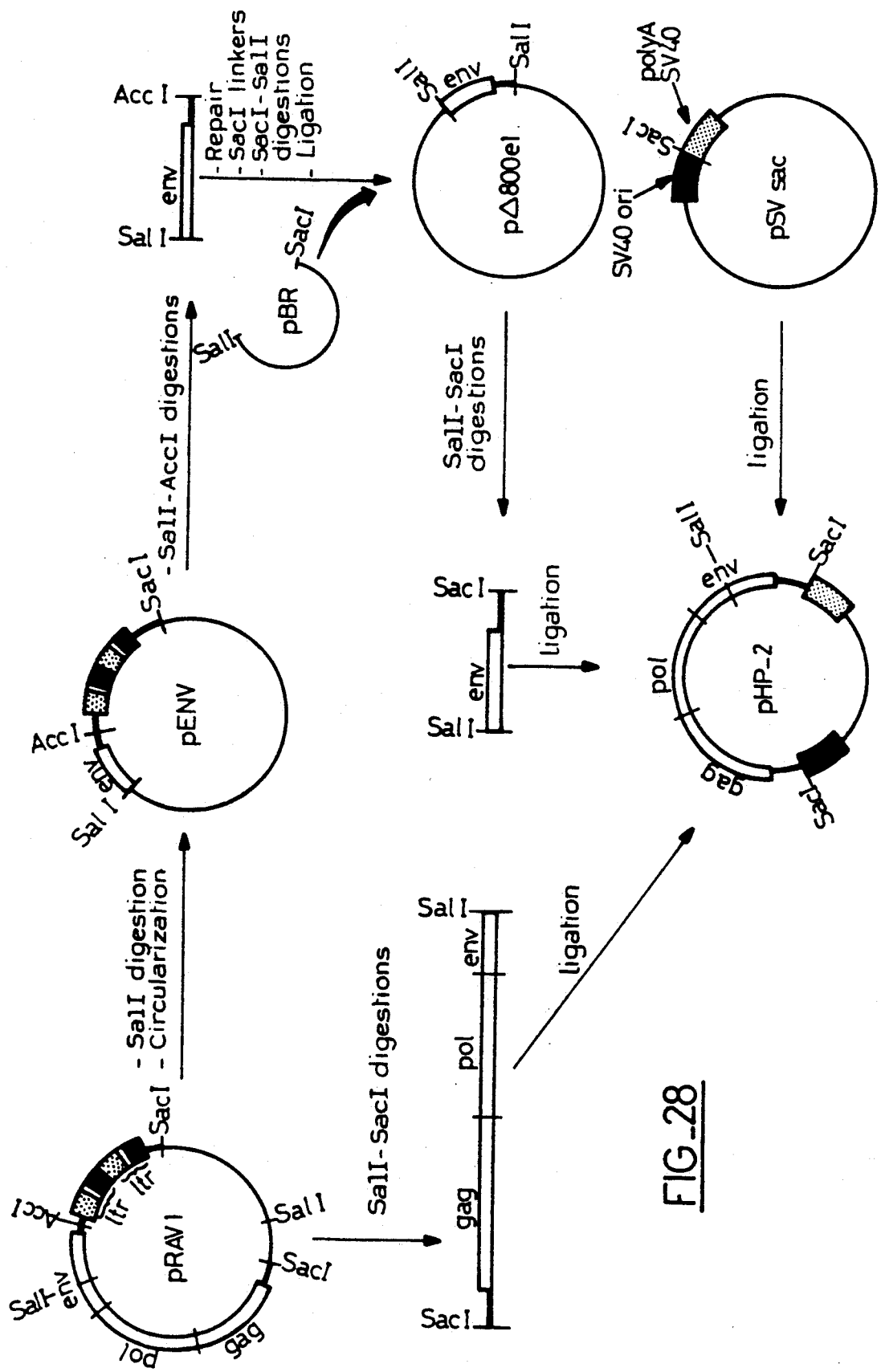

FIG. 28 shows the construction of the clone pHP2 transporting the gag-pol-env genes under the transcriptional control of the promoter of the early genes of SV40. The fragments shown after the different digestions are obtained by separation on agarose gel followed by electroelution.

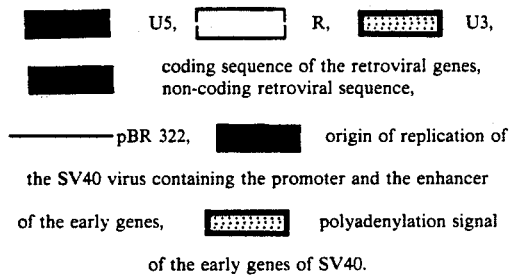

Figure 29:
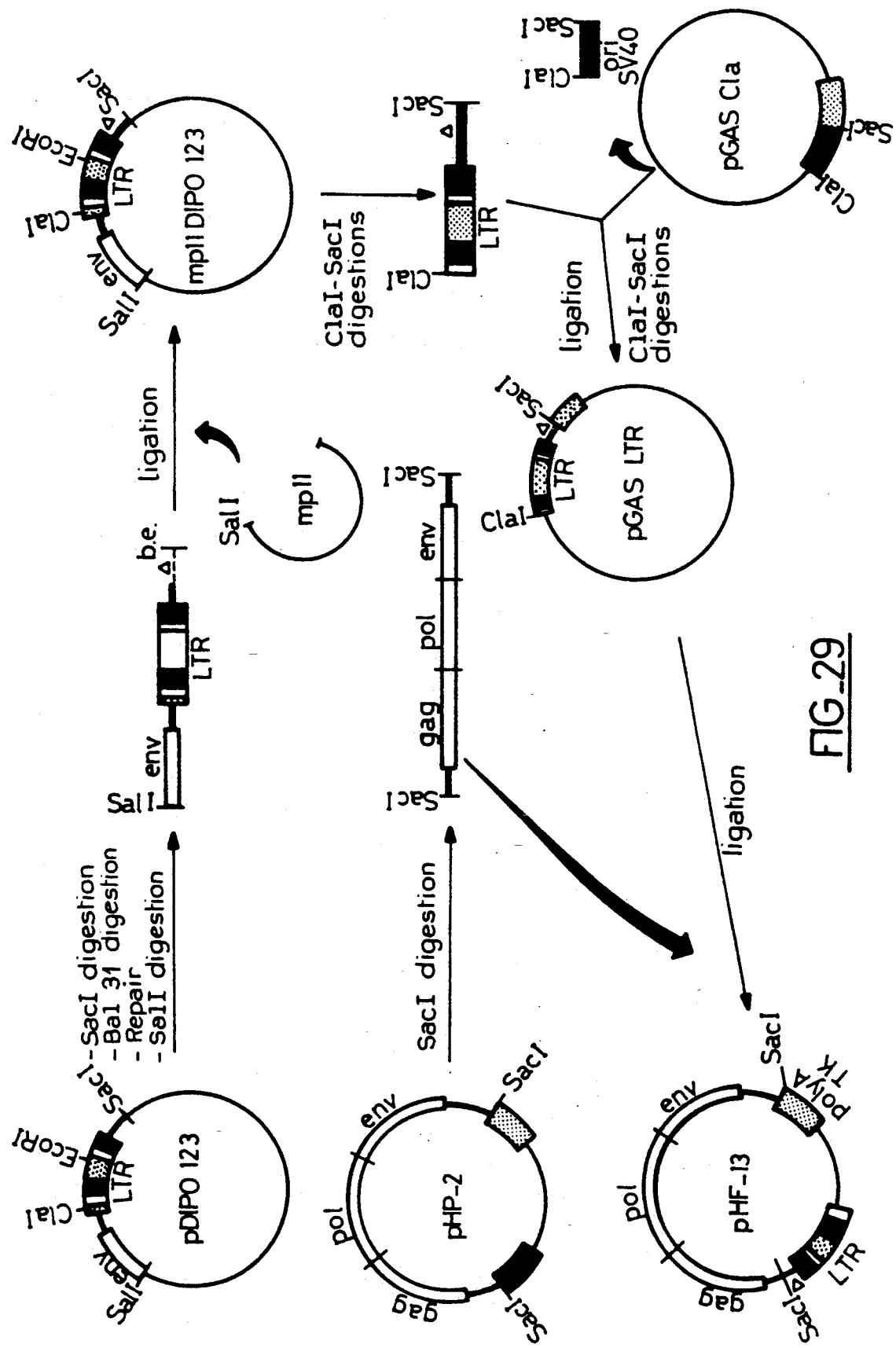

FIG. 29 shows the deletion of the encapsidation sequence and assembly of the clone pHF 13. The fragments shown after the different digestions are obtained by separation on agarose gel followed by elecotroelution.

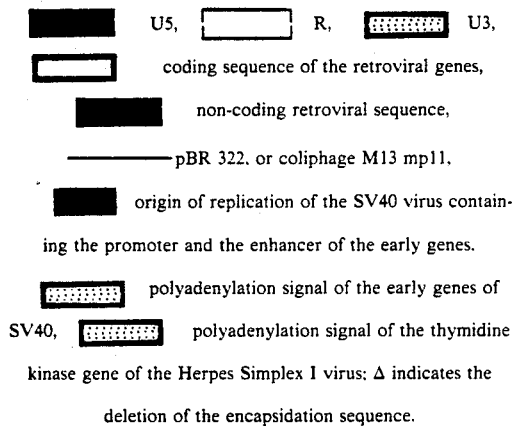

FIG. 30 shows the structure of the RAV-12 genome compared with that of pHF 13.
A - Map of the genes and main structures involved in the functioning of the helper.
B - Detailed map of the promoter region of pHF 13.
C - Description of the deletion of the encapsidation sequence in the pHF 13 genome. Bold characters: deleted sequence, bold italic characters: encapsidation sequence.

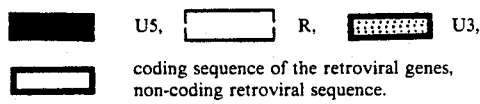

FIG. 31 shows the structure and functioning of the various helper vectors constructed.

The boxes represent the structure of the different genomes. The latter are shown with the associated transcribed and matured RNAs (continuous lines) and polypeptides translated (heavy dashes)
  ds and as are the splicing donor and acceptor sites.
  ∇ and ∇ represent the translation initiation and terminator codons.

Figure 32:
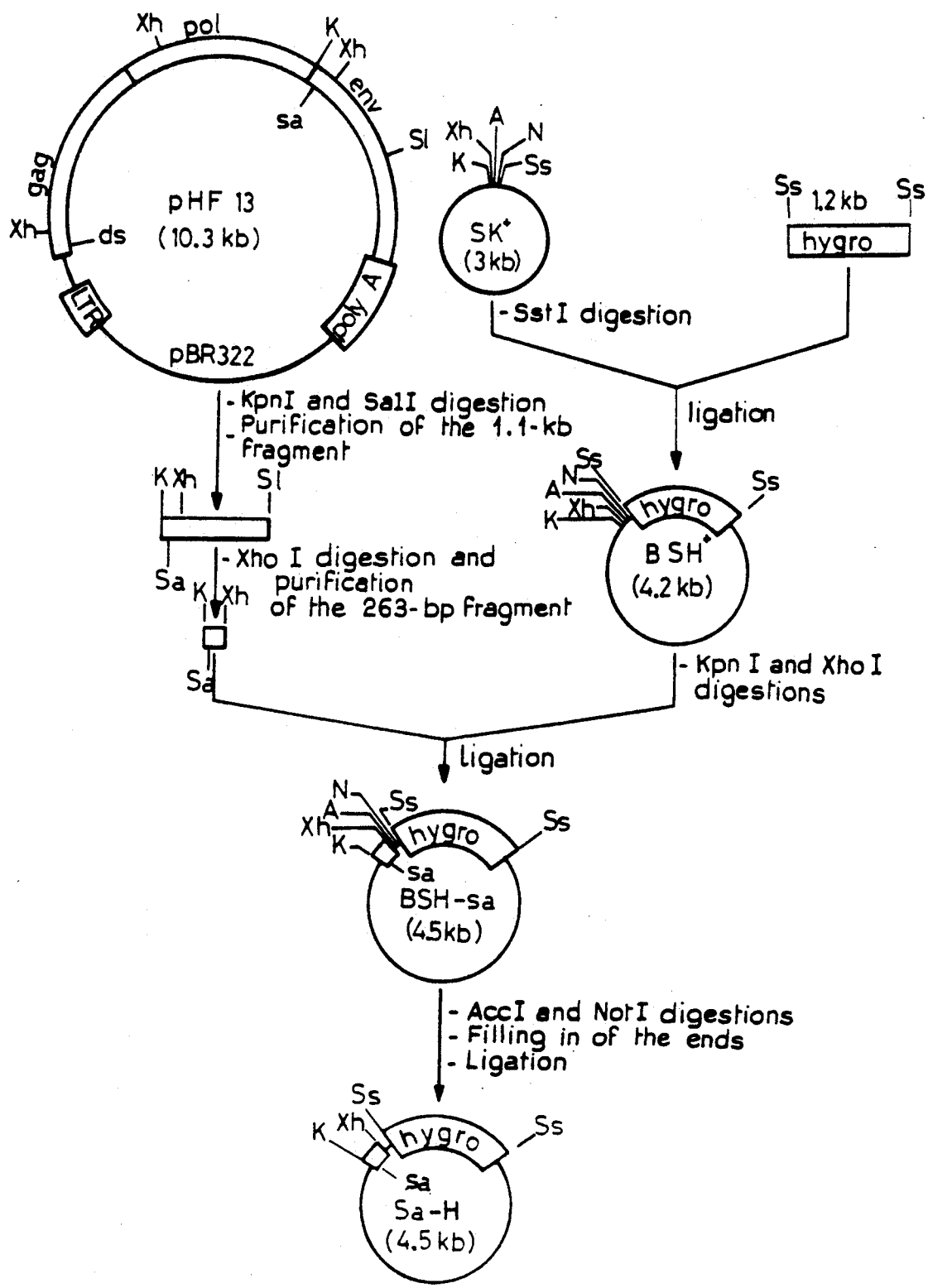

FIG. 32 shows the construction of plasmid Sa-H.

In this figure and in those which follow, the following abbreviations are used:

ds and sa are the splicing donor and acceptor sites.
Kb and bp: kilobase pairs and base pairs.
| A | AccI, | Bs | BstEII, | B | BamHI, | C | ClaI, |
|---|---|---|---|---|---|---|---|
| E | EcoRI, | k | kpnI, | H | HindIII, | Hp | HpaI, |
| N | NotI, | P | PVUII, | Sl | SalI, | Sp | SphI, |
| Sm | SmaI, | Ss | SstI, | St | StvI, | Xb | XbaI, |
| Xh | XhoI, | Nr | NARI. | | | | |

Figure 33:
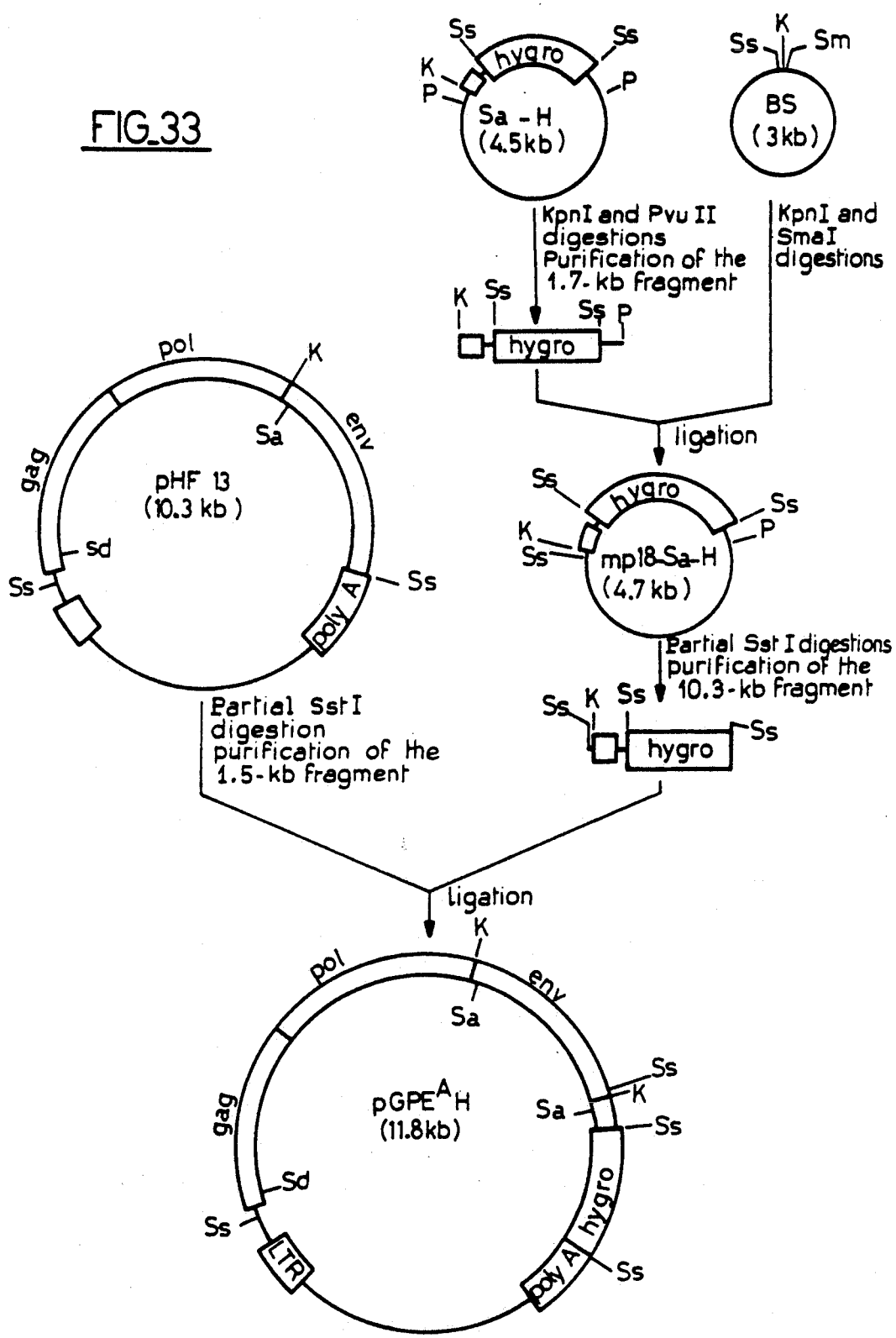

FIG. 33 shows the construction of the helper vector pGPEM.

Figure 34:
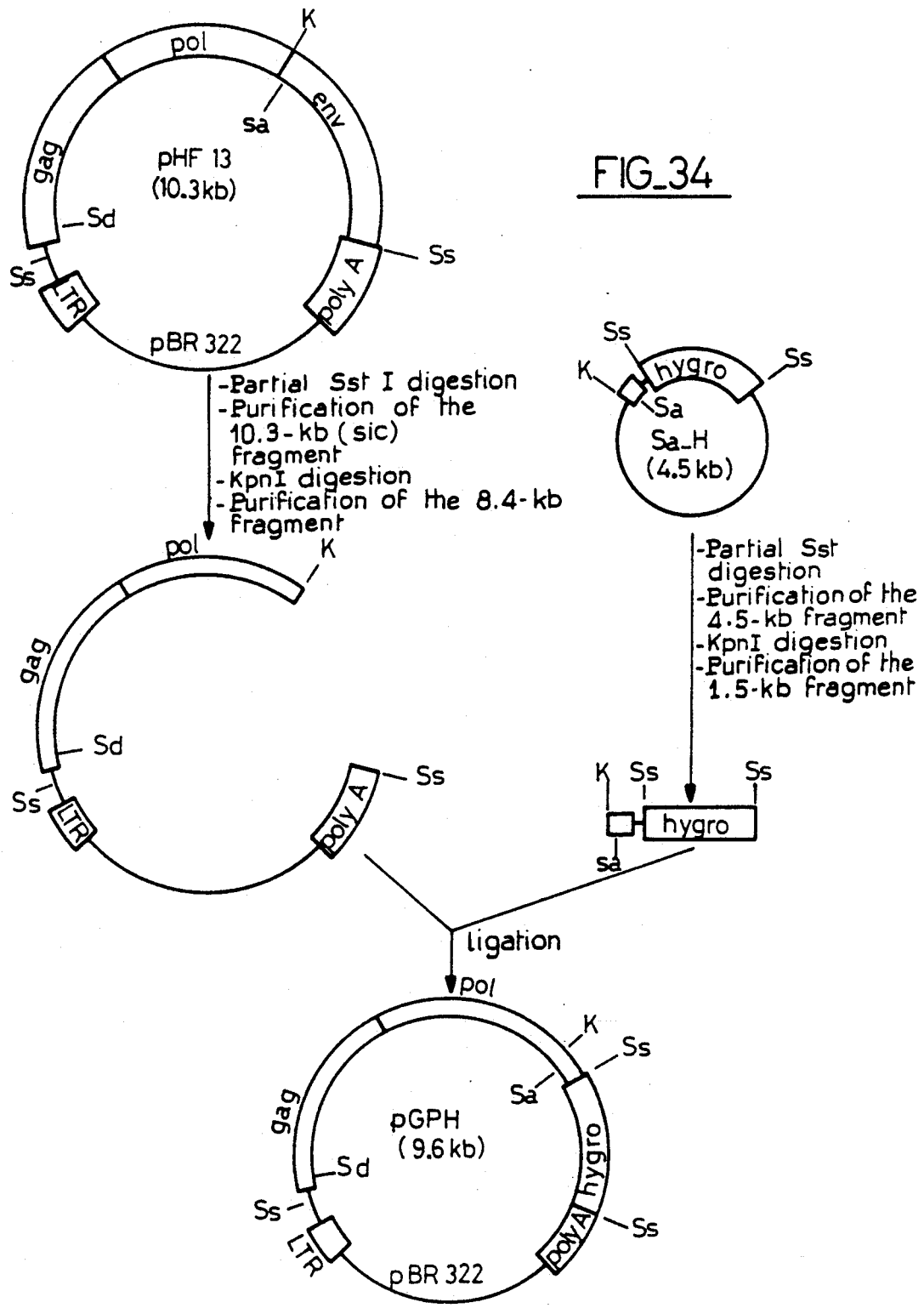

FIG. 34 shows the construction of the helper return pGPH.

Figure 35:
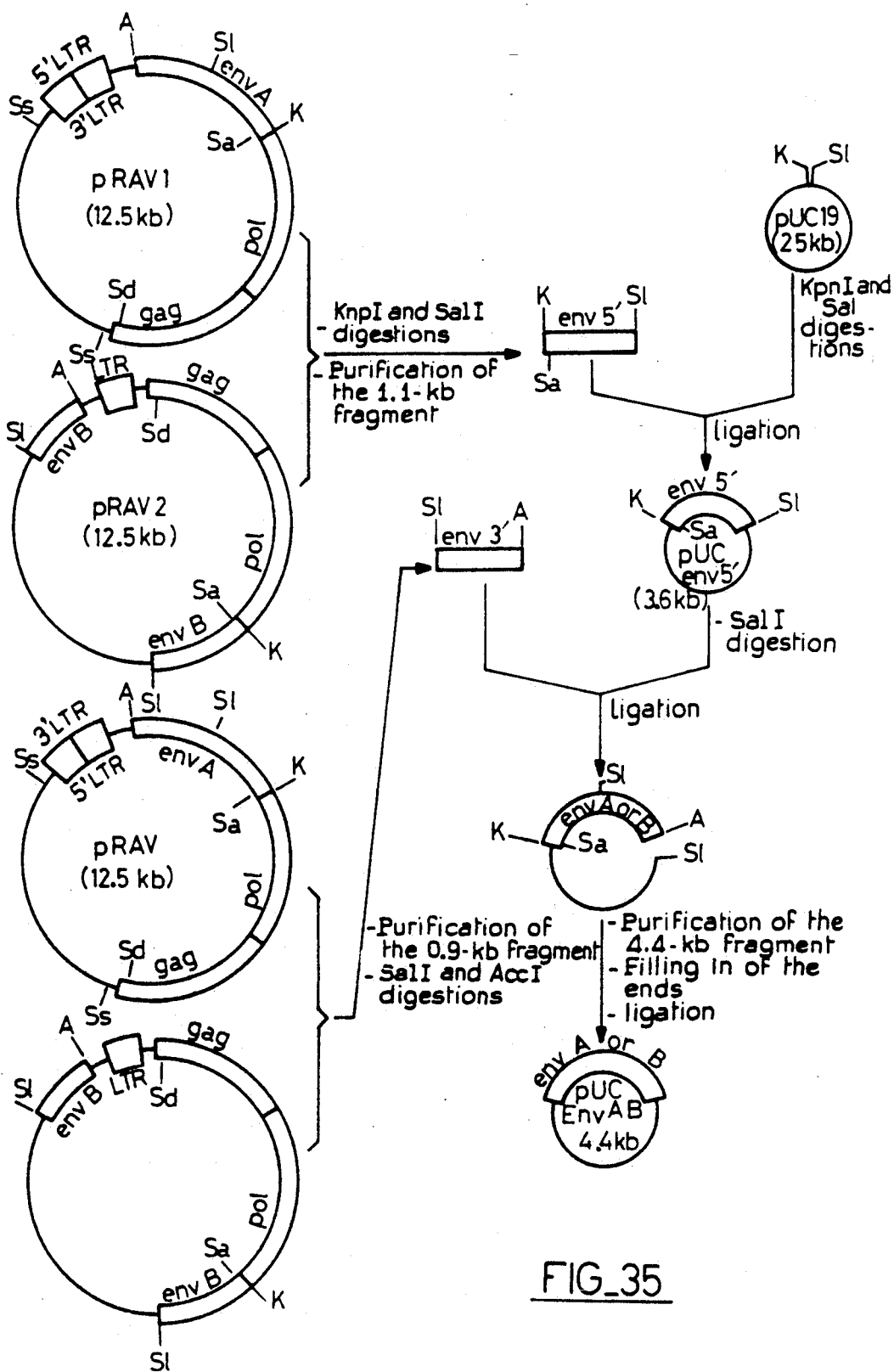

FIG. 35 shows the construction of plasmids pUC Env A and puc Env B.

Figure 36:
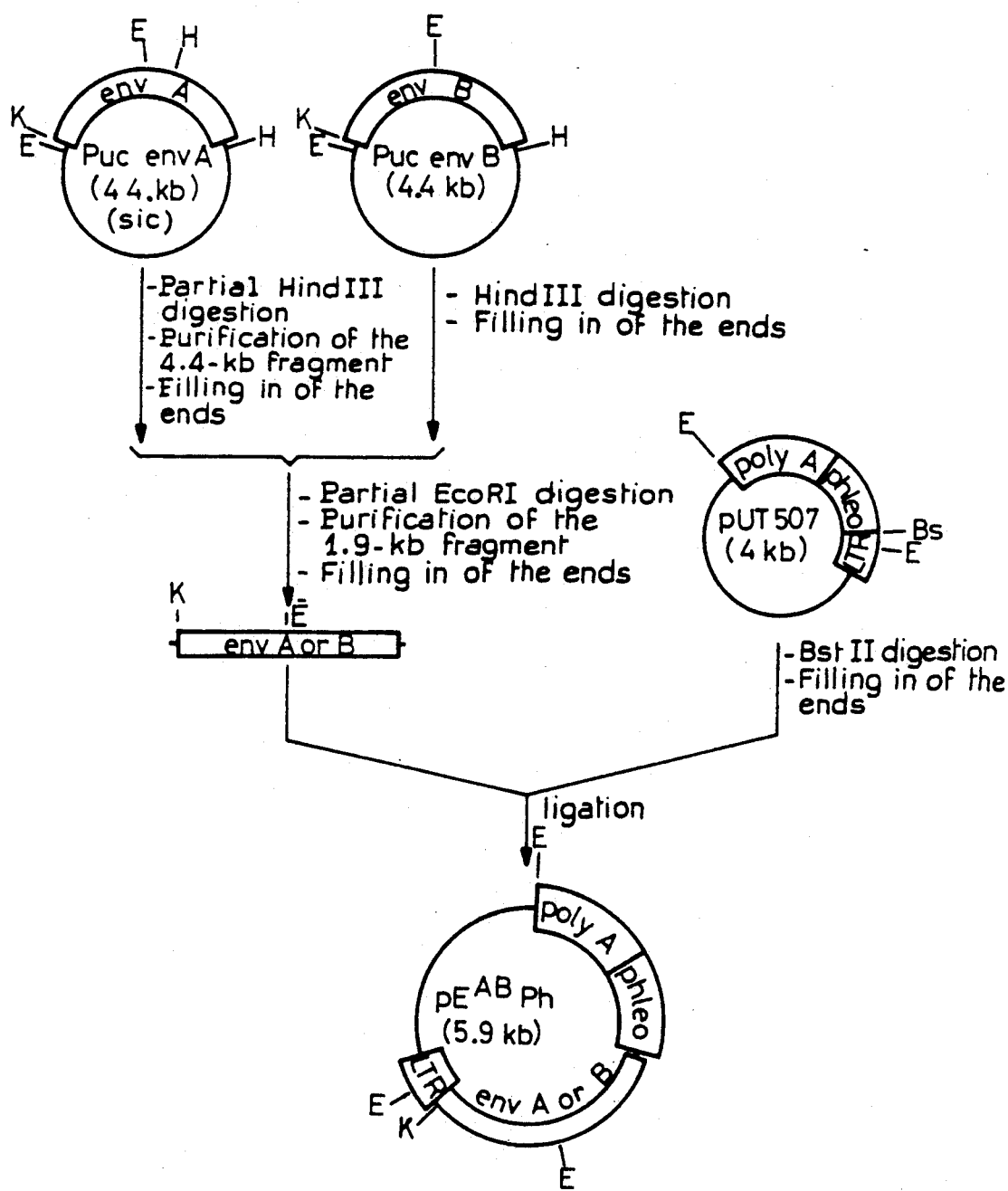

FIG. 36 shows the construction of the helper vectors p.E$^A$:pA and pUC.Env B pA.

Figure 38:
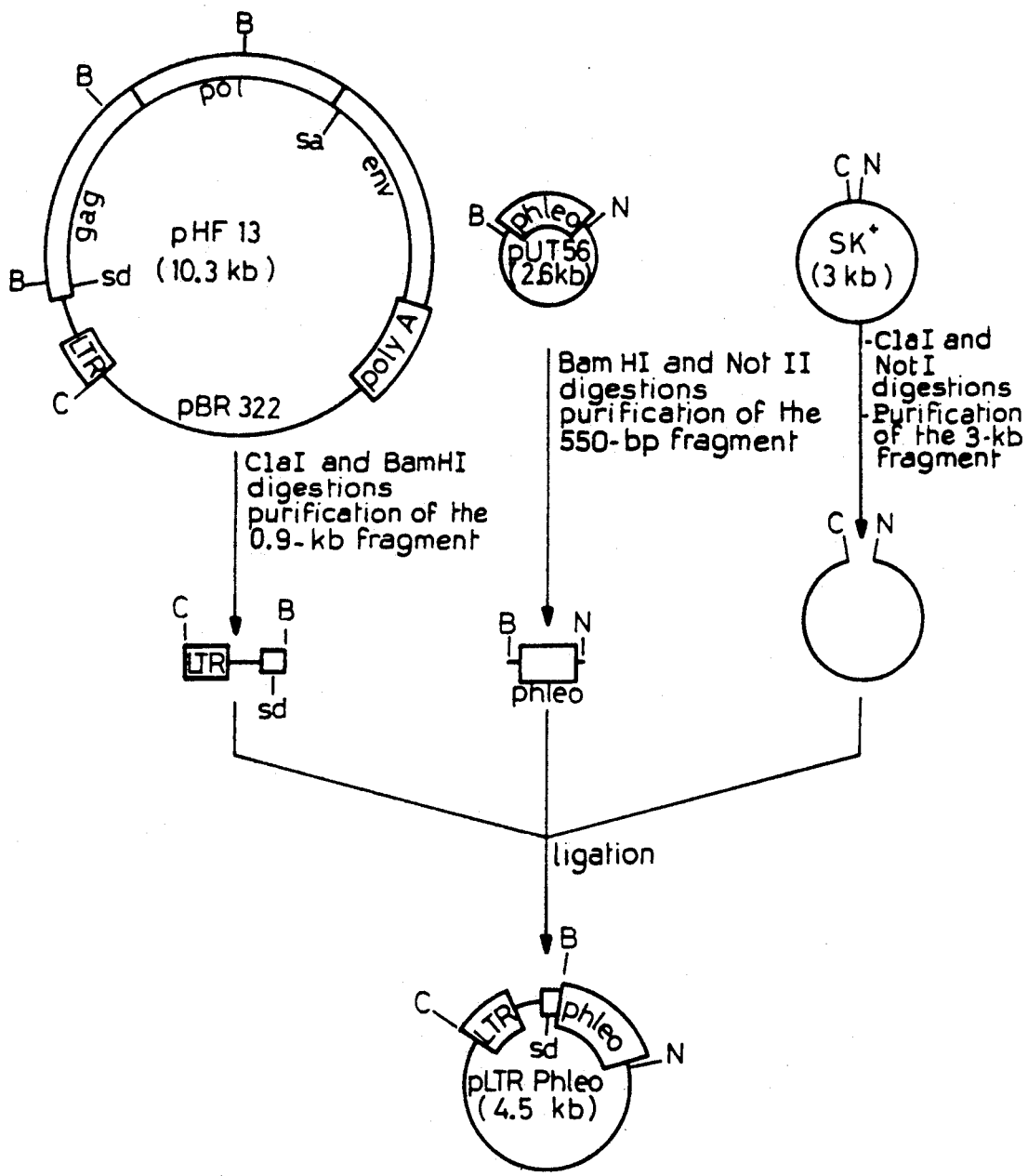

FIG. 38 shows the construction of plasmid pLTR-pHleo.

Figure 39:
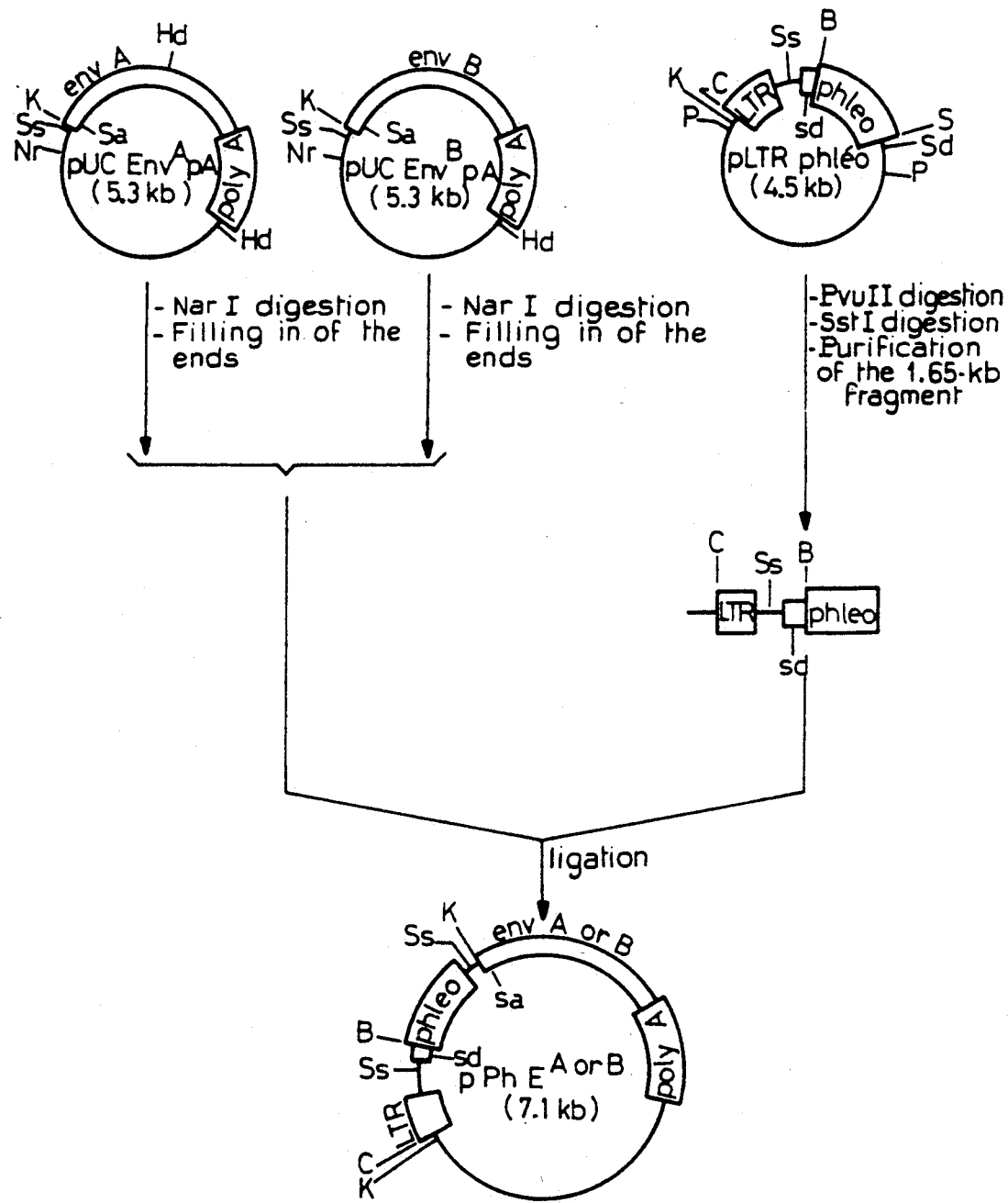

FIG. 39 shows the construction of the helper vectors p.Ph.E$^A$ and pPh.E$^B$.

Figure 40:
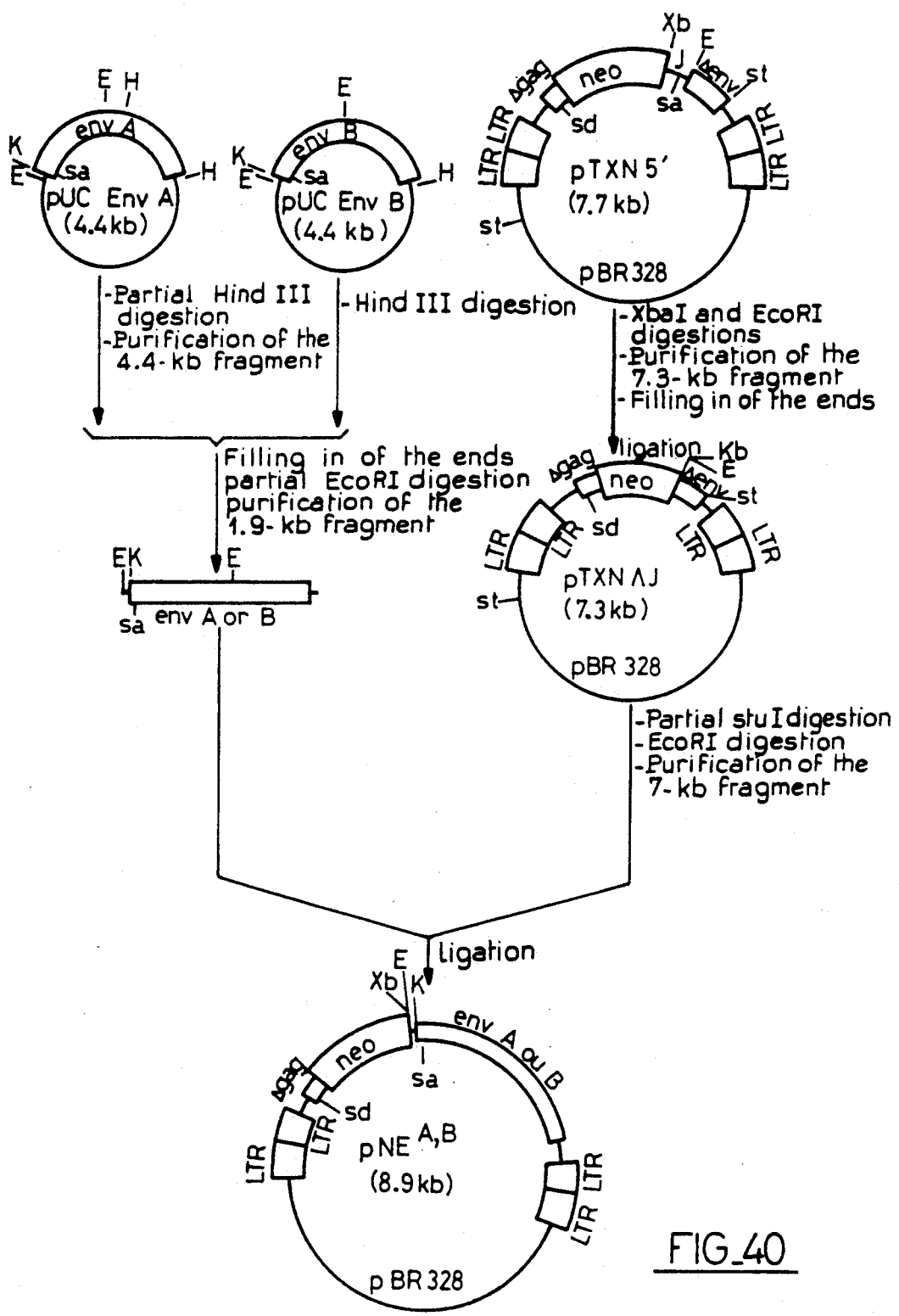

FIG. 40 shows the construction of the retroviral vectors pNE$^A$ and pNE$^B$.

EXAMPLE 1

Production of vectors transporting a single gene

Figure 2:
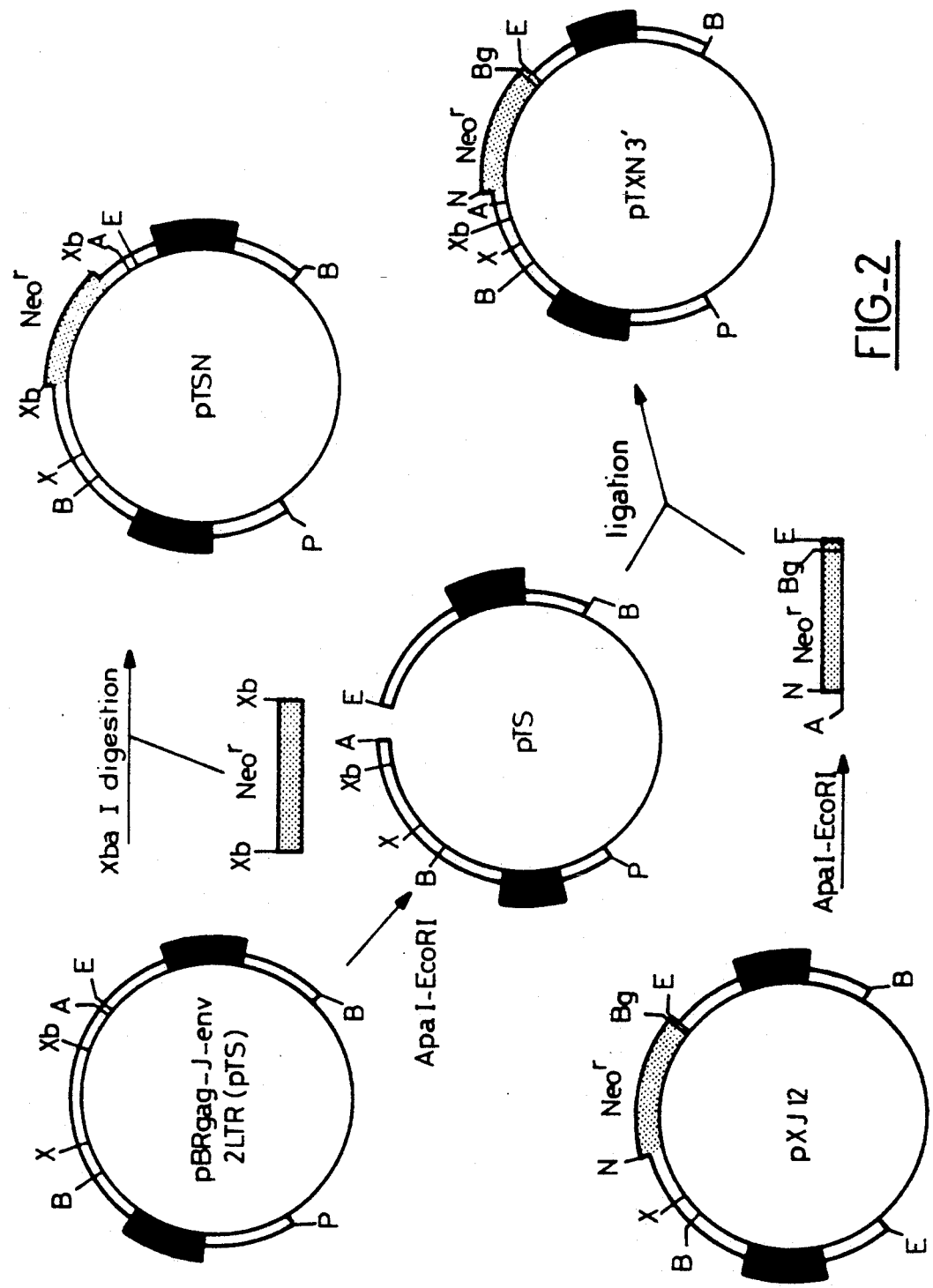

1) Preparation of the clone pTSN (FIG. 2)

The clone pTSN is prepared from the clone pBRgag-J-env2LTR (pTS) which contains the AEV genome relieved of its oncogenic sequences (see Patent No. 85 4019999). The gene coding for neomycin phosphotransferase II (Neo), derived from the transposon Tn5, is provided with XbaI linkers at its ends. It is inserted by ligation into the vector pTS previously linearized after digestion with the enzyme XbaI.

The Neo gene is inserted in the same direction as the direction of transcription of the viral genes. The AUG of the Neo gene is located 803 nucleotides from the AUG of the gag gene, and is not in the same reading frame as the latter (FIG. 5).

2) Preparation of the clone pTXN3' (FIG. 2)

The clone pTXN3' is derived from both clones pTS and pXJ12 (see Patent No. 85 4019999).

The clones pTS and pxJ12 are successively digested with the enzymes ApaI and EcoRI. The 1.2-kb fragment, derived from the clone pXJI2 after digestion and containing the Neo gene, is purified by electroelution after separation on agarose gel. This fragment is then cloned into the previously digested vector pTS to form the clone pTXN3'.

The clone pTXN3' possesses the characteristics of the two clones from which it is derived:
  like the clone pTS, it is devoid of oncogenic sequences and possesses a single XbaI cloning site at the 3' end of the gag sequence.
  like the clone pXJ12' it contains the Neo gene in the 3' position (in place of the v-erb-B gene). The AUG of this gene is located, after splicing of the genomic RNA, 33 nucleotides from the AUG of the gag gene, and is in the same reading frame as the latter (FIG. 5).

Figure 3:
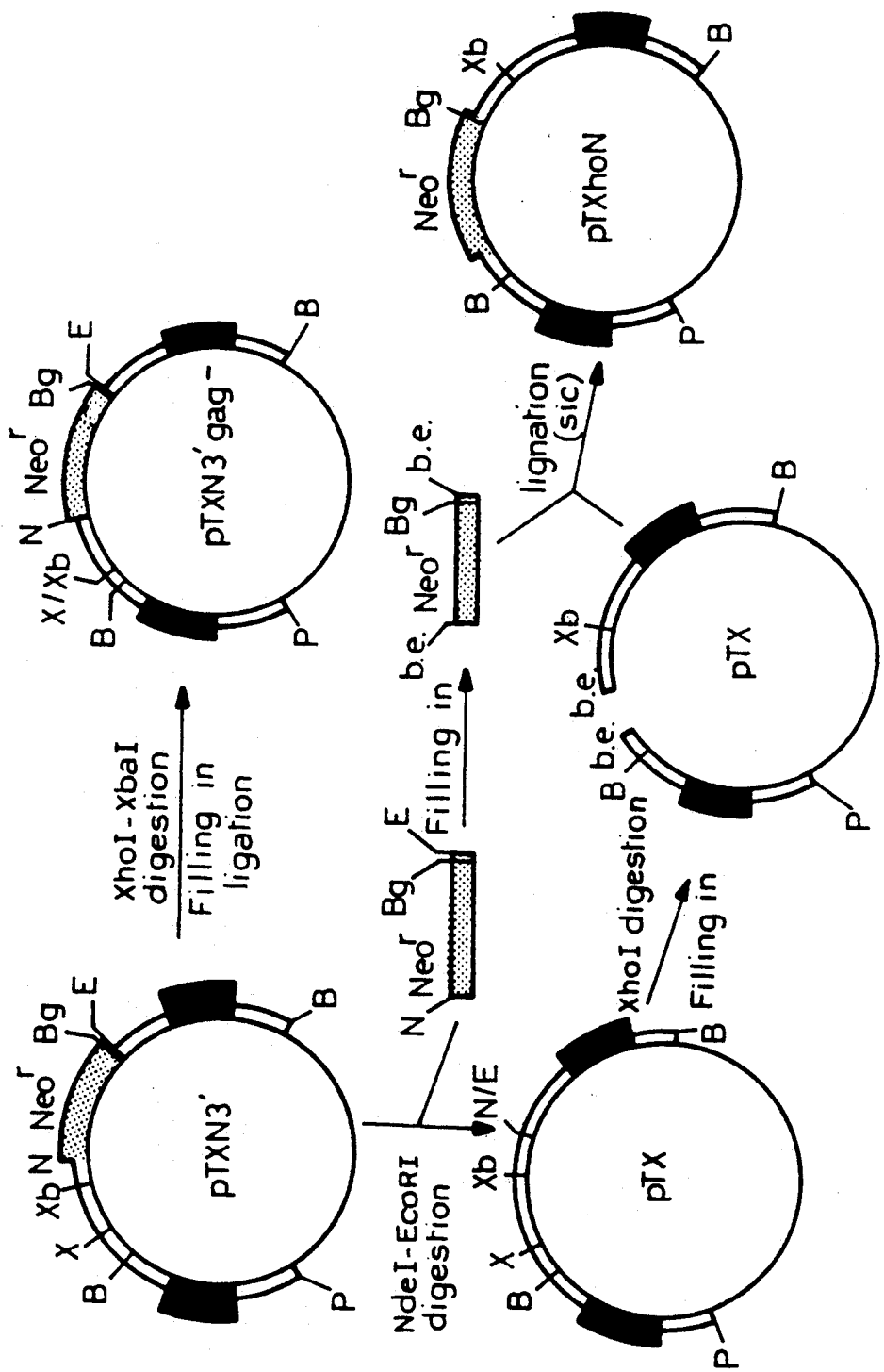

3) Preparation of the clone pTXN3'gag- (FIG. 3)

The clone pTXN3'gag- is directly derived from the clone pTXN3' (section 2, FIG. 2).

The clonepTXN3' is digested successively with the enzymes XhoI and XbaI. The ends thereby obtained are repaired with DNA polymerase I so-called Klenow fragment (Klenow polymerase). The vector is then purified by electroelution after separation on agarose gel, and religated. The clone pTXN3'gag- obtained has thereby been subjected to a deletion of approximately 600 nucleotides from the 3'-terminal portion of the gag gene. 4) Preparation of the clone pTXhoN (FIG. 3)

The clone pTXN3' (section 2, FIG. 2) is successively digested with the enzymes NdeI and EcoRI. The ends obtained are repaired with Klenow polymerase. The fragments are then purified by electroelution after separation on agarose gel.

The fragment corresponding to the vector is religated with itself to form the clone pTX. This clone pTX is digested with the enzyme XhoI and its ends are repaired with Klenow polymerase.

The fragment corresponding to the Neor gene is cloned into the clone pTX to form the clone pTXhoN.

In the clone pTXhoN, the Neo gene is oriented in the same direction as the direction of transcription of the viral genes. The AUG of the Neo gene is located 255 nucleotides from the AUG of the gag gene, and is not in the same reading frame as the latter (FIG. 3).

Figure 4:
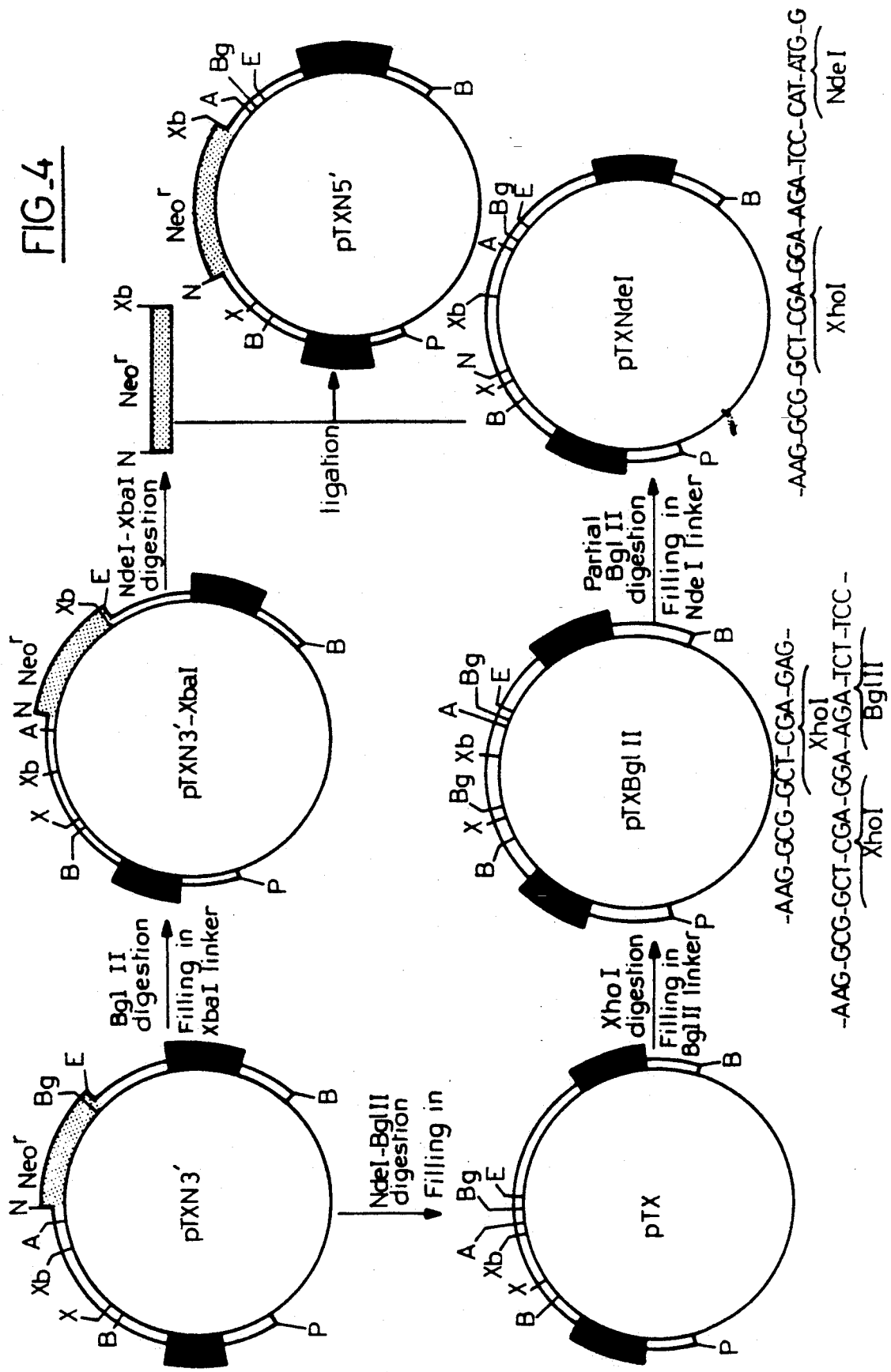

5) Preparation of the clone pTXN5° (FIG. 4)

The clone pTXN3' (section 2, FIG. 2) is linearized after digestion with the enzyme BglII. After repair of the ends with Klenow polymerase, the clone is ligated in the presence of XbaI linkers to form the clone pTXN3'Xba.

The clone pTXN3' Xba is successively digested with the enzyme NdeI and partially digested with the enzyme XbaI. The fragment corresponding to the Neo gene is purified by electroelution after separation on agarose gel.

The clone pTXN3' is digested successively with the enzymes NdeI and BglII. The ends are repaired with Klenow polymerase and religated to form the clone pTX. It may be noted that this operation re-forms the BglII site, the NdeI site being destroyed.

The clone pTX is then linearized after digestion with the enzyme XhoI. The ends are repaired with Klenow polymerase. The clone is then religated in the presence of BglII linkers (the exact sequence of which is shown in FIG. 4) to form the clone pTXBglII. This clone is subjected to a further digestion with the enzyme BglII to remove the excess linker, and religated It may be noted that the addition of a BglII linker to the previously repaired XhoI site recreates the XhoI site.

The clone pTXBglII is, in its turn, linearized after digestion with the enzyme BglII. The ends are repaired with Klenow polymerase The clone is religated in the presence of NdeI linkers (the exact sequence of which is shown in FIG. 4) to for the clone pTXNde. This operation destroys the BglII site. The excess NdeI linkers is removed by further digestion.

The clone pTXNde is successively digested with the enzymes XbaI and NdeI. It is then ligated with the NdeI-XbaI fragment, corresponding to the Neo gene previously isolated from the clone pTXN3'Xba, to form the clone pTXN5'.

The clone pTXN5' thus contains:
the Neo gene in the 5'-position (in place of the v-erb-A gene).
two single EcoRI and BglII cloning sites in the 3' position (in place of the v-erb-B gene).

The Neor gene is situated in the same direction as the direction of transcription of the viral genes. The AUG of the Neo gene is located 267 nucleotides from the AUG of the gag gene and is in the same reading frame as the latter (FIG. 5).

The different constructions carried out were transfected into CEF in culture. Cells expressing the neoR gene are selected in the presence of G148. An initial provision of helper virus enables vector viral particles to be obtained in the culture supernatant. These particles were used for infecting other fibroblasts which, in their turn, become resistant to the selection antibiotic. The cell proteins are then extracted and the neomycin phosphotransferase activity assayed. The first results may be stated as follows:

1. maximal activity is obtained when the NeoR gene is inserted in the same reading frame as that of the oncogene it replaces (production of gag-neo fusion proteins; vectors TXN5', XJ12, TXN3' and TXN3'gag-);
2. to obtain the production of a neomycin phosphotransferase protein whose translation is initiated at the AUG belonging to the neoR gene, the latter was inserted in a different reading frame from that of the oncogene it replaces. Under these conditions, the neomycin phosphotransferase activity detected is relatively low when the gene is in the erbB position (XJ1); this activity is below the threshold of sensitivity of the method when the gene is placed in the erb-A position (TXhoN and TSN). Although very low, this activity is sufficient to endow these cells with resistance to G418;
3. deletion of the 3'-terminal portion of the residue of the gag gene reduces the neomycin phosphotransferase activity by a factor of 2 (compare TXN3' with TXN3'gag-). In RSV, this region contains an enhancer type sequence. The observed effect might hence exterted by a transcriptional mechanism. The presence of the erb-A gene in the vector leads to a doubling in the amount of enzymes produced. This effect is possibly linked to stimulatory action of this gene on cell multiplication.

EXAMPLE 2

Vector transporting two genes in the v-erbA and v-erbB position, respectively

The NeoR bacterial gene coding for neomycin phosphotransferase is present in all these two-gene vectors; it is placed either in the position of the v-erbA oncogene or in the position of the v-erbB oncogene.

In the unoccupied position, we placed:
Lac7 bacterial gene coding for E. coli beta-galactosidase (used as a model gene for expression); this is the case with the vectors pNL35, pNL35AUG, pNLnls35' pNL53gpt and pNL53P,
the CGH gene coding for avian growth hormone (in the case of the vector pNcGH),
the Δ gag-Vmyc fusion gene (in the case of the vector pMN53),
the genes coding for the p53 protein of murine or avian origin (p5355, p5396, p53P4 and p53P2),
the env gene coding for the viral envelope protein (pN.E$^A$ and pNE$^B$)

Figure 6:
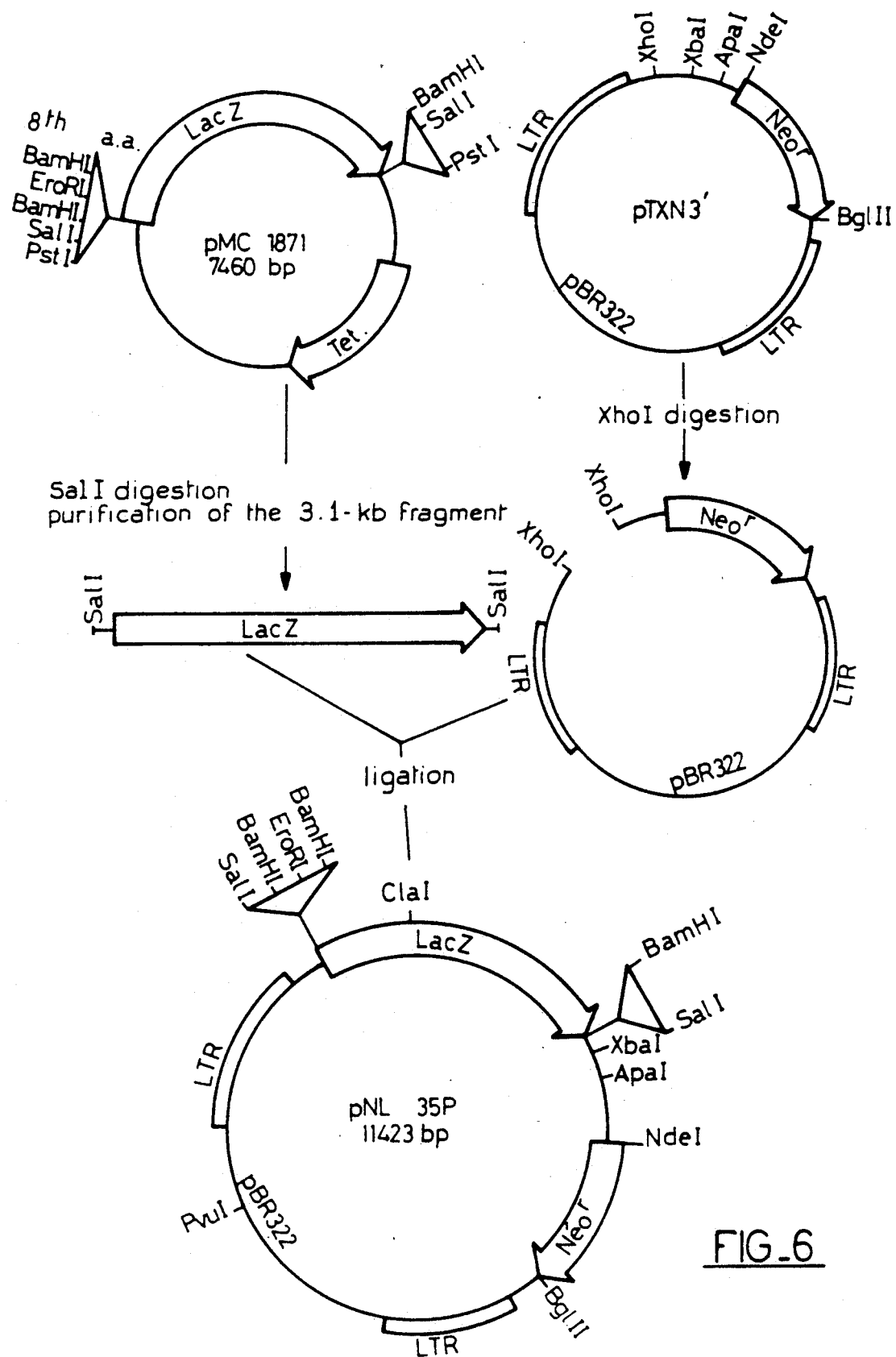

1) The vector pNL35 (FIG. 6)

This is derived from pTXN3' described in FIG. 2. The DNA of the clone pTXN3' was linearized with the endonuclease XhoI in the single site located in the delta-gag sequence of the vector (FIG. 6).

The lacZ gene is isolated from plasmid pMC 1871 (FIG. 6) by digestion with the enzyme SalI. The 3.1-kb fragment is purified on agarose gel and then inserted into the XhoI site of pTXN3'; the XhoI and >SalI ends are compatible and lead to recreation of the SalI sites.

This results in the vector pNL 35 (FIG. 6).

Property of the vector pNL 35.

In addition to the properties of the vector pTXN3' reported in section 1-A-2, this vector carries:

the Lac Z gene at the 5' end of the J sequence; this gene is expressed in the form of a fusion protein from the AUG of the retroviral gag gene.

the delta-Gag-LacZ fusion protein is functional in chick cells (CEF), since the enzyme activity, which is reflected in a blue coloration in the presence of X-Gal (5-bromo-4 chloro-3-indolyl-β-D-galactopyranoside), was visualized in cells which received this vector.

this vector enables the functioning of 2 genes simultaneously, the gene coding for resistance to neomycin (cells cultured on a medium containing G 418 continue to grow) and the gene coding for beta-galactosidase, the activity of which is detected by the blue coloration of the cells in the presence of X-Gal, to be detected and studied.

Figure 7:
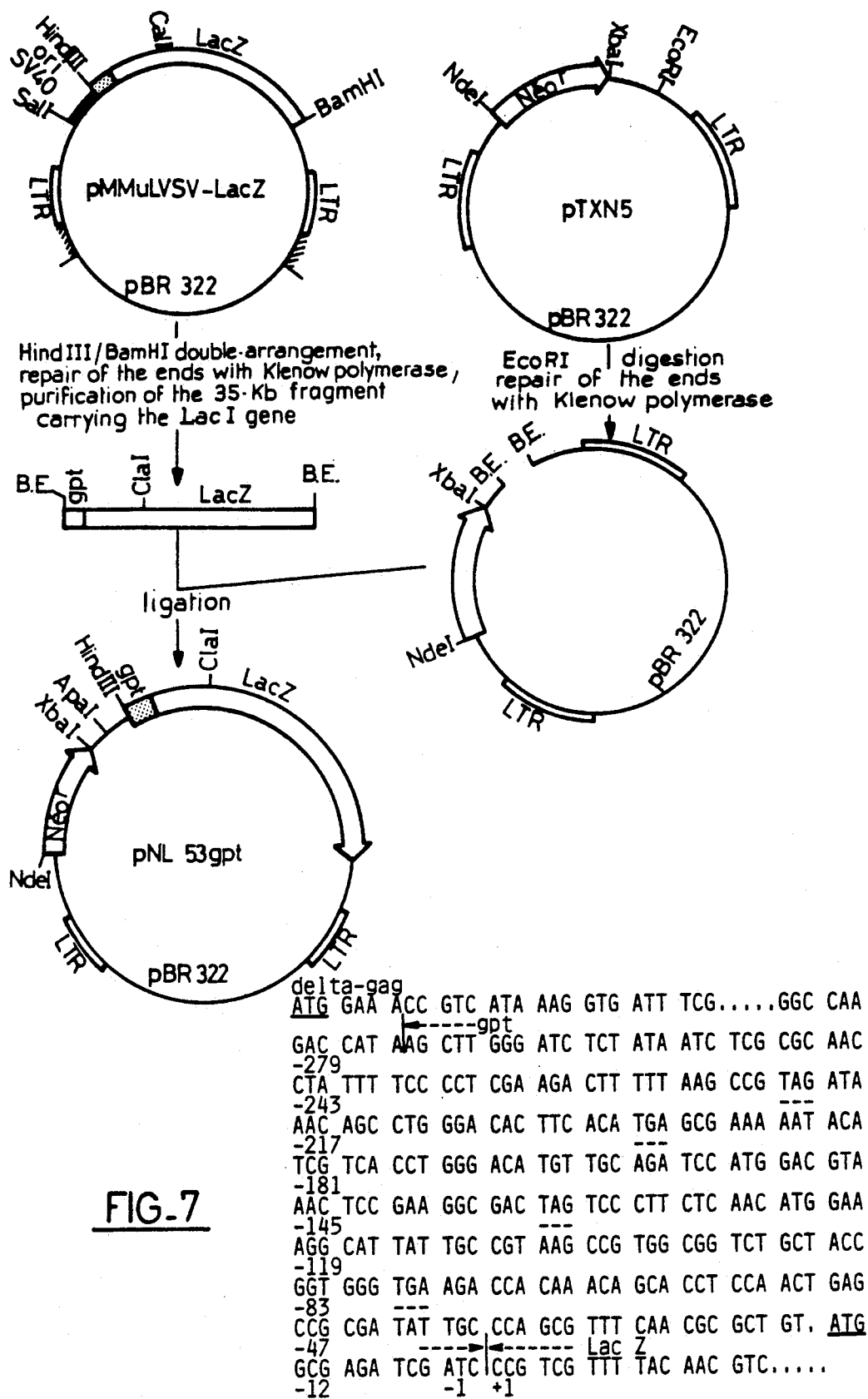

2) Vector pNL 53 (FIG. 7)

This is derived from vector pTXN5' described in FIG. 4.

The vector pTXN5' was linearized with the enzyme EcoRI and the ends were repaired with Klenow polymerase to obtain blunt ends.

Plasmid pMMuLVSV LacZ (obtained from J. F. Nicholas (Sanes J. S. et al. 1986, EMBO J.5; 3133–3142)) carries the 3.5-kb LacZ bacterial gene bounded by the HindIII and BamHI sites in the genome of the mouse MMuLV retrovirus This LacZ gene includes approximately 280 bp of the gpt gene in its 5' portion.

This plasmid is doubly digested with BamHI and HindIII, the 3.5-kb LacZ fragment is purified on an agarose gel and the ends are repaired with Klenow polymerase This fragment is inserted into the vector pTXN5' prepared as described above.

This results in the vector pNL 53.

Properties of the vector pNL 53.

In addition to the properties of the vector pTXN5', this vector, like the vector pNL 35, at the potential for expressing 2 genes: Neo and LacZ.

The LacZ gene can be expressed from the AUG carried by the sequence of the gpt gene at position −15 (FIG. 7). This AUG is in the same reading frame as the sequence of LacZ gene.

The functional protein encoded by the LacZ gene is not a fusion protein in this case, since translation initiated at the delta-gag AUG must be stopped by one of the 4 termination codons (TAG, TGA, TGA and TGA) located in the sequence of the gpt gene, placed upstream from the LacZ gene (FIG. 7).

3) In addition to the vectors already mentioned in this example, that is to say the vectors pNL 35 and pNL 53, we constructed other vectors which may be classified in 3 groups, the 3rd group consisting of a special case of 2-gene vectors.

a) 1st group:

These are vectors which transport the same genes and the vectors pNL 35 and pNL 53, that is to say the bacterial Neo and LacZ genes.

These vectors are:

pNL 35 AUG, the characteristic of which is: the LacZ gene has its own AUG (which was not the case in the vector pNL 35) in a reading frame different from that of the delta-gag sequence.

pNL 35 AUG P possesses, like the above, the LacZ gene with its own AUG, the latter being in the same reading frame as the AUG of the delta-gag sequence.

pNL 53 P: the sequence of the gpt gene present in the vector pNL 53 gpt has been deleted. The coding sequence of the LacZ gene is placed in the same reading frame as that of the delta-gag sequence.

pNL 53 AUG: identical to the above vector (pNL 53 P) and possesses an AUG initiation codon for the LacZ gene, in a reading frame different from that of the delta-gag sequence.

pNL 53 AUG P: identical to the above vector (pNL 53 AUG), but the AUG initiation codon of the LacZ gene is in the same reading frame as that of the delta-gag sequence.

pNL nls 35: identical to the vector pNL 35, but with the insertion of an additional so-called nls sequence (nuclear localization sequence) upstream from the LacZ gene. This sequence imparts a perinuclear localization to the enzyme produced by the LacZ gene (β-galactosidase), equivalent to a perinuclear blue coloration in the presence of the X-Gal substrate.

b) 2nd group:

These are vectors which transport 2 genes, one of which is the Neor gene.

b.1) - pNcGH: this vector possesses a Neor gene in the position of the v-erbA oncogene, and a gene coding for avian GH (avian growth hormone) in the position of the v-erbB oncogene; this avian cGH gene is represented by the complementary DNA synthesized from the messenger RNAs producing avian GH. This gene was produced by SANOFI-Toulouse.

b.2) - pMN53: this vector possesses a Neor gene in the v-erbB position and a fusion gene composed of the delta-gag sequence and the sequence of the v-myc oncogene derived from the genome of the avian retrovirus MC29 in the v-erbA position.

This vector confers characteristics of perpetuation and cell transformation on the cells which harbour it.

b.3) Vectors transporting the p53 genes: 4 vectors were constructed. They all possess the Neor gene in the v-erbA position and a gene coding for the P53 protein in the v-erbB position These P53 genes are represented by complementary DNAs (cDNAs).

*2 vectors transporting a P53 cDNA of murine origin. They differ in the orientation of this gene, placed in the retroviral direction (p53S5) or in the opposite direction (p53S6).

*2 vectors transporting a P53 cDNA of avian origin. They differ in the orientation of this gene, placed in the retroviral direction (p53P4) or in the opposite direction (p53P2).

These constructions may be used, like the vector pMN53, for purposes of cell perpetuation. The vector p53P4 appears to have a similar effect to the vectors transporting the v-erbA oncogene, that is to say a positive influence on cell multiplication.

b.4) - pN.E: two vectors were constructed, both containing the Neor gene in the position of the v-erbA oncogene (see Example 4–5) B))

In addition, these vectors transport an en v (sic) gene (coding for the retroviral envelope), one being the env gene of subgroup A (pN.E$^A$), the other being the env gene of subgroup B (pN.E$^B$); the splicing acceptor site preceding the env gene has been brought back during the construction with the env gene. This site originates from the RAV virus supplying the env gene, either RAV1 for pN.E$^A$ or RAV2 for pN.E$^B$.

The cells harbouring this vector constitutively expresses (sic) the env gene. This expression leads the cell in question to a retroviral resistance with respect to viruses of the same subgroup. Furthermore, these cells are resistant to neomycin.

c) 3rd group:

A special case of 2-gene vectors:

pE.Ph: Two vectors were constructed, one containing the env gene of subgroup A (pE$^A$Ph), the other the env gene of subgroup B (pE$^B$.Ph)

They both contain, in addition to the env gene, the gene for resistance to phleomycin (Phleo$^R$) downstream from the env gene. In both cases, the splicing acceptor site is absent.

The env and Phleo$^R$ genes are placed under the transcriptional control of the LTR of the RSV retrovirus and of the transcription termination and polyadenylation sequence of the SV40 virus.

a.1) Vector pNL 35 AUG (FIG. 8)

This is derived from vector pTXCN3' described in FIG. 2.

* The vector pTXN3' was linearized with the enzyme xhoI and the ends were repaired with Klenow polymerase to obtain blunt ends.

The linearized vector was digested with the enzyme xbaI which generates cohesive ends. The resulting doubly digested 7857-base pair vector was isolated on agarose gel and purified by electroelution.

* The 7460-base pair vector pMC 1871 described in FIG. 8 was linearized with the enzyme SalI, and the 3,000-base pair fragment carrying the LacZ gene was isolated on agarose gel and purified by electroelution.

* The 2868-base pair vector pUC 19 described in FIG. 8 was linearized with the enzyme SalI. The 3,000-base pair LacZ fragment was inserted into pUC 19. The resulting vector is pUC 19-LacZ, of 5690 base pairs.

* The vector pUC 19 LacZ was linearized with the enzyme HindIII and the ends were repaired with Klenow polymerase to obtain blunt ends.

This linearized vector was digested with the enzyme XbaI. The resulting 3097-base pair fragment was isolated on agarose gel and purified by electroelution. This 3097-base pair fragment carrying the LacZ gene was inserted into the 7857-base pair vector pTXN3'.

This results in the vector pNL 35 AUG (FIG. 8).

Figure 9:
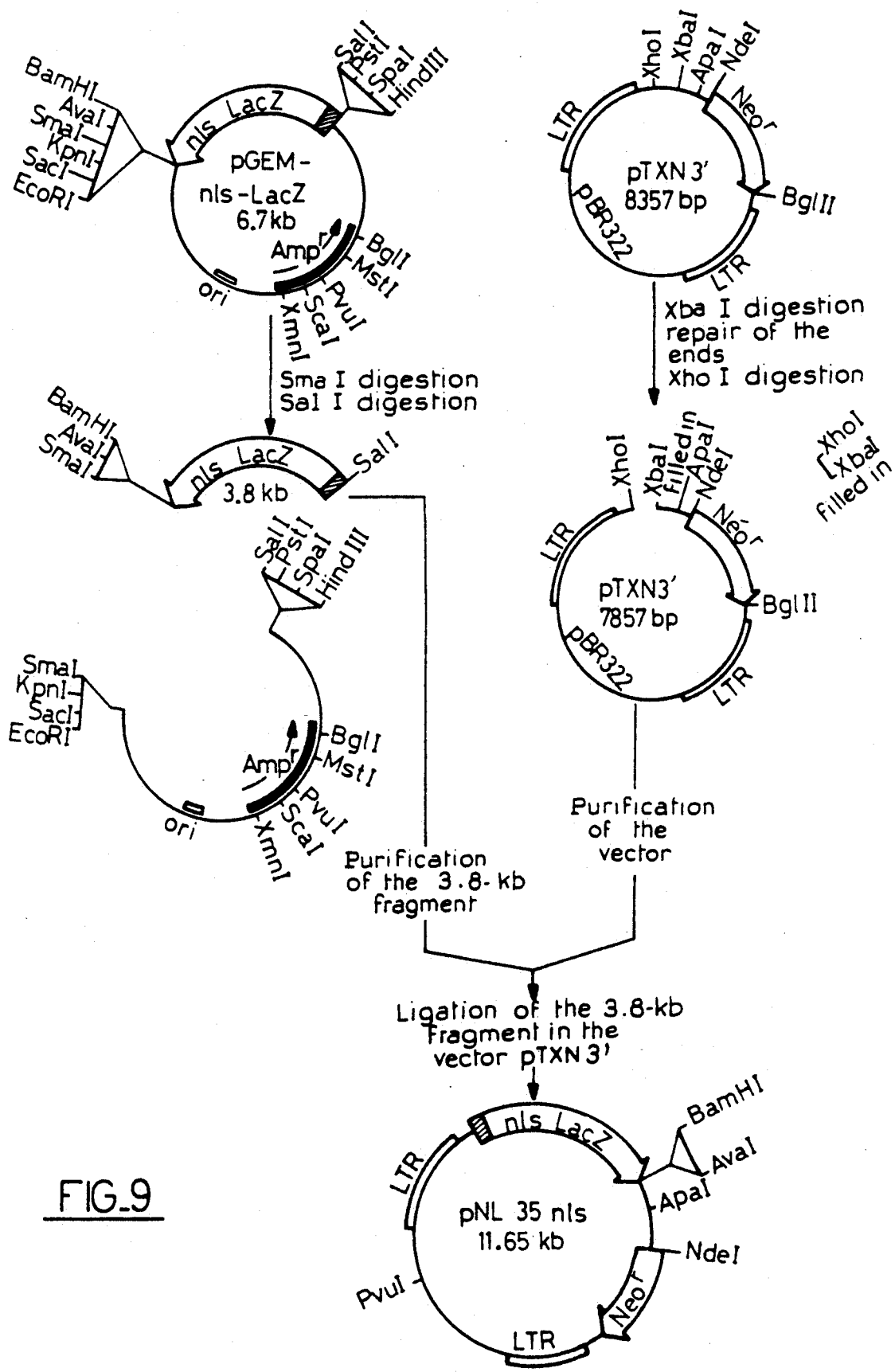
FIG. 9 shows the construction (lacuna) vector pNL 35 nls (Example 2).

In addition to the properties of the vector pNL 35, this vector has the potential for expressing the LacZ gene from an AUG of its own.

a.2) Vector pNL 35 nls (FIG. 9)

* This vector is derived from pTXN3' described in FIG. 2. This vector pTXN3' was linearized with the enzyme XbaI and the ends were repaired with Klenow polymerase to obtain blunt ends. This linearized vector was digested with the enzyme XhoI which generates cohesive ends. The resulting doubly digested 7857-base pair vector was isolated on agarose gel and purified by electroelution.

* The vector pGEM nls LACZ described in FIG. 9 carries the LacZ gene downstream from an nls sequence (nuclear localization sequence). This vector was doubly digested with the enzymes SalI which generates cohesive ends and SmaI which generates blunt ends. The resulting 3.8-kb fragment was isolated on agarose gel and purified by electroelution.

This 3.8-kb fragment was then inserted into the 7857-base pair vector pTXN3'.

This results in the vector pNL 35 nls.

Figure 10:
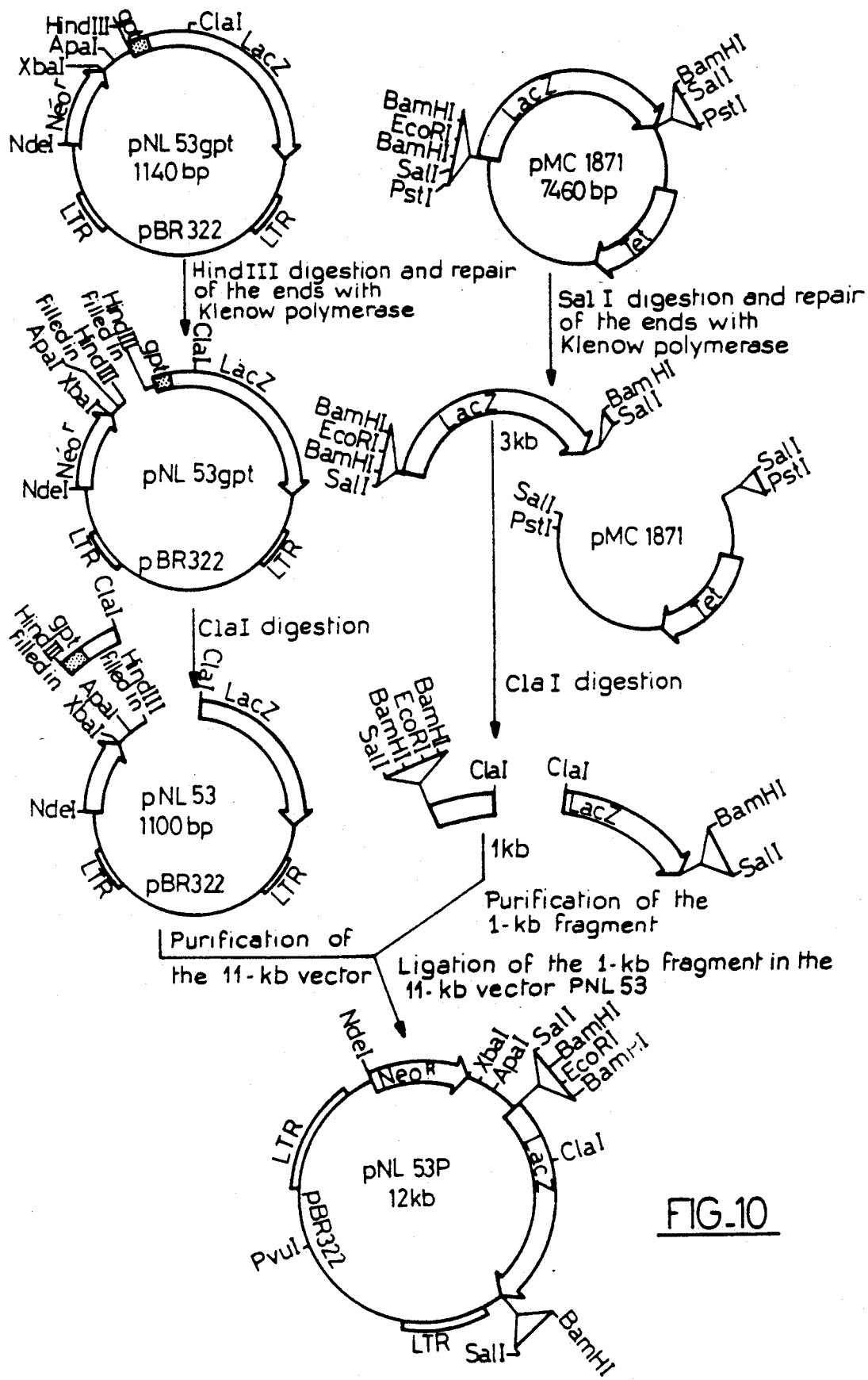
FIG. 10 shows the construction of vector pNL 35 P (Example 2).
Figure 11:
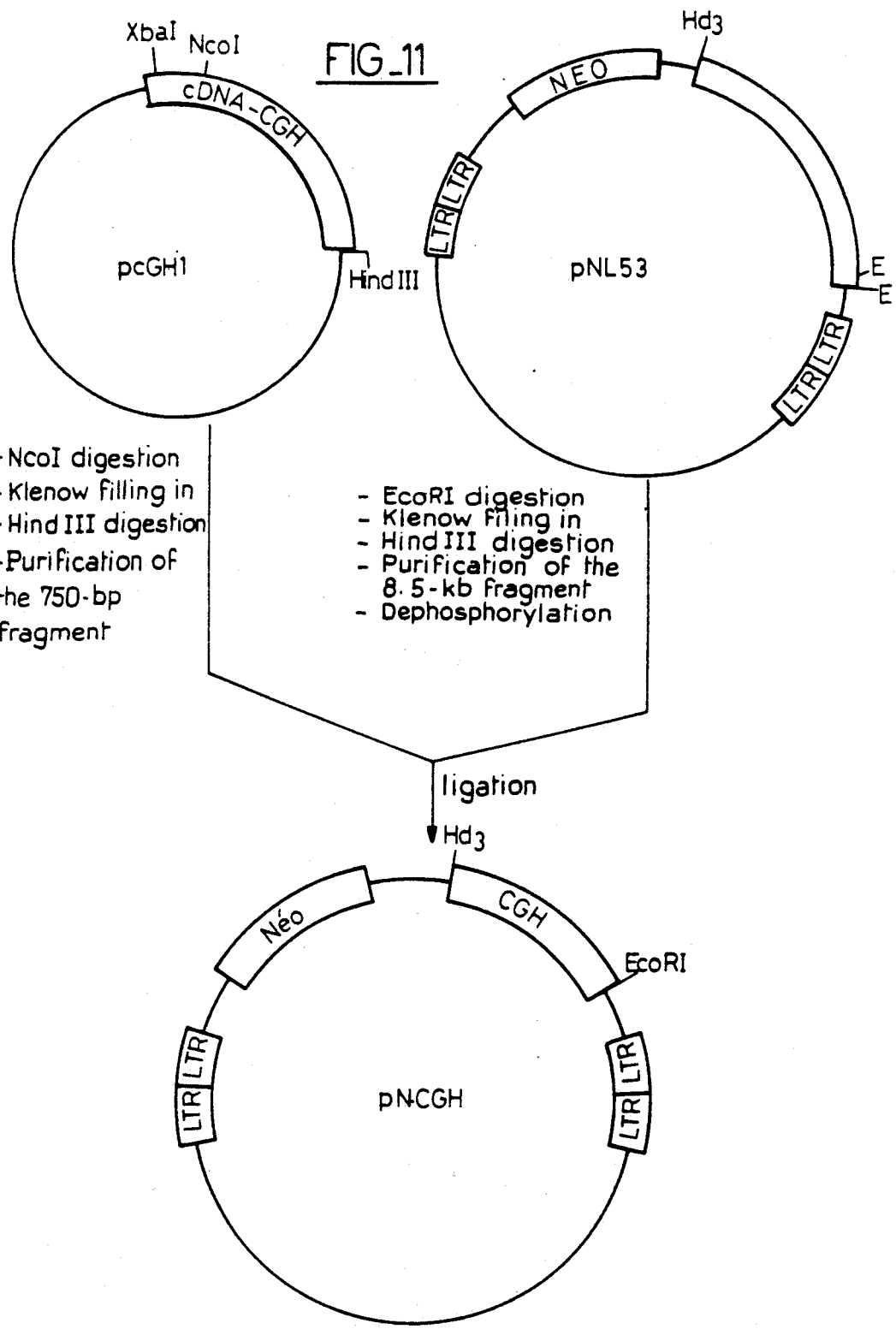
FIG. 11 shows the construction of the vector pNc GH (Example 2).

This vector, in addition to the properties of the vector NL 35, possesses the nls sequence upstream from the LacZ gene. This sequence permits perinuclear localization of the LacZ protein towards the nuclear membrane. Cells which express this vector NL 35 nls display a perinuclear blue coloration after treatment with Xgal, whereas cells which express the vector NL 35 display a cytoplasmic blue coloration after the same treatment with Xgal.

a.3.) The vector pNL 53 P (FIG. 10)

This vector is derived from pNL 53gpt described in FIG. 7.

* The vector pNL 53 gpt was linearized with the enzyme HindIII and the ends were repaired with Klenow polymerase to obtain blunt ends. The resulting vector was then digested with the enzyme ClaI which generates cohesive ends. The resulting 11-kb DNA fragment was isolated on agarose gel and purified by electroelution.

* Plasmid pMC 1871 described in FIG. 8 was linearized with the enzyme SalI and the ends were repaired with Klenow polymerase to obtain blunt ends. The DNA thus treated was then digested with the enzyme ClaI which generates cohesive ends. The resulting 1-kb fragment carrying the 5' portion of the LacZ gene was isolated on agarose gel and purified by electroelution.

The 1-kb fragment was then inserted into the vector pNL 53. This results in the vector pNL 53 P.

Figure 1:
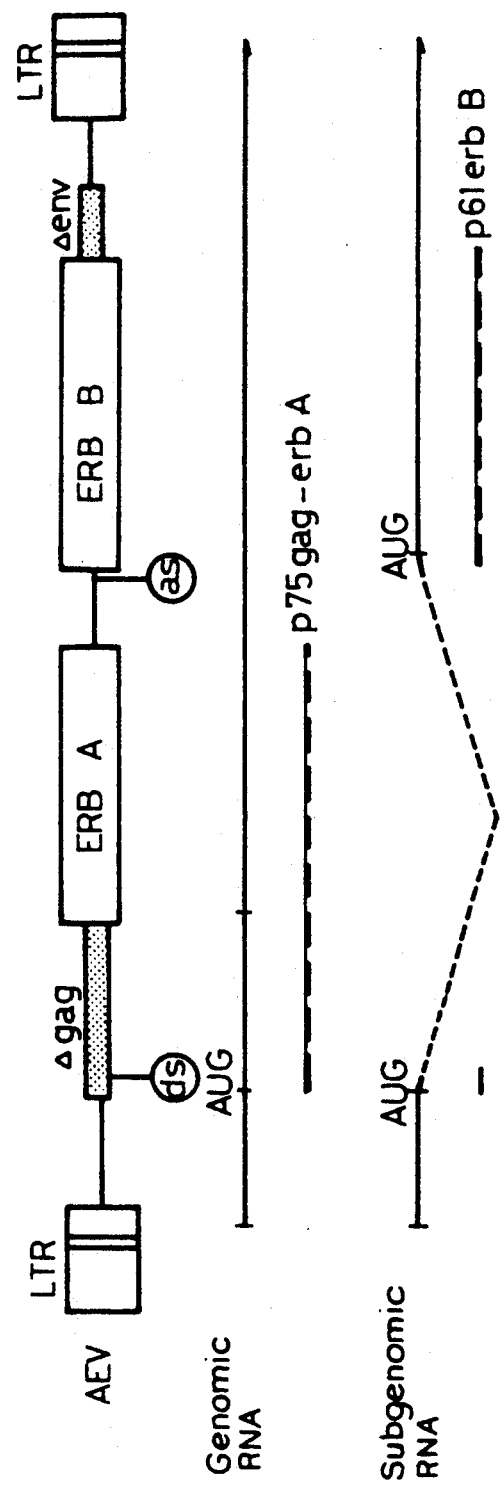

In addition to the properties of the vector pNL 53 gpt, the vector pNL 53 P has the distinctive feature of no longer possessing the gpt sequence, and of expressing the LacZ gene from the AUG of the Δ Gag residue which is in the same reading frame as the sequence of the LacZ gene. The functional protein encoded is a Gag-LacZ fusion protein.

b.1) Construction of the vector pNcGH (FIG. 1)

The 750-bp HindIII-NcoI fragment was isolated from plasmid pCGH1 carrying the complementary DNA of the avian growth hormone gene, and the NcoI end rendered blunt by treatment with Klenow polymerase. This fragment carrying the avian growth hormone gene was inserted between HindIII and EcoRI sites as a replacement for the LacZ gene in the vector pNL 53. The resulting plasmid was referred to as pNcGH. This vector carries the gene for resistance to neomycin in the v-erbA position and the avian growth hormone cGH gene in the v-erbB position The latter carries, in its 5' portion, a stop codon and an initiation codon 19 bp apart from one another. These two codons are in the same reading frame as the AUG of the Δ-gag sequence.

Figure 12:
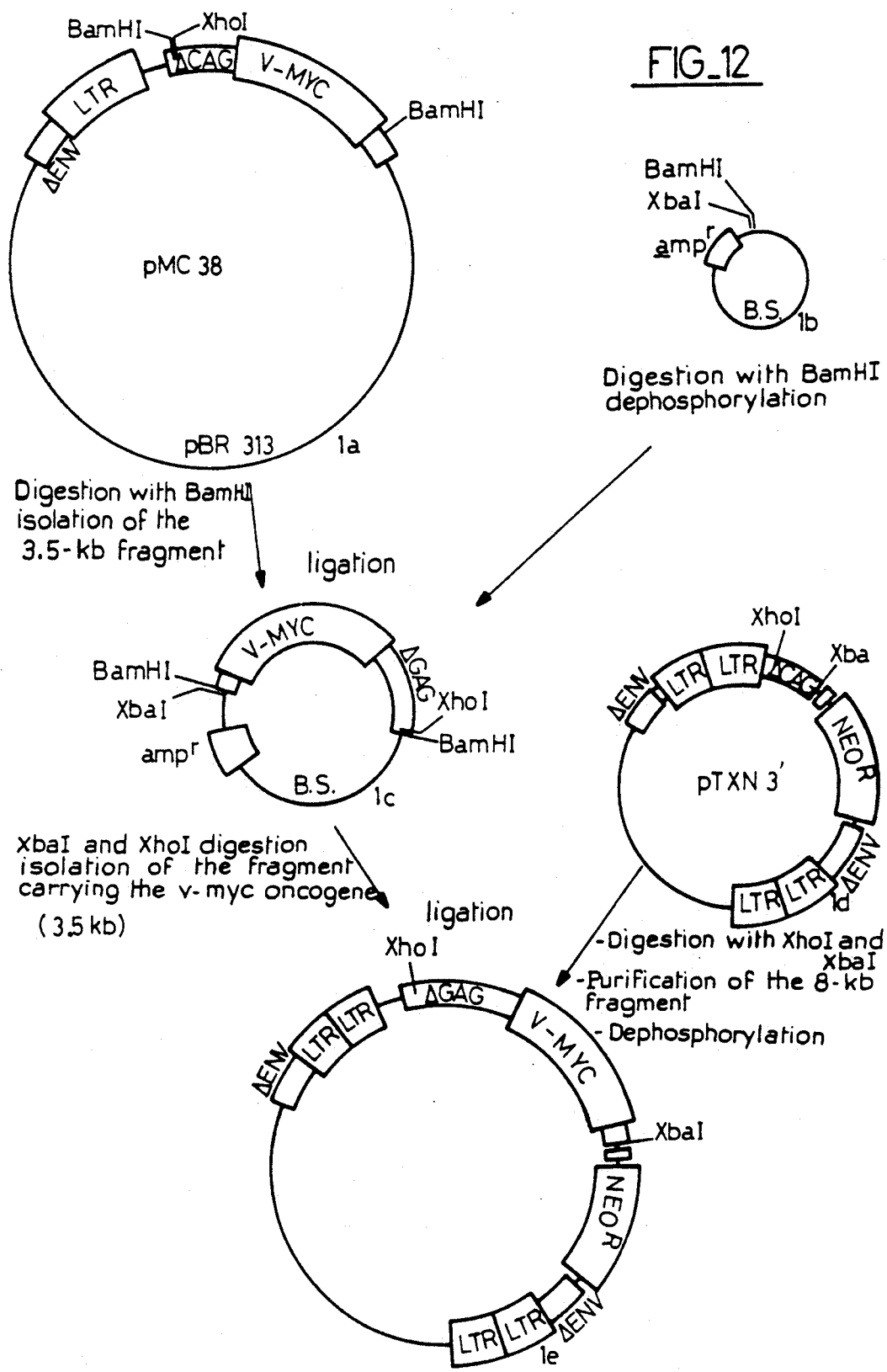
FIG. 12 shows the construction of the vector pMN 53 (Example 2).

Cells infected by a viral stock of this vector become resistant to neomycin and should express the cGH gene, hence producing avian growth hormone b.2) Construction of the vector pMN53 (FIG. 12)

The recombinant plasmid pMC38 carrying the avian retroviral genome of the virus MC29 in plasmid pBR313 was used.

A 3.5-kb BamHI fragment carrying the V-myc oncogene and a portion of the Δ-gag sequence was isolated from this plasmid and then inserted into the BamHI site of the Blue scribe plasmid. The resulting recombinant plasmid was referred to as BS-myc.

The 3.5-kb fragment bounded by the XhoI and XbaI sites and carrying the whole of the v-myc oncogene and a portion of the Δ-gag sequence was isolated and then inserted into the vector TXN3' (FIG. 12). The resulting vector was referred to as pMN53.

This vector containing the v-myc oncogene and the gene for resistance to neomycin is capable, on the one hand of transferring the resistance to neomycin, and on the other hand of inducing capacities for transformation in infected or transfected cells.

b.3) Construction of vectors carrying the mouse and avian p53 gene
  a) Mouse p53 gene.

Figure 13:
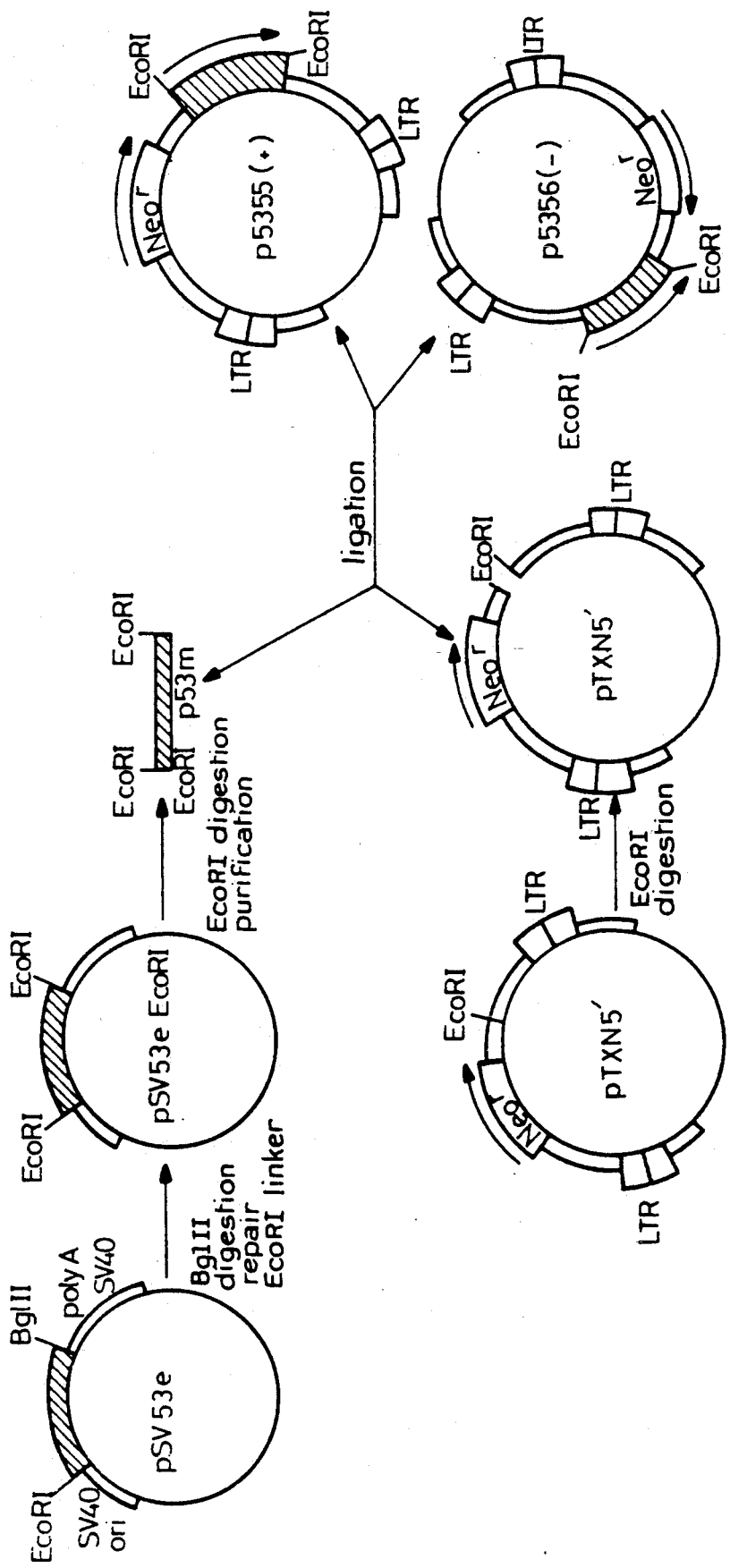
FIG. 13 shows the cloning of the mouse p 53 gene into TXN 5′ (Example 2).
Figure 14:
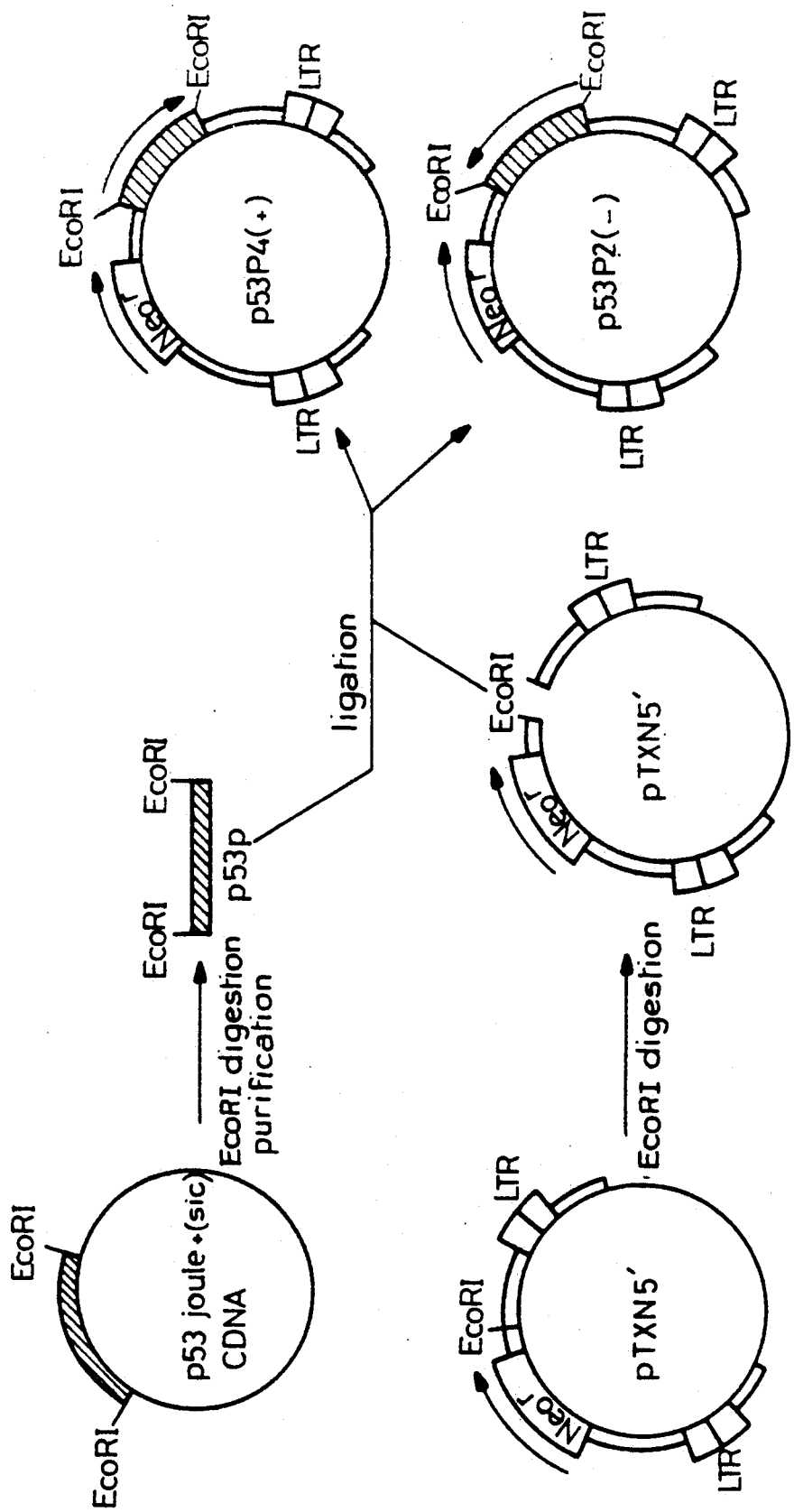
FIG. 14 shows the cloning of the chicken p 53 gene into TXN 5′.

The cDNA of the mouse p53 gene was supplied to us in the form of plasmid pSV53c (FIG. 13) by the Marie Curie foundation research institute, England. We replaced the BglII site at the 3' end of this gene by an EcoRI site. The EcoRI-EcoRI fragment corresponding to the cDNA of the mouse p53 gene was then purified and cloned into the retroviral vector TXN5' previously digested with EcoRI. Two vectors were thereby obtained the vector p53S5(+) which carries the cDNA of the mouse p53 gene cloned in the 3' position in the proviral transcription direction, and the vector p53S6(−) which carries the cDNA of the mouse p53 gene cloned in the direction opposite to the proviral transcription
  b) Avian p53 gene The cDNA of the avian p53 gene was supplied to us in the form of the cDNA chicken p53 plasmid (FIG. 14) by the IRSC, unit of molecular oncology, Villejuif.

The avian p53 gene, already bounded by the EcoRI sites, was directly cloned into the vector TXN5'. Two vectors were thereby obtained: the vector p53P4 (+) which carries the cDNA of the chicken p53 gene cloned in the proviral transcription direction, and the vector p53P2 (−) which carries the cDNA of the chicken p53 gene cloned in the direction opposite to the proviral transcription.

b.4) Construction of vectors carrying an env gene
Construction of the vectors pNE$^A$ and pNE$^B$ We constructed two retroviral vectors capable of transporting an env gene of RAV in cells in culture or in animals. These vectors are derived from the construction pTXN5' is described in this patent. It hence carries the neo gene conferring resistance to the antibiotic neomycin; and the env gene of subgroups A or B. They were constructed in two stages:
preparation of an env cassette, a step in common with that of the construction 3 (FIG. 35),
assembly of this cassette in plasmid pTXN5'.

Assembly of the plasmids pNE$^A$ and pNE$^B$ (FIG. 40).

A 4.4-kb fragment is generated from the vectors pUC env$^A$ and pUC env$^B$ either by partial digestion of the plasmid pUC env$^A$ with the enzyme HindIII, or by total HindIII digestion of the plasmid pUC env$^B$.

The cohesive ends of these fragments are filled in with Klenow DNA polymerase. These fragments are then partially digested with the enzyme EcoRI. A 1.9-kb fragment is then purified.

The 7.7-kb retroviral pTXN5' is doubly digested with the enzymes EcoRI and XbaI. The cohesive ends thereby generated are filled in with Klenow DNA polymerase, and they are then religated with itself. This results in a 7.3-kb plasmid referred to as pTXNΔJ, which is derived from pTXN5' and which has undergone a deletion of the J sequence containing a splicing acceptor signal.

Plasmid pTXNΔJ is partially digested with the enzyme StuI and then totally digested with the enzyme EcoRI. A 7-kb fragment is purified on gel and the 1.9-kb fragment containing the env gene is inserted into it. The resulting 8.9-kb retroviral vectors are referred to as pNE$^A$ or pNE$^B$, according to the nature of the subgroup of the env gene carried by it.

The neo gene which they transport is expressed from a genomic RNA, while the env gene is expressed from a subgenomic RNA produced by splicing of the former. The initiation codon of these genes is that of the Δgag residue of the vector, and is in phase with the reading frame of the env gene and of the neo gene.

Applications

These four vectors were transfected either into CEF in the presence of RAV-1 helper virus, or into cells of the trans-complementing line HF-g. The cells were selected by adding G418 to the culture medium. The viral stocks were recovered from these cells: "viremic" stocks from transfected CEF and "helper-free" stocks from transfected HF-g cells.

These viral stocks were used for infecting CEF cells which, in their turn, were selected by adding G418 to the culture medium. These cells were then studied for their capacity for growth in culture in vitro. Only CEF infected with the vector p53P4(+) (cDNA of the chicken p53 gene cloned in the proviral transcription direction) showed a capacity to multiply, similar to that which had been observed for the v-erbA oncogene, when cultured in a medium of low serum content (0.5% instead of 6% in the regular medium).

EXAMPLE 3

Vectors of the pAFY type

All the pAFY vectors transport two selection genes:
* The gene conferring resistance to neomycin (Neo) located in the 5' portion in the position of the v-erbA gene is inserted in the same direction as the retroviral transcription direction.
* The gene conferring resistance to hygromycin located in the 3' portion of the vector in the v-erbB position carries in its 5' portion the promoter-enhancer of the simian virus SV40 and the retroviral "att" sequence. Thus, these vectors possess two potential sites for specifically retroviral integration; one consists of the natural "att" site localized in the LTRs, the other corresponds to the extra "att" site inserted inside the vector at the 5' end of the gene conferring resistance to hygromycin B.

These constructions comprised three main steps:
preparation of the "att" sequences.
insertion of these sequences into plasmid pX343 transporting the bacterial gene conferring resistance to hygromycin B.
insertion of the ("att" sequence - SV40 promoter -gene conferring resistance to hygromycin B - SV40 polyadenylation signals) assembly into a retroviral vector.

Figure 15:
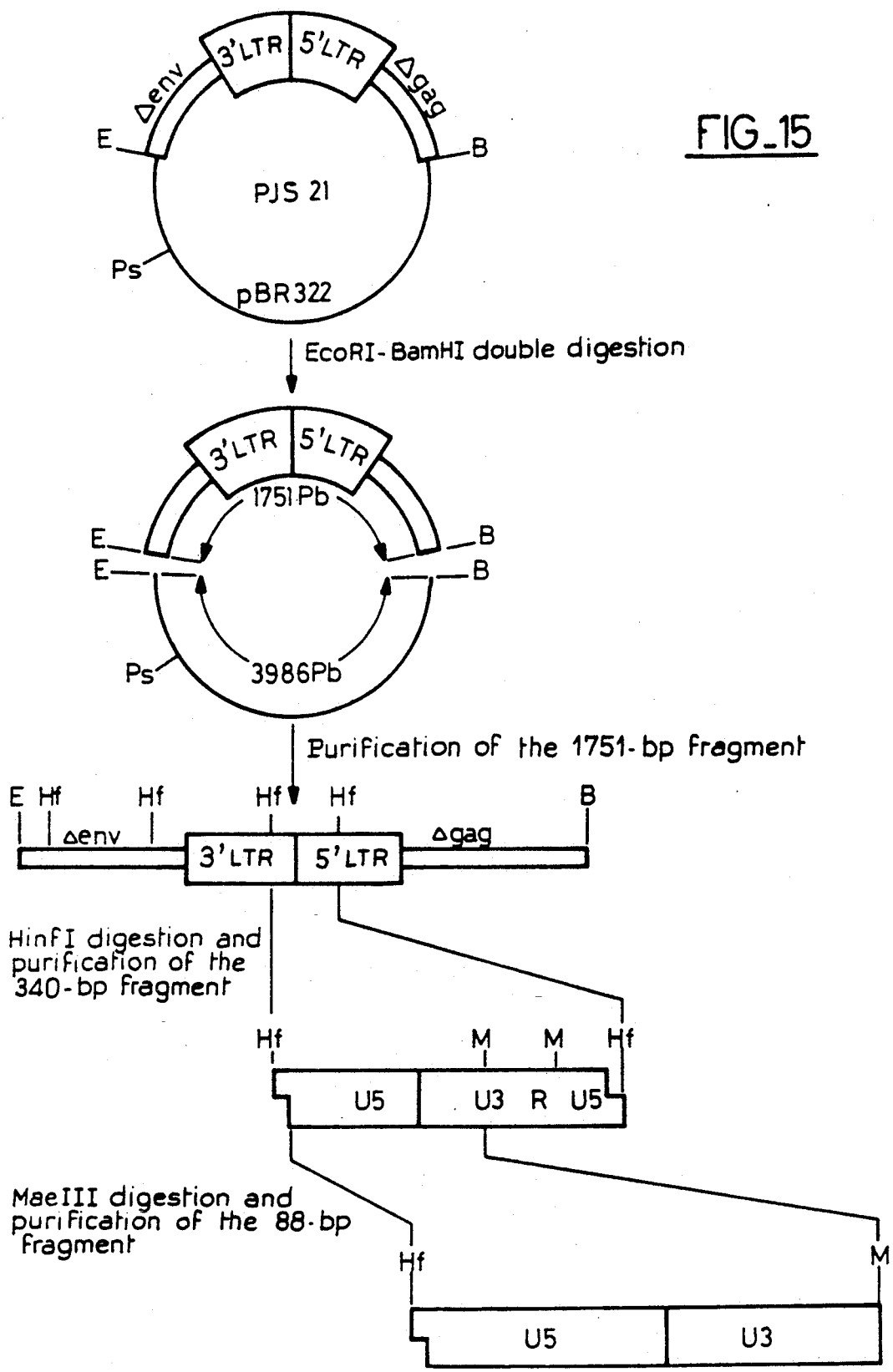
FIG. 15 shows the recovery of the "att" sequence from the LTR doublet of AEV.

1) "att" sequence (FIG. 15)
Plasmid pJS21: A 1751-nucleotide EcoRI-BamHI fragment carrying a portion of the env gene, an LTR doublet derived from natural fusion and a portion of the AEV gag gene is cloned between the EcoRI and BamHI sites of plasmid pBR 322 (FIG. 15).

The 88-nucleotide "att" sequence is isolated from this plasmid following 3 series of digestion and purification on gel;
  EcoRI/BamHI double digestion and recovery of the 1751-bp fragment.

Hinfl digestion and recovery of a 340-bp fragment.

Finally, MaeIII digestion and recovery of an 88-bp fragment.

After repair of the ends with Klenow polymerase, this 88-bp fragment was subcloned into the SmaI site of the vector M13 mp19 to take advantage of the sites of the polylinker carried by the coliphage M13 mp19. Three clones, Matt3, Matt5 and Matt55, were selected (FIG. 16).

2) Insertion of the "att" sequence into plasmid pX343 (FIG. 16)

Plasmid, pX343 contains the EcoRI-PvuII fragment (2295 bp) of plasmid pBR 322, a 340-bp fragment carrying the origin of replication of the SV40 virus, a 1.2-kb fragment carrying the bacterial gene conferring resistance to hygromycin, the intron of the gene coding for the t antigen and a fragment carrying the polyadenylation site of the SV 40 virus (FIG. 16). This plasmid was linearized with the enzyme PvuII which possesses a single cleavage site immediately upstream from the origin of replication of SV40. After EcoRI/PvuII double digestion and repair of the ends with Klenow polymerase, the "att" sequence is recovered, on the one hand from Matt3 and Matt5 in a 266-bp fragment, and on the other hand from Matt55 in a 354-bp fragment. These three fragments were integrated separately in the PvuII site of plasmid pX343.

3 clones were isolated (FIG. 16):

pXatt3 carries the "att" sequence oriented in the same transcription direction as that of the gene coding for hygromycin.

pXatt5 carries the "att" sequence oriented in the opposite direction relative to pXatt3.

pXatt55 carries an "att" sequence doublet placed in the same direction as pXatt5.

The two vectors (pXatt3, pXatt5) carry an att sequence in the direct orientation or in the opposite orientation, respectively, relative to that of the Hygro gene.

The above plasmids were transfected into QT6 cells, either uninfected, or previously infected with an RAV-1 virus designed to provide the Pol activity. The cells thus treated were selected with hygromycin B at a concentration of 40 µg/ml.

The intervention of the RAV-1 virus systematically produces a reduction in viability in culture, and hence a lessening of the number of resistant clones obtained. Taking into account all the factors in question, it does not appear that insertion of an att sequence gives rise to an intrinsically more frequent integration than the integrations observed in its absence.

13 cell clones transformed by pXatt5 (7 in the presence of RAV-1; 6 in the absence of RAV-1) were amplified, and their DNAs were examined after digestion with enzymes which cut only a single time in the plasmids employed. Hybridization is carried out using plasmid pX343. A 6-kb band is observed in all cases, its intensity varying according to the clone. In most of the latter, two additional bands are observed in addition, their sizes varying according to the clone. In some clones, more than two additional bands are observed.

These results show that the integrations are performed in the form of concatemers. The latter are cut by the enzyme into fragments of length equal to that of the initial monomer of transforming DNA. The variable bands represent the junction bands with the cell DNA. The presence of more than two bands in some clones may result either from several integrations carried out in the initial cell of the clone, or from the impure character of some of these clones which could, in fact, represent a mixture of two or more clones.

7 clones transformed by pX343 were examined in the same manner. The main difference relative to the clones transformed by pXatt5 appears to reside in the lower intensity of the 6-kb band, appearing to indicate that the integrations involve shorter concatemers.

These conclusions were confirmed by a dot-blot analysis of the DNAs: the intensity of the hybridization can be compared with that of a control series containing known amounts of pX343. The number of copies per clone is thereby estimated, with the following results:

transfection by pXatt5 alone . . . 2 to 7 copies per cell transfection by pXatt5+RAV1 . . . 2 to 30 copies per cell transfection by pX343 +RAV1 . . . 2 copies per cell.

The unique character of the major band observed shows that the concatemerizations take place between identical DNA segments cut at the same point and assembled in tandem. The observations made do not prove that this cleavage takes place at the att sequence. However, taking into account the effect of infection by RAV1 and of the known endonuclease properties of the enzyme Pol, this assumption appears likely. It may be supposed that, in the presence of this enzyme in the cell, the plasmids can undergo a uniform cleavage under conditions especially favorable to the production of chain units. A cloning of the junction fragments would be necessary in order to know whether the integration into the cell DNA also takes place at the att sequences.

The clones carrying a high copy number prove more resistant to hygromycin that those carrying smaller numbers of copies. So that the higher frequency of transformed clones observed after transfection by pXatt in the presence of the RAV1 may be due, in part, to a higher resistance of the latter clones with respect to toxins.

3) Production of pAFY vectors (FIG. 17)

Starting with the retroviral vector (pTXhoN) shown in FIG. 3, the EcoRI site juxtaposed to the XbaI site was converted to HindIII by the integration of a HindIII linker; the resulting vector is referred to as pCNH (FIG. 17).

On the DNA of the clones pXatt (FIG. 16), a single FspI site (F) carried by the fragment of plasmid pBR322 was converted to a HindIII site by the integration of a HindIII linker.

The 3.8-kb HindIII fragments derived from each of these plasmids were isolated and integrated separately in the single HindIII site of the vector pCNH (FIG. 17 and FIG. 18).

Six types of clones were obtained: they may be divided into two large categories:

either the 3.8-kb fragment is inserted in such a way that the direction of transcription of the gene coding for resistance to hygromycin corresponds to that of the retrovirus and of the gene coding for neomycin phosphotransferase II; this is the case with the vectors pAFY53, pAFY55 and pAFY525 (FIG. 18);

or the direction of transcription of the 3.8-kb HindIII fragment is opposite to that of the retrovirus; this is the case with the vectors pAFY35, pAFY33 and pAFY325 (FIG. 18).

The vector pAFY35 was studied on avian cell cultures:

a - Cotransfection of avian cells (CEF, QT6) by the DNA of this vector and the DNA corresponding to the genome of the RAV1 helper virus, followed by culturing on a selective medium containing G418, leads to the production of a viral stock (stock AFY35).

b.- Cells infected by this viral stock and cultured on a medium containing G418 continue to grow, and produce virions which transmit the resistance to G418. This result permits the conclusion that the proviral genome is inserted at the "att" site located between the LTRs, thereby leading to a normal viral production. However, the cells resistant to G418 are sensitive to hygromycin. This observation is open to two types of intepretation:
* either the gene conferring resistance to hygromycin is not expressed when it is placed in the opposite direction to the retroviral transcription direction.
* or the level of expression of this gene is too low to permit resistance to drug (hygromycin).

c - Cells infected by this viral stock (stock AFY35) and cultured on a medium containing hygromycin continue to grow, but prove incapable of producing virions transmitting the resistance to hygromycin or to G418; immunological analysis (ELISA) of the supernatant of these cells demonstrates, however, the presence of virions corresponding to the helper. This result permits the conclusion that the proviral genome may be integrated at the extra "att" site located inside the viral sequence, thereby leading to a complete disorganization of the retroviral structure; in this case, production of the vector virus (AFY) is abolished.

4) In addition to the vectors already mentioned in this example, we constructed other vectors which possess a general structure comparable to pAFY35 (FIG. 18).

These vectors all possess the NeoR gene in the position of the v-erbA oncogene and the PhleoR gene (conferring resistance to phleomycin) flanked by the promoter-enhancer and the polyadenylation sequence of the simian virus SV40 in the v-erbB position. This (promoter-enhancer/PhleoR gene/polyadenylation sequence) assembly is in the orientation opposite to the retroviral transcription direction.

pCYS74: this vector has no special characteristics other than those reported above.

pCYS84: this retroviral vector possesses, in addition to the elements carried by the vector pCYS74, an additional "att" sequence situated upstream from the promoter-enhancer of SV-40.

pCYS54: this vector is identical to the vector pCYS74, but has a deletion of 23bp in the 3'-terminal region of the U5 sequence of the 5'LTR.

pCYS64: this vector is identical to the vector pCYS54, but possesses an additional "att" sequence, like the vector pCYS84.

The vector pCYS64 permits an exclusive integration via the additional "att" sequence; the natural "att" sequence generated by the junction of the 2 LTRs during the first retroviral cycle is inactive as a result of the deletion created in the U5 sequence. The gene thus transferred is expressed under the control of the non-retroviral transcriptional promoter, in this case the SV40 promoter. The retroviral structure integrated via the additional "att" site possesses an LTR doublet. This doublet is no longer capable of providing for the functions of promotion of transcription.

The vectors pCYS54, pCYS74 and 84 constitute control systems for functioning, on the one hand of the additional "att" sequence, on the other hand of the effect of the deletion performed in the U5 region of the 5'LTR.

Construction of the vector pCYS64

Construction of the vector pCYS64 comprised several steps:

1) Mutagenesis of the U5 sequence of the 5' LTR. The EcoRI-HgiAI (1180bp) and HgiAI-SstI (290bp) fragments carrying the 5'portion and the 3'portion, respectively, of an LTR were isolated from the recombinant plasmid pJS21 (FIG. 15 (lacuna), and inserted between the EcoRI and SstI sites of plasmid BSK+. The resulting recombinant plasmid is referred to as BSK+LTR (FIG. 19). This plasmid (BSK+LTR) was linearized at the single BstEII site located at the end of the U5 sequence and subjected to a sequential degradation with Bal31 exonuclease. The clone selected after examination by nucleotide sequencing has a deletion of 23bp localized exclusively in the 3'-terminal portion of the U5 sequence. The recombinant clone formed from the coliphage M13mp18, carrying between its EcoRI and PstI sites a 1.5-kb fragment composed of an LTR from which 23bp have been deleted in the U5 sequence and of the PBS and leader sequence, was referred to as mp18ΔU5 (FIGS. 19 and 20).

2) Construction of the intermediate vector mp18ΔU5-Neo.

The NeoR gene was isolated from the vector pNL53 (described in Example 2 and FIG. 7) in a 1.8-kb SstI-HindIII fragment. This fragment was inserted between the SstI and ,HindIII sites of the recombinant vector mp18ΔU5 (FIG. 21). The recombinant clone selected was referred to as mp18ΔU5-Neo (FIG. 21).

3) Construction of an intermediate recombinant plasmid carrying the gene for resistance to phleomycin controlled by sequences of the simian virus SV40.

The production of this recombinant plasmid necessitated several intermediate steps:

a) Isolation and subcloning of the HygroR gene and the regulator sequences of the SV40 virus.

The 3.8-kb HindIII fragment was isolated from the vector pAFY35 (described in Example 3 and FIG. 18) and then inserted into the HindIII site of plasmid pBR322; the recombinant clone selected was referred to as pSVHy322 (FIG. 22).

b) Replacement of HygroR gene and of Intron of the t antigen by the gene for resistance to phleomycin=PhleoR.

The HygroR gene and the intron of the t antigen were deleted from the recombinant plasmid pSVHy322 by removal of the 1.8-kb HpaI-SmaI fragment.

The PhleoR gene was isolated in a 700-bp BstEIIH-paI fragment from the recombinant plasmid pUT507 containing the gene for resistance to phleomycin PhleoR controlled by an LTR promoter of the RSV retrovirus and the sequence carrying the transcription termination and polyanedylation signals of the SV40 virus.

The ends of this fragment were rendered blunt by treatment using the enzyme composed of the large fragment of Klenow polymerase, and the 0.7-kb fragment thus treated was then inserted between the blunt-ended HpaI and SmaI sites of plasmid pSVHy322 from which the HygroR gene and the intron of the t antigen of SV40 had been deleted.

The recombinant plasmid pSVPh corresponds to the clone which was selected (FIG. 22).

4) Insertion of an att sequence and an LTR into the recombinant plasmid pSVpH: construction of the intermediate vector pSVPhattLTR.
a) Isolation and subcloning of the att sequence.

A 200-bp KpnI-BamHI fragment was isolated from plasmid Matt5. The BamHI end was rendered blunt by repair using the large fragment of Klenow polymerase.

This fragment was inserted between the HindIII site (rendered blunt-ended by treatment with the large fragment of Klenow polymerase) and KpnI site. The recombinant plasmid BSK+att LTR corresponds to the clone selected (FIG. 23).

b) Insertion of the att sequence and the LTR into the recombinant plasmid pSVPh.

The 1520-bp KpnI-BstEII fragment carrying the att sequence and an LTR was isolated from the recombinant plasmid BSK+att LTR. The BstEII site was rendered blunt-ended by treatment using the large fragment of Klenow polymerase.

Plasmid pSVPh was linearized by partial digestion using HindIII. The ends were rendered blunt by treatment using the large fragment of Klenow polymerase. The linear molecules were digested again with the enzyme KpnI and the 6.5-kb fragment was isolated.

Between the KpnI site and the blunt end of this fragment, the fragment carrying the att sequence and the LTR was inserted to generate the recombinant plasmid pSVPh att LTR (FIG. 23).

5) Construction of the final vector pCYS64.

The 3.1-kb EcoRI-HindIII fragment carrying the 5'LTR mutated in the U5 sequence, the leader sequence nd the gene for resistance to neomycin was isolated from the recombinant plasmid mp18ΔU5Neo. The ends of this fragment were rendered blunt and this fragment was then inserted into the HindIII site, rendered blunt-ended by treatment with the large fragment of Klenow polymerase, of the recombinant plasmid pSVPh att LTR.

The recombinant plasmid thereby obtained was referred to as pCYS64 (FIG. 24).

Construction of the vector pCYS54

This vector constitutes a control system for the functioning of the vector pCYS64. Its structure is identical to that of the vector pCYS64, but does not possess the additional att sequence.

The experimental procedure for construction of this vector is exactly identical to that described for the vector pCYS64, with only one exception.

This exception relates to step 4 (insertion of an att sequence and an LTR in plasmid pSVPh) in the construction of the vector pCYS64.

The recombinant plasmid BSK LTR was doubly digested with the endonucleases EcoRV and XhoI. The 4. (lacuna) -kb fragment was isolated, the ends were rended blunt-ended by treatment with the large fragment of Klenow polymerase and it was then ligated with itself. The recombinant clone BSK+-ΔLTR is the clone which was selected.

The 1350-bp KpnI-BstEII fragment carrying an LTR was isolated and the BstEII end rendered blunt by treatment with the large fragment of Klenow polymerase, and then inserted between the KpnI site and HindIII site, rendered blunt-ended, of the recombinant plasmid pSVPh.

The recombinant plasmid pSVPhLTR corresponds to the clone selected (FIG. 23).

The fifth step is identical to that of the construction of the recombinant plasmid pCYS64.

The resulting recombinant plasmid was referred to as pCYS54 (FIG. 24).

Construction of the vectors pCYS74 and pCYS84

The vectors pCYS74 and pCYS84 are derived from the vectors pCYS54 and pCYS64, respectively, described above. Relative to these two vectors, the vectors pCYS74 and pCYS84 possess no modification in the U5 sequence of the 5'LTR.

The recombinant plasmids pCYS54 and pCYS64 were partially digested with SstI and then totally digested with ClaI, and the 9-kb fragments purified on agarose gel.

The 1.1-kb SstI-ClaI fragment carrying an AEV LTR was isolated from plasmid BSK+LTR, and then inserted into each of the 9-kb fragments prepared above.

The recombinant plasmid obtained from the 9-kb fragment derived from pCYS54 was referred to as pCYS74 (FIG. 25). The recombinant plasmid obtained from the 9-kb fragment derived from pCYS64 was referred to as pCYS84. (FIG. 25).

EXAMPLE 4

Construction of the defective helper genome

Several constructions were carried out for this purpose.

a/ A construction PHF 13. This contains an RAV-1 LTR from which some fifty nucleotides have been deleted in the region which carries the encapsidation signal. It carries the gag, pol and env genes of RAV1. At its 3' end, the 3' LTR has been replaced by the polyadenylation sequence of the TK gene of the HSV virus. A similar construction pHF 405 has undergone a deletion which extends up to the PBS segment of the virus, involving 150 nucleotides in all.

b/ A construction pHF13-Hygro was carried out from pHF13. The latter contains a Hygro gene, providing resistance to hygromycin, inserted after the termination sequence carried by pHF13. The possible functioning of this Hygro gene is conditioned by a reinitiation of translation in the 3' portion of a total transcript.

1. QT6 cells were cotransfected with the constructions pHF13 or pHF405 combined, respectively, with plasmid pXJ12. After selection on G418, 39 clones were isolated, of which 25 received plasmid pHF13 and 14 plasmid pHF405. Out of this set of clones, 22 show a positive signal in Elisa for the detection of the intracellular P27 protein. Of these positive clones, only 7 release the protein into the culture medium. These 7 clones were tested for the production of virions capable of transferring the resistance to G418. Two clones (AIII2 and AIII6) proved positive in the test. They both contain the construction pHF13. While the supernatants of these clones transmit G418 resistance to CEF, they do not transmit the viral production, which demonstrates that these two clones behave as clones of helper cells. Titration of the activity of these supernatants shows that the concentration of virions containing a functional Neo gene is low (approximately 50 per ml of supernatant, equivalent to 1,000 to 10,000 times less than a culture infected by RAV1 ).

Analysis of the viral proteins synthesized in the clones AIII2 and AII6 show that the gag (Pr76 and P27) and pol (Pr180) proteins are produced at levels 10- to 20-fold lower than in QT6 cells infected by a non-deficient helper virus; the viral RNAs are present therein at levels 5- to 10-fold lower than in an infected culture. The disparity between the deficits observed in respect of the proteins or RNAs and of that of the viral production, respectively, suggest that the explanation might lie either in a reduced production of the env protein, or in a difficulty in assembling the viral particles 2. $2 \times 10^6$ QT6 cells were transfected with the constructions pHF 13 or pHF 405, at the same time as with an independent construction pX343 carrying a functional Hygro gene. After selection with hygromycin, 90 cell clones were isolated On each of these clones, the p27 protein characteristic of the functioning of the gag gene was assayed by Elisa both in a cell lysate and in the culture supernatant. 44 clones produce the p27 protein intracellularly. The existence of a correlation between the intracellular and extracellular concentrations of this protein is noted. The system behaves as if the characters under study depended on two independent random factors:

one of them governing the intracellular production of the p27 protein;

the other governing the capacity to effect the discharge of this protein into the culture medium, to the extent that it is produced by the cell.

Of these 44 clones producing the p27 protein intracellularly, only 22 discharge significant amounts of it into the culture medium. Of these 22 clones, 7 proved non-productive of the HELPER viruses. It is noted that some non-viroproductive cultures produce almost as much p27 protein as cultures of cells infected by RAV-1. 4 clones were selected for having the highest production of p27 protein. All 4 contain the construction pHF13. These clones are transfected separately with the vector pTXN3' After selection on G418, the resistant cells are amplified in bulk. Their culture supernatant is capable of transmitting G418 resistance to CEF, but do not transmit the viral production. The cells hence behave as Helper cells. Titration of the activity of their supernatants may be estimated, depending n the clone, at values between $3 \times 10^3$ and $2 \times 10^4$ TXN3' particles per ml of supernatant. The value of $2 \times 10^4$ obtained with the clone MBG is only 50-fold lower than that obtained with a culture coinfected by TXN3'/RAV-1.

3. QT6 cells were transfected with the construction pHF13-Hygro. Eight lines resistant to hygromycin were obtained. Those which were analyzed prove very strongly productive of the p27 protein and non-viroproductive.

The helper construction carried out contains the three viral genes, gag-pol-env, of the RAV-1 helper virus placed under the transcriptional control of an LTR of the same virus. The 3' LTR is replaced by a 600-nucleotide sequence containing the transcription termination and polyadenylation signals of the thymidine kinase gene of the Herpes Simplex I virus. The 3' LTR participates:

in the polyadenylation of the viral RNAs, in the circularization of the genomic RNA during encapsidation, in the integration and transcription of the viral genome during secondary infection.

Its absence hence constitutes a first level of blocking of viremia.

The construction of the defective helper genome (pHF 13) also comprises a deletion of 52 nucleotides from the non-translated 5' leader sequence. This deletion encompasses a region of approximately 30 nucleotides cis-acting in the encapsidation of the viral RNA. This deletion constitutes a second level of blocking of viremia.

Three cassettes were constructed separately and then assembled according to the protocol of FIG. 29:

the promoter (FIG. 26)
the polyadenylation signal (FIG. 27)
the gag-pol-env viral genes (FIG. 28)

1) The promoter (clone pDIPO-123, FIGS. 26 and 27 a) General comments

The promoter consists of two LTRs in tandem; the one located at the 3' end originates from the RAV-1 helper virus (obtained from Dr. J. M. Bishop, U.C. San Francisco), the other, located at the 5' end, is a hybrid between the LTRs of RAV-2 and RAV-1 in which a portion of the U3 sequence (between the Sph I and Tag I sites) has been deleted. This probably results in a non-functional LTR. The structure of the assembly of this promoter region is shown diagrammatically in FIG. 30B.

b) Production

The clone pRAV-1 is digested with the endonuclease EcoRI. The fragment transporting the plasmid sequences is recircularized to generate the clone pDIPO 1. The 0.6-kb EcoRI fragment is purified and then recloned at the ECoRI site of pBR 322 to generate pDIPO 3 (FIG. 26).

The clone pRAV-2 (obtained from Dr. Skalka, Roche Institut Nutley) is digested with the endonuclease Sph I. The fragment transporting the plasmid sequences is treated with T4 DNA polymerase to generate blunt ends. It is recirculated in the presence of Cla I linkers to generate the clone pDIPO 4 (FIG. 26).

The clone pDIPO 1 is digested with the endonucleases EcoRI and SacI. The clone pDIPO 3 is digested with the endonucleases EcoRI and TaqI. The clone pDIPO 4 is digested with the endonucleases SalI and ClaI. The three fragments are purified and then religated between the SacI and SalI sites of pBR 322 to generate the clone pDIPO 123 (FIG. 26). This construction is made possible as a result of the compatibility of the ClaI and TaqI sites.

2) The polyadenvlation structure (clone pGAS-Cla, (FIG. 27)

a) General comments

Two polyadenylation signals are generally used in eukaryotic expression vectors.

that of the early genes of the SV40 virus that of the thymidine kinase (TK) gene of the Herpes Simplex I virus.

We chose that of the TK gene, since that of SV40 contains a splicing signal liable to interfere with those of the retrovirus.

b) Production

The clone pSV2 gpt (Mulligan et al.) is digested with the endonucleases HindIII and ApaI. The fragment transporting the origin of replication of SV40 and the polyadenylation signal is treated with T4 DNA polymerase to generate blunt ends. It is then recircularized in the presence of SacI linkers to generate the clone pSV-Sac.

The clone pAG 60 (obtained from Dr. A. G. Garapin, Institut Pasteur Paris) is digested with the endonucleases BgIII and Sma I. The fragment transporting the promoter and the polyadenylation signal of the TK gene is treated with DNA polymerase I (Klenow fragment) to generate blunt ends. It is recircularized in the presence of SacI linkers to generate the clone pAG-Sac.

The clone pSV-Sac is linearized with the endonuclease EcoRI. It is treated with Klenow DNA polymerase I to generate blunt ends and is then redigested with the endonuclease SacI. The SacI-EcoRI fragment containing the polyadenylation signal of SV40 is removed and replaced with the SacI-PvuII fragment of the clone pAG-Sac which contains the polyadenylation signal of the TK gene. The exchange generates the clone pGAS, in which the polyadenylation signal of the TK gene is associated with the SV40 promoter. The association of the EcoRI sites, rendered blunt with DNA polymerase, and PvuII site generates the PvuII site.

The clone pGAS is finally linearized with the endonuclease PvuII and then recircularized in the presence of ClaI linkers to generate the clone pGAS-Cla (FIG. 27).

3) The gag-pol-env viral genes (clone pHP 2)
a) General comment

These viral genes are derived from the RAV-1 helper virus (subgroup A).
b) Production The clone pRAV-1 is digested with the endonuclease SalI. The fragment containing the 3' end of the env gene and the LTRs is recircularized to generate the clone pEnv.

The clone pEnv is digested with the endonucleases SalI and AccI. The fragment containing the 3' end of the env gene is purified and then treated with Klenow DNA polymerase I to generate blunt ends. It is ligated in the presence of SacI linkers (it will be noted that the addition of SacI linkers to the previously repaired SalI site recreates the SalI site). The fragment is redigested with the endonucleases SacI and SalI and then religated between the SacI and SalI sites of pBR 322 to generate the clone p. 800el (FIG. 28).

The clone p. 800el is digested with the endonucleases SalI and SacI to release the 3' end of the env gene. In parallel, the clone pRAV-1 is digested with the endonucleases SacI and SalI to release the gag-pol genes and 5' end of the env gene. The two fragments are religated in the SacI site of the clone pSV-Sac to generate the clone pHP 2 (FIG. 28).

In this construction, the gag-pol-env viral genes are placed under the transcriptional control of the promoter of the early genes of SV40 and under the transcription termination control of the polyadenylation signal of the gene.

4) Deletion of the encapsidation sequence and assembly of the three cassettes (clone pHG 13, FIG. 29)

The clone pDIPO 123 is linearized at the SacI site located in the non-translated 5' sequence on the immediate 3' side of the encapsidation sequence (FIG. 30 C). The linearized DNA is subjected to a controlled digestion with Bal exonuclease and then digested with the endonuclease SalI. The fragments containing more or less extensive deletions are recloned into the replicative form of the coliphage M13 between the SalI and SmaI sites (blunt ends) The clones mpll-DIPO 123 thereby generated are analyzed by sequencing to monitor the extent of the deletion. One of them, containing a deletion of 52 nucleotides at the 5' end of the SacI site (FIG. 30 C), was chosen for producing the defective helper pHF 13.

The clone mpll-DIPO 123, previously selected, is digested with the endonucleases SacI and ClaI. The fragment containing the LTRs and the mutated leader sequence is purified and then religated between the SacI and ClaI sites of the clone pGAS-Cla described in section 2. This construction generates the clone pGAS-LTR.

The clone pHP 2 is digested with the endonuclease SacI. A fragment is released transporting the three gag-pol-env viral genes. It is inserted at the SacI site of the clone pGAS-LTR to generate the clone pHF 13. The structure of the pHF 13 genome and that of the RAV-1 genome are shown in FIG. 30 A.

5) In addition to the vectors already mentioned in this example, we constructed the following vectors:

pGPEH: this vector is derived from the vector pHF13 (FIG. 29). It contains, in addition to the structures described for pHF13, the $Hygro^R$ gene (conferring resistance to hygromycin B) placed at the 3' end of the env gene, and a second splicing acceptor site placed upstream from the Hygro R gene. This vector confers on the cells which harbor it trans-complementing capacities of the same type as the vector pHF13. However, this construction makes it possible to provide, on the same DNA, the gag-pol-env viral genes which provide for the function of trans-complementation, and the $Hygro^R$ selection gene.

pGPH: this vector is identical to the above (pGPEH) with the exception of the env gene, which has been deleted in this construction. It possesses only a single splicing acceptor site placed upstream from the HygroR gene.

pPh.E: this vector is derived from the vector pHF13; the gag and pol genes have been deleted and replaced by the gene for resistance to phleomycin (PhleoR). In addition, the env gene which remains is preceded by the splicing acceptor site. Two constructions of the same type were carried out, and are distinguished by the nature of the env gene, either pPh.$E^A$ containing the env gene of subgroup A, or pPh.$E^B$ containing the env gene of the subgroup B.

These two vectors pGPH and pPh.E act in complementary fashion in the cell harboring them, to yield the gag and pol genes (vector pGPH) on the one hand, and env gene (vector pPh.E) on the other hand, to confer trans-complementing capacities on the cells In addition, the cells are coselected on the basis of their characters of resistance to hygromycin and to phleomycin, provided by each of the two vectors.

5.1 Construction involving the genome of the RAV-1 helper virus 5.1.1. Construction of the vector pGPEH The helper construction carried out (FIG. 31) is derived from the helper construction pHF13. Apart from the gag-pol-env viral genes, it carries a hygro gene whose expression confers resistance to hygromycin. This gene is inserted into the construction pHF13 immediately downstream from the env gene, and is equipped with its own splicing acceptor site.

In a first stage, a plasmid is constructed containing the splicing acceptor site of RAV-1 and the HygroR gene placed in the same transcriptional direction (plasmid Sa-H, FIG. 32).

In a second stage, assembling of these two sequences in pHF13 is carried out between the end of the env gene and the beginning of the polyadenylation sequence (plasmid pGPEH, FIG. 33).

5.1.2. Construction of plasmid Sa-H (FIG. 32)

Starting with plasmid pHF13, doubly digested with the restriction enzymes KpnI and SalI, a 1.1-kb fragment containing the beginning of the env gene of RAV-1 is purified on agarose gel. This fragment is digested with the enzyme XhoI, and a 263-bp fragment containing the splicing acceptor site of the env gene of RAV-1 is then purified.

The HygroR gene edged with SstI cohesive ends is inserted by ligation into the SK+ blue script plasmid (3Kb) marketed by Stratagene, digested with the enzyme SstI. The resulting plasmid, referred to as BS-H+, is digested with the enzymes KpnI and XhoI The 263-bp sequence is then inserted into this vector. This results in a 4.5-kb plasmid referred to as BSH-Sa. The latter is digested with the enzymes AccI and NotI; the cohesive ends thereby generated are filled in with the enzyme Klenow DNA polymerase and religated with themselves. A 4.5-kb plasmid referred to as Sa-H, which carries the splicing acceptor site of the env gene of RAV-1, as well as the HygroR gene oriented in the same transcriptional direction and placed in the same reading frame as that of the env gene, is thereby obtained.

5.1.3. Construction of plasmid pGPEH (FIG. 33)

Plasmid Sa-H is doubly digested with the enzymes KpnI and pvuII. A 1.7-kb fragment containing the splicing acceptor site of RAV-1 and the hygro gene is then purified on gel. This sequence is inserted by ligation into the vector Blue Scribe (34 b) previously digested with the enzymes KpnI and SmaI. This results in a 4.7-kb plasmid referred to as mp18-SaH. The latter is partially digested with the enzyme SstI. A 1.5-kb fragment containing the splicing acceptor site of RAV-1 and the hygro gene, and edged by SstI cohesive ends, is then purified; thereby enabling it to be inserted by ligation into pHF13 previously linearized by partial SstI digestion. The size of the resulting plasmid PGPEH is 11.8 kb.

5.1.4. Construction of the vector pGPH

We then attempted to carry out a series of helper constructions by following the following strategy: transferring the helper genome of RAV-1 in two stages. The two types of construction enable either the gag-pol genome or the env genome to be transferred. Each of these series of construction transports, in addition, a different selection gene.

The construction transporting the gag-pol genes (FIG. 31) (referred to as pGPH) carries, in addition, the HygroR selection gene. The latter is inserted in place of the env gene in pHF13. The implementation of this construction is carried out in two stages:
preparation of the cassette comprising the splicing site of the env gene of RAV-1 joined to the hygro gene. This step, described in the construction pGPEH, leads to the production of plasmid Sa-H;
assembling of this cassette with the gag-pol genome.

5.1.5. Construction of plasmid pGPH (FIG. 34)

Starting with pHF13 partially digested with the enzyme SstI, the 10.3-kb fragment is purified on gel and then digested with the enzyme KpnI. An 8.4-kb fragment is then purified, and a 1.5-kb sequence containing the splicing acceptor site of the env gene of RAV-1 and the HygroR gene is inserted into this by ligation. This sequence originates from a partial SstI digestion, followed by a digestion of plasmid Sa-H with the enzyme KpnI (FIG. 32). The size of the resulting plasmid pGPH is 9.6 kb.

5.1.6. Production of the vectors pE$^A$Ph and pE$^B$Ph

The construction of a first series of vectors transporting an env gene and a gene for resistance to phleomycin (phleo gene) was carried out in two stages:
isolation of the whole env gene in a plasmid pUC19, vector pUC-env;
insertion of this gene into a plasmid transporting a hygro gene driven by an RSV (Rous Sarcoma Virus) LTR. The final construction (plasmid pE-Ph) is carried out in duplicate:
one transports the env gene of RAV-1 (subgroup A), the other that of RAV-2 (subgroup B).

5.1.7. Production of plasmids pUC envA and pUC envB (FIG. 35)

Starting with plasmid pRAV-1 or pRAV-2 transporting the retroviral genomes RAV-1 or RAV-2, digested with the enzyme SalI and KpnI, a 1.1-kb fragment containing the 5' half of the env gene is purified on gel. This sequence is ligated with plasmid pUC19 previously digested with the enzymes KpnI and SalI. This results in the formation of pUC-env5', the size of which is 3.6 kb.

Plasmids pRV-1 and pRAV-2 are digested with the enzyme SalI, and then with the enzyme AccI. A 0.9-kb fragment is then purified and ligated with plasmid pUC env5' previously linearized with the enzyme SalI. From this ligation reaction mixture, a 4.4-kb fragment is purified on gel, this fragment possessing two incompatible ends, AccI and SalI. The latter are filled in using Klenow DNA polymerase and the assembly is religated with itself. This results in the formation of a 4.4-kb plasmid, referred to as pUC env$^A$ or pUC env$^B$ according to the nature of the subgroup of the env gene which it carries.

5.1.8. Construction of the vectors pE-Ph (FIG. 36)

Starting with plasmid pUC env$^A$ partially digested with the enzyme HindIII, a 4.4-kb fragment is purified on gel. A fragment of homologous size is also obtained from plasmid pUC env$^B$ digested with the enzyme HindIII. The 4.4-kb fragments are filled in with Klenow DNA polymerase and are then partially digested with the enzyme EcoRI. A 1.9-kb fragment is purified on gel and its cohesive ends are filled in with Klenow DNA polymerase. This fragment is then inserted by ligation into plasmid pUT507 previously digested with the enzyme Bst E2, and whose cohesive ends have been filled in with Klenow polymerase. Plasmid pUT507 (4.1 kb) carries the phleo bacterial gene driven by an RSV LTR promoter. Ligation enables us to obtain the vectors pE$^A$ph and pE$^B$ph (according to the nature of the subgroup of the env gene which it transports), whose size is 5.9 kb.

5.1.9. Production of the vectors pPhE$^A$ and pPhE$^B$

We constructed a second series of vectors carrying the env gene (subgroup A or B) and the Phleo gene. These vectors differ from plasmids pE-Ph by the processes of expression of the genes transported (FIG. 31).

The helper vectors pPh E are constructed in three stages:
preparation of a pUC.env PA. cassette containing an env gene and the polyedenylation sequence of the Sv40 virus;
preparation of a pLTR-phleo cassette containing the promoter of pHF13, the leader sequence of RAV-1 from which the encapsidation sequence has been deleted, a residue of the gag gene of RAV-1 and the phleo gene;

assembling of the above two cassettes and production of plasmids pPh.E.

Figure 37:
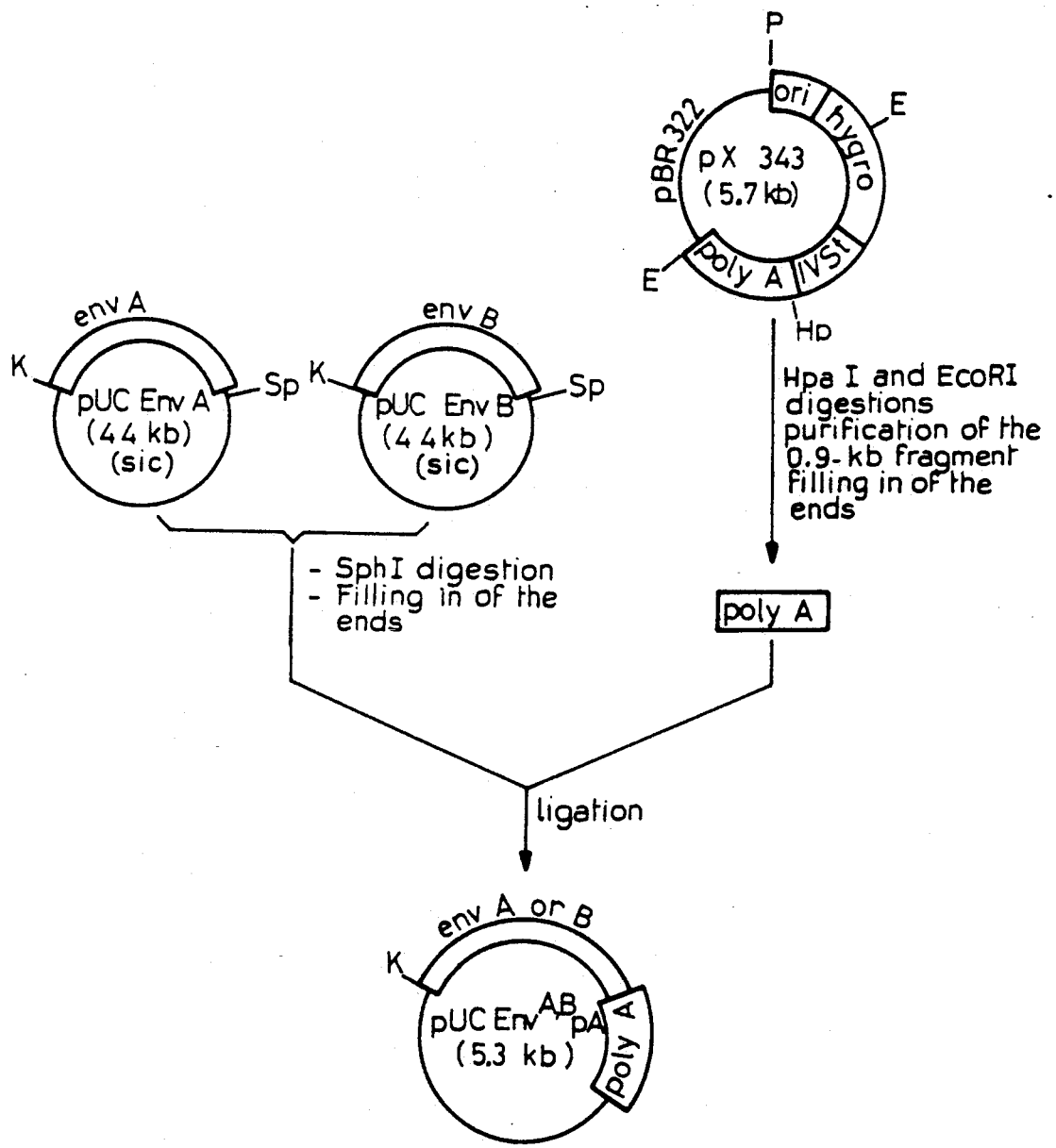

5.1.10. Preparation of the pUC env$^A$ pA and pUC env$^B$ pA cassettes (FIG. 37)

Starting with plasmid pX343, a vector carrying a gene for resistance to hygromycin, equipped with a promoter and a polyadenylation sequence of the SV40 virus, digested with the enzymes HpaI and EcoRI, a 0.9-kb fragment is purified on gel and its cohesive end is filled with in Klenow DNA polymerase.

The fragment is then inserted by ligation either into plasmid pUC envA or into pUC envB which have been previously linearized with the enzyme SphI, and whose cohesive ends have been filled in with T4 DNA polymerase. This results in the formation of plasmids pUC envA pA and pUC envB pA, the size of which is 5.3 kb.

5.1.11. Preparation of plasmid pLTR-phleo (FIG. 38)

The 0.9-kb promoter portion of this construction is purified on gel after digestion of pHF13 with the enzyme BamHI and ClaI.

The phleo gene is prepared by purification of a 0.6-kb fragment originating from a digestion of plasmid pUT56, carrying the reading frame of the phleo gene, with the enzyme BamHI and NotI.

These two fragments are inserted by double ligation into plasmid Sk+ (marketed by Stratagene) digested with the enzymes ClaI and NotI.

This results in the formation of a 4.5-kb plasmid referred to as pLTR phleo.

5.1.12. Assembly of plasmids pPH E$^A$ and pPH E$^B$ (FIG. 39)

Starting with the vector pUC env$^A$ pA and pUC env$^B$ pA completely digested with the enzyme NarI, the cohesive ends are separated with Klenow DNA polymerase.

Starting with plasmid pLTR-phleo completely digested with the enzymes pVUII and StuI, a 1.65-kb fragment is purified on agarose gel. The latter is then ligated into the pUC env pA vectors prepared as described in the previous section.

This results in the formation of the 7.0-kb plasmids pPh E$^A$ and pPh E$^B$.

EXAMPLE 5

Construction of an avian helper cell

1) Transfection of cells with plasmid pHF 13

$5 \times 10^5$ cells (quail continuous line: Q16) were transfected with 500 ng of the selection plasmid pX343 and 3 µg of plasmid pHF 13. Plasmid pX343 transports the gene for resistance to hygromycin B and confers resistance to this antibiotic on the cells which express it.

The transfection is carried out by the technique described by Kawai (polybrene DMSO). After 10 days of selection in the presence of 50 µg of hygromycin B per ml of medium, the resistant cell clones are isolated and amplified. They are then analyzed for production of the p27 gag viral protein in the culture supernatant, by an immunoenzymatic method (ELIS.A). One of the two (MBg) was selected for having the highest production of p 27 gag proteins.

2) Transfection of the cell clone MBg with the vector pTXN 3' genome $5 \times 10^5$ cells of the clone MBg were transfected with 500 ng of plasmid pTXN 3'. pTXN 3' transports the gene for resistance to neomycin and confers resistance to G418 on the cells which express it. After 10 days of selection in the presence of 200 µg of G418 per ml of medium, the resistant cell clones are amplified in bulk. The resulting cell population (MBg-TXN 3') is analyzed for its capacity to produce infectious viral particles of the vector type.

3) Detection of production of "helper-free TXN3'" viral particles by MBg-TXN 3' cells Three batches of $10^6$ cells of the QT6 line were infected with 1 ml, 100 µl and 10 µl respectively, of the culture supernatant of MBg-TXN 3' cells. 24 hours after infection, the cells infected with TXN 3' particles are selected by adding G418 (200 µg/ml). After 10 days of selection, counting of the cell clones resistant to the antibiotic yields an estimate of the number of vector viral particles present in the culture supernatant of the MBg-TXN 3' cells. The number is estimated at $10^4$ TXN 3' particles per ml of culture supernatant.

The G418-resistant cell foci thereby obtained are amplified. Analysis of their culture supernatant by an immunoenzymatic method reveals the absence of viral production. This result is confirmed by infecting chick embryo fibroblasts with these supernatants. No focus of resistance to G418 develops therein after 15 days of selection with the drug (200 µg/ml). It is concluded from this that the particles produced by the MBg-TXN 3' cells are exclusively of the vector type, in the total absence of helper particles. Deposition of strains:

The following strains were deposited at the Collection Nationale de Culture de Microorganisme (National Collection of Microorganism Cultures) of the Pasteur Institute, 28 rue du Docteur Roux - 75724 PARIS Cedex 15 under the following numbers:

E. coli strain pAFY 53 no. I-696
E. coli strain pNL 35 no. I-697
E. coli strain pNL 53 no. I-698
E. coli strain pAFY 525 no. I-699
E. coli strain pAFY 325 no. I-700
E. coli strain pAFY 55 no. I-701
E. coli strain pAFY 35 no. I-702
E. coli strain pAFY 33 no. I-703
E. coli strain pTXN3' no I-704
E. coli strain pTXhoL no. I-705
E. coli strain pTXN 5' no. I-706
E. coli strain pTXN 3' gaz- no. I-707
E. coli strain pHF-13 no. I-708 on Oct. 19, 1987.

We claim:

1. A viral vector for the integration and expression of at least one heterologous gene in avian cells, which consists wholly or in part of the proviral genome of avian erythroblastosis virus in which said heterologous genes replace the v-erbA gene and the v-erbB gene, and wherein said genes are either controlled by an LTR promoter of the same virus, in which case a first, heterologous marker gene is in the v-erbA position and a different second, useful heterologous gene is in the v-erbB position, the heterologous genes being in the same reading frame as the genes they replace, or said second gene is controlled by the heterologous promoter, in which case an additional att sequence is situated upstream from said heterologous promoter and between the two LTR sequences.

2. The viral vector as claimed in claim 1, which is useful, in particular, for integration in chick cells, wherein two heterologous genes are controlled by an avian LTR promoter.

3. The vector as claimed in claim 2, wherein said first, heterologous marker gene is translated from the start AUG of the gag gene and said second, useful heterologous gene is translated from the start AUG of the gag gene or from its start AUG, but always in the same reading frame as that of the gag gene.

4. The vector as claimed in claim 3, wherein a stop condon is introduced between the gag gene and the second useful heterologous gene or the start AUG belonging to said useful gene.

5. The vector as claimed in claim 4, wherein the stop condon is located at an optimum distance of 65 nucleotides from the start AUG codon of said second useful gene.

6. The vector as claimed in claim 1, wherein a first, heterologous marker gene replaces the v-erbA position controlled by the 5' LTR promoter and a second, useful heterologous gene replaces v-erbB controlled by a heterologous viral promoter, and which vector contains an additional att sequence situated upstream from the heterologous promoter.

7. The vector as claimed in claim 6, wherein the second heterologous gene replaces the v-erbB position and is under the control of the heterologous viral promoter and the heterologous polyadenylation sequence, and wherein the promoter—useful gene—poly adenylation sequence assembly is in the opposite orientation to the retroviral transcription direction.

8. The vector according to claim 6, which contains, in addition, a deletion in the U5 portion of the 5' LTR so that it is no longer functional.

9. The vector according to claim 1, wherein the heterologous promoter is the SV40 promoter.

10. A viral vector according to claim 1 capable of immortalizing avian cells which it infects, which consists wholly or in part of the proviral genome of avian erythroblastosis virus and which genome possesses, controlled by an LTR promoter of the same virus, a P53 gene which replaces v-erbA or v-erbB and a marker gene which replaces a remaining gene either v-erbB or v-erbA.

11. A viral vector capable of immortalizing the avian cells which it infects, which consists wholly or in part of the proviral genome of avian erythroblastosis virus and which genome possesses, controlled by an LTR promoter of the same virus, a marker gene which replaces the v-erbB gene and a fusion gene composed of the gag gene sequence and the sequence of the v-myc oncogene derived from the genome of the avian retrovirus MC29, said oncogene in the same reading frame and replacing the v-erbA gene.

12. A plasmid for integration and expression of a heterologous gene in avian cells, said plasmid comprising the proviral genome of avian erythroblastosis virus as described in claim 1.

13. A virion obtained by transfection of avian cells with a plasmid as claimed in claim 1 and infection of said cells with a helper virus capable of providing the appropriate packaging functions.

14. An avian cell infected or transfected by a viral vector according to claim 1.

15. The cell as claimed in claim 14, which is capable of providing the appropriate packaging functions.

16. An avian cell transfected by a plasmid, according to claim 12.

17. A cell as claimed in claim 16, which is capable of providing the appropriate packaging functions.

18. A method for the immortalization of avian cells, wherein said cells are infected or transfected with vectors as claimed in claim 11.

19. A method for the production of a protein encoded by a heterologous gene, wherein infected or transfected cells according to claim 14 are cultured under conditions suitable for expression.

* * * * *